United States Patent [19]

Chu

[11] Patent Number: 4,767,762

[45] Date of Patent: Aug. 30, 1988

[54] TRICYCLIC QUINOLINE AND NAPHTHYRIDE ANTIBACTERIALS

[75] Inventor: Daniel T. Chu, Vernon Hills, Ill.

[73] Assignee: Abbott Laboratories, North Chicago, Ill.

[21] Appl. No.: 937,601

[22] Filed: Dec. 11, 1986

Related U.S. Application Data

[63] Continuation-in-part of Ser. No. 812,663, Dec. 23, 1985, abandoned.

[51] Int. Cl.[4] .................. C07D 401/14; C07D 471/12
[52] U.S. Cl. ..................................... 514/254; 540/575; 544/60; 544/61; 544/62; 544/126; 544/361; 546/83; 514/218; 514/293
[58] Field of Search ................... 544/361, 126, 60, 61, 544/62, 405; 546/83; 514/254, 293, 218, 222, 231, 237; 540/575, 544

[56] References Cited

U.S. PATENT DOCUMENTS

| | | |
|---|---|---|
| 3,541,101 | 11/1970 | Markillie .............................. 546/83 |
| 4,478,834 | 10/1984 | Shroff et al. ......................... 544/361 |
| 4,496,566 | 1/1985 | Matsumoto et al. ................. 544/360 |
| 4,547,503 | 10/1985 | Petersen et al. ..................... 514/254 |
| 4,602,014 | 7/1986 | Yokoyama ............................ 546/83 |

FOREIGN PATENT DOCUMENTS

| | | | |
|---|---|---|---|
| 4032880 | 9/1974 | Japan ................................... 514/254 |
| 6617 | 1/1985 | Japan ................................... 514/254 |

OTHER PUBLICATIONS

Tanasescu et al, Chem. Ber. vol. 92 (1959) pp. 2779–2783.

*Primary Examiner*—Nicholas S. Rizzo
*Assistant Examiner*—Cecilia Shen
*Attorney, Agent, or Firm*—Steven F. Weinstock; Martin L. Katz

[57] ABSTRACT

This invention relates to novel isoxazolo-naphthyridine, isoxazolo-quinoline, isothiazolo-naphthyridine, and isothiazolo-quinoline, derivatives having antibacterial properties.

51 Claims, No Drawings

TRICYCLIC QUINOLINE AND NAPHTHYRIDE ANTIBACTERIALS

This application is a continuation-in-part of U.S. application Ser. No. 812,663 filed Dec. 23, 1985, now abandoned, entitled ISOXAZOLO-NAPHTHYRIDINE, ISOXAZOLO-QUINOLINE, ISOTHIAZOLO-NAPHTHYRIDINE, AND ISOTHIAZOLO-QUINOLINE DERIVATIVES by Daniel Tim-Wo Chu, the disclosure of which is incorporated herein by reference.

This invention relates to novel isoxazolo-naphthyridine, isoxazolo-quinoline isothiazolo-naphthyridine, and isothiazolo-quinoline derivatives having antibacterial properties.

More particularly, this invention relates to compounds having the formula:

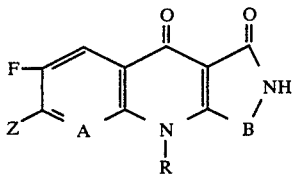
(I)

which may exist in its tautomer form (II)

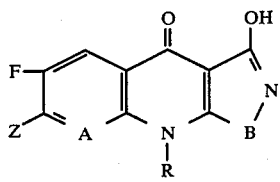
(II)

wherein B is oxygen or sulfur; and R is $C_1$ to $C_4$ alkyl, lowercycloalkyl, alkylamino, aromatic heterocyclic ring having 5 to 6 atoms with the heterocyclic atom being at least one of S, O and N and the remaining atoms being carbon atoms, the aromatic heterocyclic group mono-substituted with a halogen or $C_1$–$C_4$ alkyl. Representative aromatic heterocyclic groups include pyridyl, pyrazinyl, thiazoyl, furyl, thienyl and substituted derivatives thereof.

R can also be a phenyl group of the formula:

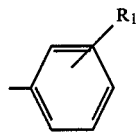

wherein $R_1$ is one, two or three independently selected from hydrogen, halogen, $C_1$ to $C_4$ alkyl, methylenedioxy, or a group having the formula —$OR_2$ wherein $R_2$ is hydrogen or $C_1$ to $C_4$ alkyl.

"A" is a nitrogen atom, a carbon atom with a hydrogen atom attached to it (C—H), a carbon atom with a fluorine atom attached to it (C—F), a carbon atom with a chlorine atom attached to it (C—Cl), or a carbon atom with a bromine atom attached to it (C—Br).

"Z" is an amino group having the formula:

wherein $R_3$ and $R_4$ are independently selected from hydrogen, $C_1$ to $C_4$ alkyl, or alkylamino, hydroxy-substituted $C_1$ to $C_4$ alkyl, $NH_2$, mono-($C_1$–$C_4$) alkylamino and di-($C_1$–$C_4$) alkylamino.

Alternatively, Z can be an aliphatic heterocyclic ring having 1 or 2 hereto atoms which are selected from the group consisting of S, O, N and combinations thereof, with the remaining atoms in the aliphatic heterocyclic ring being carbon atoms, as well as substituted derivatives thereof. In accordance with the practice of the invention, the preferred aliphatic heterocyclic ring has the formula:

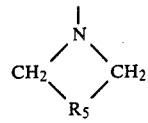

wherein $R_5$ is selected from the group consisting of —$(CH_2)_m$— wherein m is 2 or 3 and a group of the formula —$(CH_2)_n$—$R_6$—$CH_2$— wherein $R_6$ is selected from the group consisting of —S—, —O— and —N— and n is 1 or 2. Also included are substituted derivatives of such heterocyclic rings wherein the substituent is one, two or three independently selected from $C_1$ to $C_4$ alkyl, amino-, alkylaminoalkyl, or hydroxy-substituted $C_1$ to $C_4$ alkyl, alkylamino, hydroxy, halogen, alkanoylamino containing 1 to 4 carbon atoms, an amine group having the formula:

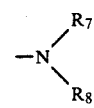

wherein $R_7$ and $R_8$ are each independently selected from the group consisting of hydrogen and $C_1$ to $C_4$ alkyl.

Illustrative of aliphatic heterocyclic groups are piperazinyl groups, piperidinyl groups, pyrrolidinyl groups, morpholino groups, thiomorpholino groups and homopiperazinyl groups (i.e., hexahydro-1-H—1,4-diazepinyl).

Alternatively, Z can be a substituted or unsubstituted bicyclic heterocyclic ring having the formula

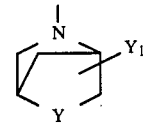

where Y is selected from the group consisting of —S—, —O—, and —N—. The substituents on the substituted bicyclic ring include one or more of $C_1$ to $C_4$ alkyl, hydroxy-substituted $C_1$ to $C_4$ alkyl, phenyl or halophenyl, amino-substituted $C_1$ to $C_4$ alkyl, hydroxy, halogen, alkanoylamido containing 1 to 4 carbon atoms, an amine group having the formula:

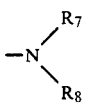

wherein R₇ and R₈ are each independently selected from the group consisting of hydrogen or $C_1$ to $C_4$ alkyl.

Z can also be a phenyl which may be substituted by one to three substituents selected from alkyl to 1 to 4 carbon atoms, alkylsulfonyl of 1 to 4 carbon atoms, fluoro, chloro, hydroxy, hydroxyalkyl of 1 to 3 carbon atoms, amino, alkylamino of 1 to 4 carbon atoms, aminoalkyl of 1 to 3 carbon atoms and aminosulfonyl.

As used herein, the term "halogen" refers to chloro, bromo, fluoro and iodo groups.

The term "$C_1$ to $C_4$ alkyl" refers to branched or straight chain lower alkyl groups including but not limited to methyl, ethyl, propyl, isopropyl, butyl, etc.

The term "halo-substituted alkyl" refers to halogen substituted to $C_1$ to $C_4$ alkyl including but not limited to fluoroethyl group.

The term "lowercycloalkyl" refers to $C_3$ to $C_6$ cycloalkyl groups including cyclopropyl, cyclobutyl, cyclopentyl and cyclohexyl group.

The term "amino" refers to —$NH_2$.

The term "alkylamino" refers to mono- or di-substituted amino group substituted with $C_1$ to $C_4$ alkyl including but not limited to methylamino and ethylmethylamino.

The term "alkanoylamino" refers to a substituent of the formula

wherein $R_9$ is $C_1$ to $C_3$ alkyl and includes but is not limited to acetylamino.

The preferred compounds of the invention are those having the formula:

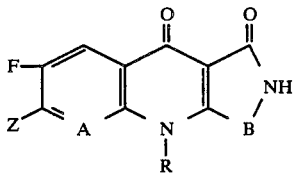

wherein R is ethyl, cyclopropyl, phenyl or substituted phenyl wherein the substituent on the phenyl group is one or more of halogen, methylenedioxy or hydroxy, A and B are as described above and Z is piperazinyl, substituted piperazinyl, aminopyrrolidinyl, substituted pyrrolidinyl, substituted aminopyrrolidinyl, or substituted phenyl as described above.

The chiral centers of the compounds of the invention may have either the "R" or "S" configuration.

Representative of the preferred compounds wherein B is oxygen are 9-ethyl-6-fluoro-7-(1-piperazinyl)-2,3,4,9-tetrahydroisoxazolo[5,4-b][1,8]-naphthyridine-3,4-dione, 9-ethyl-6-fluoro-7-(4-methyl-1-piperazinyl)-2,3,4,9-tetrahydroisoxazolo[5,4-b][1,8]-naphthyridine-3,4-dione, 9-ethyl-6-fluoro-7-(3-amino-1-pyrrolidinyl)-2,3,4,9-tetrahydroisoxazolo[5,4-b][1,8]-naphthyridine-3,4-dione, 9-cyclopropyl-6-fluoro-7-(1-piperazinyl)-2,3,4,9-tetrahydroisoxazolo[5,4-b][1,8]-naphthyridine-3,4-dione, 9-cyclopropyl-6-fluoro-7-(3-methyl-1-piperazinyl)-2,3,4,9-tetrahydroisoxazolo[5,4-b][1,8]-naphthyridine-3,4-dione, 9-cyclopropyl-6-fluoro-7-(4-methyl-1-piperazinyl)-2,3,4,9-tetrahydroisoxazolo[5,4-b][1,8]-naphthyridine-3,4-dione, 9-cyclopropyl-6-fluoro-7-(3-amino-1-pyrrolidinyl)-2,3,4,9-tetrahydroisoxazolo[5,4-b][1,8]-naphthyridine-3,4-dione, 9-cyclopropyl-6-fluoro-7-(3-amino-4-methyl-1-pyrrolidinyl)-2,3,4,9-tetrahydroisoxazolo[5,4-b][1,8]-naphthyridine-3,4-dione, 9-cyclopropyl-6-fluoro-7-(methylphenyl)-2,3,4,9-tetrahydroisoxazolo[5,4,b][1,8]-naphthyridine-3,4-dione, 9-cyclopropyl-6-fluoro-7-(3-ethylaminomethylpyrrolidin-1-yl)-2,3,4,9-tetrahydroisoxazolo[5,4-b][1,8]-naphthyridine-3,4-dione, 9-p-fluorophenyl-6-fluoro-7-(3-methyl-1-piperazinyl)2,3,4,9-tetrahydroisoxazolo[5,4-b][1,8]-naphthyridine-3,4-dione, 9-p-fluorophenyl-6-fluoro-7-(4-methyl-1-piperazinyl)-2,3,4,9-tetrahydroisoxazolo[5,4-b][1,8]-naphthyridine-3,4-dione, 9-p-fluorophenyl-6-fluoro-7(3-amino-1-pyrrolidinyl)-2,3,4,9-tetrahydroisoxazolo[5,4-b][1,8]-naphthyridine-3,4-dione, 9-o,p-difluorophenyl-6-fluoro-7-(3-amino-4-methyl-1-pyrrolidinyl)-2,3,4,9-tetrahydroisoxazolo[5,4-b][1,8]naphthyridine-3,4-dione, 9-ethyl-6-fluoro-7-(1-piperazinyl)-2,3,4,9-tetrahydroisoxazolo[5,4-b]quinoline-3,4-dione, 9-ethyl-6-fluoro-7-(4-methyl-1-piperazinyl)-2,3,4,9-tetrahydroisoxazolo[5,4-b]quinoline-3,4-dione, 9-ethyl-6-fluoro-7-(3-methyl-1-piperazinyl)-2,3,4,9-tetra-hydroisoxazolo[5,4-b]quinoline-3,4-dione, 9-ethyl-6-fluoro-7-(3-amino-1-pyrrolidinyl)-2,3,4,9-tetrahydroisoxazolo[5,4-b]quinoline-3,4-dione, 9-cyclopropyl-6-fluoro-7-(1-piperazinyl)-2,3,4,9-tetrahydroisoxazolo[5,4-b]quinoline-3,4-dione, 9-cyclopropyl-6-fluoro-7-(4-methyl-1-piperazinyl)-2,3,4,9-tetrahydroisoxazolo[5,4-b]quinoline-3,4-dione, 9-cyclopropyl-6-fluoro-7-(3-amino-1-pyrrolidinyl)-2,3,4,9-tetrahydroisoxazolo[5,4-b]quinoline-3,4-dione, 9-cyclopropyl-6-fluoro-7-(3-methyl-1-piperazinyl)-2,3,4,9-tetrahydroisoxazolo[5,4-b]quinoline-3,4-dione, 9-cyclopropyl-6-fluoro-7-(3-amino-4-methyl-1-pyrrolidinyl)-2,3,4,9-tetrahydroisoxazolo[5,4-b]quinoline-3,4-dione, 9-p-fluorophenyl-6-fluoro-7-(1-piperazinyl)-2,3,4,9-tetrahydroisoxazolo[5,4-b]quinoline-3,4-dione, 9-p-fluorophenyl-6-fluoro-7-(4-methyl-1-piperazinyl)-2,3,4,9-tetrahydroisoxazolo[5,4-b]quinoline-3,4-dione, 9-p-fluorophenyl-6-fluoro-7-(3-amino-1-pyrrolidinyl)-2,3,4,9-tetrahydroisoxazolo[5,4-b]quinoline-3,4-dione, 9-o,p-difluorophenyl-6-fluoro-7-(3-methyl-1-piperazinyl)-2,3,4,9-tetrahydroisoxazolo[5,4-b]quinoline-3,4-dione, 9-o,p-difluorophenyl-6-fluoro-7-(3-amino-4-methyl-1-pyrrolidinyl)-2,3,4,9-tetrahydroisoxazolo[5,4-b]quinoline-3,4-dione, 9-ethyl-6,8-difluoro-7-(1-piperazinyl)-2,3,4,9-tetrahydroisoxazolo[5,4-b]quinoline-3,4-dione, 9-ethyl-6,8-difluoro-7-(4-methyl-1-piperazinyl)-2,3,4,9-tetrahydroisoxazolo[5,4-b]quinoline-3,4-dione, 9-ethyl-6,8-difluoro-7-(3-amino-1-pyrrolidinyl)-2,3,4,9-tetrahydroisoxazolo[5,4-b]quinoline-3,4-dione, 9-cyclopropyl-6,8-difluoro-7-(1-piperazinyl)-2,3,4,9-tetrahydroisoxazolo[5,4-b]quinoline-3,4-dione, 9-cyclopropyl-6,8-difluoro-7-(4-methyl-1-piperazinyl)-2,3,4,9-tetrahydroisoxazolo[5,4-b]quinoline-3,4-dione,9-cyclopropyl-6,8-difluoro-7-(3-amino-1-pyrrolidinyl)-2,3,4,9-tetrahydroisoxazolo[5,4-b]quinoline-3,4-dione, 9-p-fluorophenyl-6,8-difluoro-7-(1-piperazinyl)-2,3,49-tetrahydroisoxazolo[5,4-b]quinoline-3,4-dione, 9-p-fluorophenyl-6,8-difluoro-7-(4-methyl-1-piperazinyl)-2,3,4,9-tetrahydroisoxazolo[5,4-b]quinoline-3,4-dione, 9-p-fluorophenyl-6,8-difluoro-7-(3-amino-1-pyrrolidinyl)-2,3,4,9-tetrahydroisoxazolo[5,4-b]quinoline-3,4-dione, 9-ethyl-6-fluoro-7-(1-piperazinyl)-8-chloro-2,3,4,9-tetrahydroisoxazolo[5,4-b]quinoline-3,4-dione, 9-ethyl-6-fluoro-7-(4-methyl-1-piperazinyl)-8-chloro-2,3,4,9-tetrahydroisoxazolo[5,4-b]quinoline-3,4-dione, 9-ethyl-6-fluoro-7-(3-methyl-1-piperazinyl)-8-chloro-2,3,4,9-tetrahydroisoxazolo[5,4-b]quinoline-3,4-dione, 9-ethyl-6-fluoro-7-(3-amino-1-pyrrolidinyl)-8-chloro-2,3,4,9-tetrahydroisoxazolo[5,4-b]quinoline-3,4-dione, 9-cyclopropyl-6-fluoro-7-(1-piperazinyl)-8-chloro-2,3,4,9-tetrahydroisoxazolo[5,4-b]quinoline-3,4-dione, 9-cyclopropyl-6-fluoro-7-(4-methyl-1-piperazinyl)-8-chloro-2,3,4,9-tetrahydroisoxazolo[5,4-b]quinoline-3,4-dione, 9-cyclopropyl-6-fluoro-7-(3-amino-1-pyrrolidinyl)-8-chloro-2,3,4,9-tetrahydroisoxazolo[5,4-b]quinoline-3,4-dione, 9-cyclopropyl-6-fluoro-7-(3-methyl-1-piperazinyl)-8-chloro-2,3,4,9-tetrahydroisoxazolo[5,4-b]quinoline-3,4-dione, 9-cyclopropyl-6-fluoro-7-(3-amino-4-methyl-1-pyrrolidinyl)-8-chloro-2,3,4,9-tetrahydroisoxazolo[5,4-b]quinoline-3,4-dione, 9-p-fluorophenyl-6-fluoro-7-(1-piperazinyl)-8-chloro-2,3,4,9-tetrahydroisoxazolo[5,4-b]quinoline-3,4-dione, 9-p-fluorophenyl-6-fluoro-7-(4-methyl-1-piperazinyl)-8-chloro-2,3,4,9-tetrahydroisoxazolo[5,4-b]quinoline-3,4-dione, 9-p-fluorophenyl-6-fluoro-7-(3-amino-1-pyrrolidinyl)-8-chloro-2,3,4,9-tetrahydroisoxazolo[5,4-b]quinoline-3,4-dione, 9-o,p-difluorophenyl-6-fluoro-7-(3-methyl-1-piperazinyl)-8-chloro-2,3,4,9-tetrahydroisoxazolo[5,4-b]quinoline-3,4-dione, 9-o,p-difluorophenyl-6-fluoro-7-(3-amino-4-methyl-1-pyrrolidinyl)-8-chloro-2,3,4,9-tetrahydroisoxazolo[5,4-b]quinoline-3,4-dione, 9-cyclopropyl-6-fluoro-7-(1-piperazinyl)-8-bromo-2,3,4,9-tetrahydroisoxazolo[5,4-b]quinoline-3,4-dione, 9-cyclopropyl-6-fluoro-7-(3-amino-1-pyrrolidinyl)-8-bromo-2,3,4,9-tetrahydroisoxazolo[5,4-b]quinoline-3,4-dione.

Representative of such preferred compounds wherein B is sulfur are 9-ethyl-6-fluoro-7-(1-piperazinyl)-2,3,4,9-tetrahydroisothiazolo[5,4-b][1,8]-naphthyridine-3,4-dione, 9-ethyl-6-fluoro-7-(4-methyl-1-piperazinyl)-2,3,4,9-tetrahydroisothiazolo[5,4-b][1,8]-naphthyridine-3,4-dione, 9-ethyl-6-fluoro-7-(3-amino-1-pyrrolidinyl)-2,3,4,9-tetrahydroisothiazolo[5,4-b][1,8]-naphthyridine-3,4-dione, 9-cyclopropyl-6-fluoro-7-(1-piperazinyl)-2,3,4,9-tetrahydroisothiazolo[5,4-b][1,8]-naphthyridine-3,4-dione, 9-cyclopropyl-6-fluoro-7-(3-methyl-1-piperazinyl)-2,3,4,9-tetrahydroisothiazolo[5,4-b][1,8]-naphthyridine-3,4-dione, 9-cyclopropyl-6-fluoro-7-(4-methyl-1-piperazinyl)-2,3,4,9-tetrahydroisothiazolo[5,4-b][1,8]-naphthyridine-3,4-dione, 9-cyclopropyl-6-fluoro-7-(3-amino-1-pyrrolidinyl)-2,3,4,9-tetrahydroisothiazolo[5,4-b][1,8]-naphthyridine-3,4-dione, 9-cyclopropyl-6-fluoro-7-(3-amino-4-methyl-1-pyrrolidinyl)-2,3,4,9-tetrahydroisothiazolo[5,4-b][1,8]-naphthyridine-3,4-dione, 9-p-fluorophenyl-6-fluoro-7-(3-methyl-1-piperazinyl)2,3,4,9-tetrahydroisothiazolo[5,4-b][1,8]-naphthyridine-3,4-dione, 9-p-fluorophenyl-6-fluoro-7-(4-methyl-1-piperazinyl)-2,3,4,9-tetrahydroisothiazolo[5,4-b][1,8]-naphthyridine-3,4-dione, 9-p-fluorophenyl-6-fluoro-7-(3-amino-1-pyrrolidinyl)-2,3,4,9-tetrahydroisothiazolo[5,4-b][1,8]-naphthyridine-3,4-dione, 9-o,p-difluorophenyl-6-fluoro-7-(3-amino-4-methyl-1-pyrrolidinyl)-2,3,4,9-tetrahydroisothiazolo[5,4-b][1,8]-naphthyridine-3,4-dione, 9-ethyl-6-fluoro-7-(1-piperazinyl)-2,3,4,9-tetrahydroisothiazolo[5,4-b]quinoline-3,4-dione, 9-ethyl-6-fluoro-7-(4-methyl-1-piperazinyl)-2,3,4,9-tetrahydroisothiazolo[5,4-b]quinoline-3,4-dione, 9-ethyl-6-fluoro-7-(3-methyl-1-piperazinyl)-2,3,4,9-tetrahydroisothiazolo[5,4-b]quinoline-3,4-dione, 9-ethyl-6-fluoro-7-(3-amino-1-pyrrolidinyl)-2,3,4,9-tetrahydroisothiazolo[5,4-b]quinoline-3,4-dione, 9-cyclopropyl-6-fluoro-7-(1-piperazinyl)-2,3,4,9-tetrahydroisothiazolo[5,4-b]quinoline-3,4-dione, 9-cyclopropyl-6-fluoro-7-(4-methyl-1-piperazinyl)-2,3,4,9-tetrahydroisothiazolo[5,4-b]quinoline-3,4-dione, 9-cyclopropyl-6-fluoro-7-(3-amino-1-pyrrolidinyl)-2,3,4,9-tetrahydroisothiazolo[5,4-b]quinoline-3,4-dione, 9-cyclopropyl-6-fluoro-7-(3-methyl-1-piperazinyl)-2,3,4,9-tetrahydroisothiazolo-[5,4-b]quinoline-3,4-dione, 9-cyclopropyl-6-fluoro-7-(3-amino-4-methyl-1-pyrrolidinyl)-2,3,4,9-tetrahydroisothiazolo[5,4-b]quinoline-3,4-dione, 9-cyclopropyl-6-fluoro-7-(3-aminomethyl-4-chloro-1-pyrrolidinyl)-2,3,4,9-tetrahydroisothiazolo[5,4-b]quinoline-3,4-dione, 9-p-fluorophenyl-6-fluoro-7-(1-piperazinyl)-2,3,4,9-tetrahydroisothiazolo[5,4-b]quinoline-3,4-dione, 9-p-fluorophenyl-6-fluoro-7-(4-methyl-1-piperazinyl)-2,3,4,9-tetrahydroisothiazolo[5,4-b]quinoline-3,4-dione, 9-p-fluorophenyl-6-fluoro-7-(3-amino-1-pyrrolidinyl)-2,3,4,9-tetrahydroisothiazolo[5,4-b]quinoline-3,4-dione, 9-o,p-difluorophenyl-6-fluoro-7-(3-methyl-1-piperazinyl)-2,3,4,9-tetrahydroisothiazolo[5,4-b]quinoline-3,4-dione, 9-o,p-difluorophenyl-6-fluoro-7-(3-amino-4-methyl-1-pyrrolidinyl)-2,3,4,9-tetrahydroisothiazolo[5,4-b]quinoline-3,4-dione, 9-ethyl-6,8-difluoro-7-(1-piperazinyl)-2,3,4,9-tetrahydroisothiazolo[5,4-b]quinoline-3,4-dione, 9-ethyl-6,8-difluoro-7-(3-methyl-1-piperazinyl)-2,3,4,9-tetrahydroicoxazolo[5,4-b]quinoline-3,4-dione, 9-ethyl-6,8-difluoro-7-(4-methyl-1-piperazinyl)-2,3,4,9-tetrahydroisothiazolo[5,4-b]quinoline-3,4-dione, 9-ethyl-6,8-difluoro-7-(3-amino-1-pyrrolidinyl)-2,3,4,9-tetrahydroisothiazolo[5,4-b]quinoline-3,4-dione, 9-cyclopropyl-6,8-difluoro-7-(1-piperazinyl)-2,3,4,9-tetrahydroisothiazolo[5,4-b]quinoline-3,4-dione, 9-cyclopropyl-6,8-difluoro-7-(3-aminomethyl-4-chloro-1-pyrrolidinyl)-2,3,4,9-tetrahydroisothiazolo[5,4-b]quinoline-3,4-dione, 9-cyclopropyl-6,8-difluoro-7-(3-ethylaminomethyl-1-pyrrolidinyl)-2,3,4,9-tetrahydroisothiazolo[5,4-b]quinoline-3,4-dione, 9-cyclopropyl-6,8-difluoro-7-(4-methyl-1-piperazinyl)-2,3,4,9-tetrahydroisothiazolo[5,4-b]quinoline-3,4-dione, 9-cyclopropyl-6,8-difluoro-7-(3-amino-1-pyrrolidinyl)-2,3,4,9-tetrahydroisothiazolo[5,4-b]quinoline-3,4-dione, 9-p-fluorophenyl-6,8-difluoro-7-(1-piperazinyl)-2,3,4,9-tetrahydroisothiazolo[5,4-b]quinoline-3,4-dione, 9-p-fluorophenyl-6,8-dihydro-7-(4-methyl-1-piperazinyl)-2,3,4,9-tetrahydroisothiazolo[5,4-b]quinoline-3,4-dione, 9-p-fluorophenyl-6,8-dihydro-7-(3-amino-1-pyrrolidinyl)-2,3,4,9-tetrahydroisothiazolo[5,4-b]quinoline-3,4-dione, 9-ethyl-6-fluoro-7-(1-piperazinyl)-8-chloro-2,3,4,9-tetrahydroisothiazolo[5,4-b]quinoline-3,4-dione, 9-ethyl-6-fluoro-7-(4-methyl-1-piperazinyl)-8-chloro-2,3,4,9-tetrahydroisothiazolo[5,4-b]quinoline-3,4-dione, 9-ethyl-6-fluoro-7-(3-methyl-1-piperazinyl)-8-chloro-2,3,4,9-tetrahydroisothiazolo[5,4-b]quinoline-3,4-dione, 9-ethyl-6-fluoro-7-(3-amino-1-pyrrolidinyl)-8-chloro-2,3,4,9-tetrahydroisothiazolo[5,4-b ]quinoline-3,4-dione, 9-cyclopropyl-6-fluoro-7-(1-piperazinyl)-8-chloro-2,3,4,9-tetrahydroisothiazolo[5,4-b]quinoline-3,4-dione, 9-cyclopropyl-6-fluoro-7-(4-methyl-1-piperazinyl)-8-chloro-2,3,4,9-tetrahydroisothiazolo[5,4-b]quinoline-3,4-dione, 9-cyclopropyl-6-fluoro-7-(3-amino-1-pyrrolidinyl)-8-chloro-2,3,4,9-tetrahydroisothiazolo[5,4-b]quinoline-3,4-dione, 9-cyclopropyl-6-fluoro-7-(3-methyl-1-piperazinyl)-8-chloro-2,3,4,9-tetrahydroisothiazolo[5,4-b]quinoline-3,4-dione, 9-cyclopropyl-6- fluoro-7-(3-amino-4-methyl-1-pyrrolidinyl)-8-chloro-2,3,4,9-tetrahydroisothiazolo[5,4-b]quinoline-3,4-dione, 9-p-fluorophenyl-6-fluoro-7-(1-piperazinyl)-8-chloro-2,3,4,9-tetrahydroisothiazolo[5,4-b]quinoline-3,4-dione, 9-p-fluorophenyl-6-fluoro-7-(4-methyl-1-piperazinyl)-8-chloro-2,3,4,9-tetrahydroisothiazolo[5,4-b]quinoline-3,4-dione, 9-p-fluorophenyl-6-fluoro-7-(3-amino-1-pyrrolidinyl)-8-chloro-2,3,4,9-tetrahydroisothiazolo[5,4-b]quinoline-3,4-dione, 9-o,p-difluorophenyl-6-fluoro-7-(3-methyl-1-piperazinyl)-8-chloro-2,3,4,9-tetrahydroisothiazolo[5,4-b]quinoline-3,4-dione, 9-o,p-difluorophenyl-6-fluoro-7-(3-amino-4-methyl-1-pyrrolidinyl)-8-chloro-2,3,4,9-tetrahydroisothiazolo[5,4-b]quinoline-3,4-dione, 9-cyclopropyl-6-fluoro-7-(1-piperazinyl)-8-bromo-2,3,4,9-tetrahydroisothiazolo[5,4-b]quinoline-3,4-dione, 9-cyclopropyl-6-fluoro-7-(3-amino-1-pyrrolidinyl)-8-bromo-2,3,4,9-tetrahydroisothiazolo[5,4-b]quinoline-3,4-dione.

Also included within the scope of the present invention are pharmaceutically acceptable salts of the foregoing compounds. As used herein, the term "pharmaceutically acceptable salts" refers to non-toxic acid addition salts and alkaline earth metal salts of the compounds of this invention. The salts can be prepared in situ during the final isolation and purification of the compounds of this invention, or separately by reacting the free base or acid functions with a suitable organic acid or base. Representative acid addition salts include the hydrochloride, hydrobromide, sulphate, bisulphate, acetate, oxalate, valerate, oleate, palmitate, stearate, laurate, borate, benzoate, lactate, phosphate, tosylate, mesylate, citrate, maleate, fumarate, succinate, tartrate glucoheptonate, lactobionate, lauryl sulfate salts and the like. Representative alkali or alkaline earth metal salts include the sodium, calcium, potassium and magnesium salts, etc. It has been found that the compounds of the present invention possess antibacterial activity against a wide spectrum of gram positive and gram negative bacteria, as well as enterobacteria. The compounds of the invention are therefor useful in he antibiotic treatment of susceptible bacterial infections in both humans and animals. In addition, the compounds, by reason of their in vitro activity, may be used in scrub solutions for surface inhibition of bacterial growth.

Susceptible organisms generally include those gram positive and gram negative, aerobic and anaerobic organisms whose growth can be inhibited by the compounds of the invention such as Staphylococcus, Lactobacillus, Streptococcus, Sarcina, Escherichia, Enterobacter, Klebseilla, Pseudomonas, Acinetobacter, Proteus, Providencia, Citrobacter, Nisseria, Baccillus, Bacteroides, Campylobacter, Peptococcus, Clostridium, Salmonella, Shigella, Legionella, Serratia, Haemophilus, Brucella, and other organisms.

The compounds of this invention may also be formulated into compositions together with pharmaceutically acceptable carriers for parenteral injection, for oral administration in solid or liquid form, for rectal administration, and the like.

Compositions according to the invention for parenteral injection may comprise pharmaceutically acceptable sterile aqueous or nonaqueous solutions, suspensions or emulsions. Examples of suitable nonaqueous carriers, diluents, solvents or vehicles include propylene glycol, polyethylene glycol, vegetable oils, such as olive oil, and injectable organic esters such as ethyl oleate. Such compositions may also contain adjuvants such as preserving, wetting, emulsifying, and dispersing agents. They may be sterilized, for example, by filtration through a bacteria-retaining filter, or by incorporating sterilizing agents into the compositions. They can also be manufactured in the form of sterile solid compositions which can be dissolved in sterile water, or some other sterile injectable medium immediately before use.

Solid dosage forms for oral administration include capsules, tablets, pills, powders and granules. In such solid dosage forms, the active compound is admixed with at least one inert diluent such as sucrose, lactose or starch. Such dosage forms can also comprise, as is normal practice, additional substances other than diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups and elixers containing inert diluents commonly used in the art, such as water. Besides such inert diluents, compositions can also include adjuvants, such as wetting agents, emulsifying and suspending agents, and sweetening, flavoring and perfuming agents.

Compositions for rectal administration are preferably suppositories which may contain, in addition to the active substance, excipients such as cocoa butter or a suppository wax.

Actual dosage levels of active ingredient in the compositions of the invention may be varied so as to obtain an amount of active ingredient effective to achieve antibacterial activity in accordance with the desired method of administration. The selected dosage level therefore depends upon the nature of the active compound administered, the route of administration, the desired duration of treatment and other factors. Generally, daily dosage levels of the compounds of this invention of about 0.1 to about 750, more preferably about 0.25 to about 500 and most preferably about 0.5 to about 300 mg. of active ingredient per kg. of body weight are effective when administered orally to a mammalian patient suffering from an infection caused by a susceptible organism. If desired, the daily dose may be divided into multiple doses for administration, e.g., two to four times a day.

Compounds wherein B is oxygen according to this invention can be prepared by the following reaction scheme in which Z, R and A are as described above and X is halogen, preferably fluorine or chlorine, and $R_{12}$ and $R_{13}$ are $C_1$ to $C_4$ alkyl group or a phenyl group.

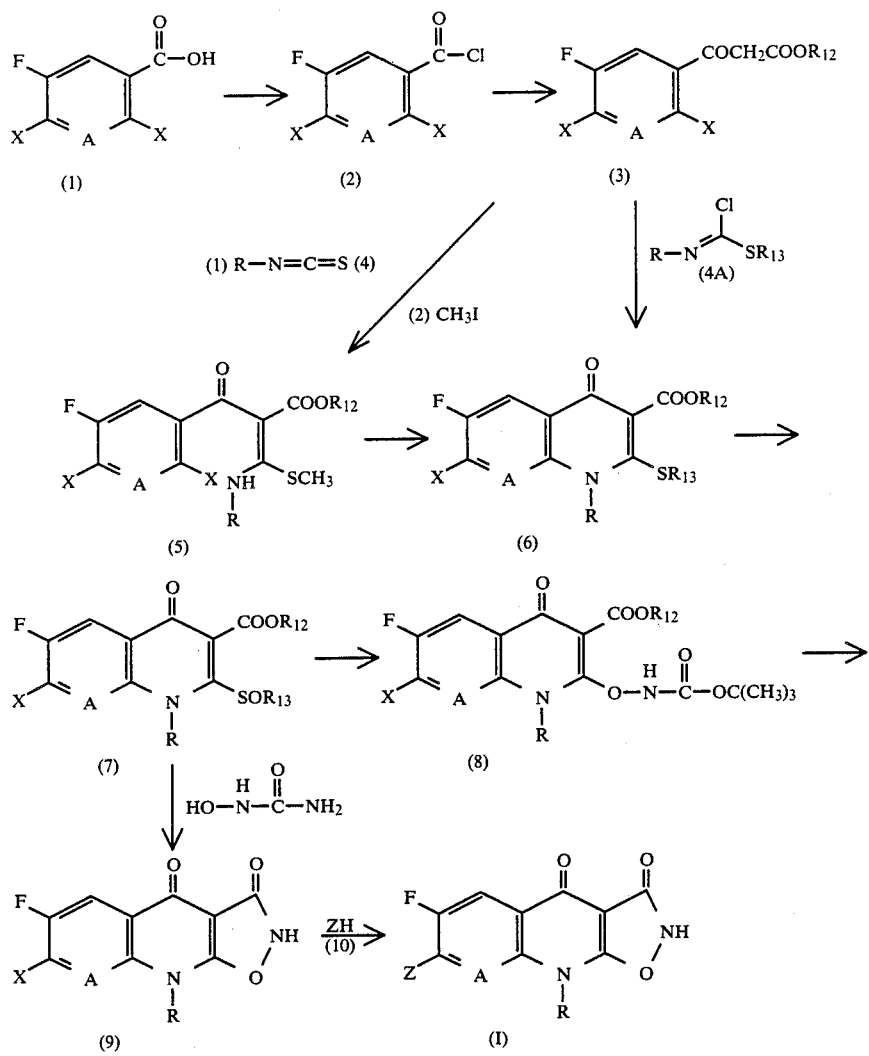

In accordance with the foregoing reaction scheme, the substituted benzoic acid or nicotinic acid (1) can be converted to its acid chloride (2) by treatment with thionyl chloride. Displacement of the acid chloride (2) with malonic acid half ester in the presence of n-butyl lithium yields the beta-ketoester (3). Treatment of the beta-keto ester (3) with sodium hydride in non-aprotic solvent, preferably tetrahydrofuran or dimethylformamide with substituted isothiocyanate (4) at 0° to 40° C. for 3-36 hours followed by the addition of methyl iodide yields the enaminoketoester (5). The latter reaction may be conducted at room temperature or suitable elevated temperature, as desired.

The enaminoketoester (5) is then cyclized, such as by treatment with a strong base preferably sodium hydride to obtain the 1,4-dihydro-4-oxo-quinoline-3-carboxylic acid ester (6) (A=CH, CF or CCl) or 1,4-dihydro-4-oxo-1,8-naphthyridine-3-carboxylic acid ester (6) (A=N). Cyclization is conducted in the presence of an aprotic solvent, such as dimethoxyethane, bis(2-methoxyethyl)ether, dimethylformamide, tetrahydrofuran or chlorobenzene, and is preferably conducted at temperatures of about 20° C. to about 145° C., more preferably at the reflux temperature of the solvent employed.

Alternatively, the 3-carboxylic acid ester (6) can be prepared by treatment of the beta-ketoester (3) with sodium hydride in non-aprotic solvent, preferably tetrahydrofuran or toluene with alkyl or phenyl N-substituted iminochlorothioformate (4A) at room temperature or suitable elevated temperature as desired.

Oxidation of the 3-carboxylic acid ester (6) with metachloroperbenzoic acid yields the sulfoxide (7). The reaction may be conducted at a temperature from 20° C. to 50° C. in the presence of non-polar solvent such as methylene chloride, chloroform. Reacting the sulfoxide (7) with t-butyl N-hydroxycarbamate in the presence of a strong base such as sodium hydride or potassium t-butoxide in aprotic or non-aprotic solvent such as tetrahydrofuran at a temperature from 0° C. to elevated temperature yields the carbamate (8).

Treatment of the carbamate (8) with trifluoroacetic acid at room temperature for a short time yields the free hydroxylamine derivative which is then reacted with sodium bicarbonate in aqueous tetrahydrofuran at room temperature or suitable elevated temperature yields the 7-halo-isoxazolo derivatives (9).

Alternately, the 7-halo-isoxazolo derivative (9) can be prepared by treatment of the sulfoxide (7) with hydroxyurea in an organic solvent or a mixture of organic solvent such as tetrahydrofuran and methanol is the presence of a base such as 1,8-diazabicyclo[5.4.0]undec- 7-ene (DBU) or 1,5-diazabicyclo[4.3.0]non-5-ene (DBN) at room temperature or suitable elevated temperature as desired.

Displacement of the 7-halogen of (9) with an amine (10) yields 9-substituted-7-substituted amino-6-fluoro-2,3,4,9-tetrahydrosioxazolo [5,4-b]quinoline-3,4-dione (A=CH, CF, CCl, or CBr), or 9-substituted-7-substituted amino-6-fluoro-2,3,4,9-tetrahydroisoxazolo[5,4-b][1,8]naphthyridine-3,4-dione (A=N). The reaction may be conducted at a temperature from 20° C. to 130° C. in the presence of a suitable organic polar or non-polar solvent such as pyridine, methylene chloride, chloroform, tetrahydrofuran. 1-methyl-2-pyrrolidinone, dimethyl formamide or dimethyl-sulfoxide. It is desirable to carry out the reaction in the presence of an acid-acceptor such as triethylamine, potassium carbonate and the like at a molar ratio of 1.0 to 1.2 moles of the acid-acceptor per mole of the compound of the formula (9). The amine (10) can also be used as acid acceptor in which 2 or more molar excess of this reagent is used.

Alternately, compounds according to this invention wherein B is oxygen and Z is an amino group, an aliphatic heterocyclic ring, a bicyclic heterocyclic ring, a phenyl or substituted phenyl can also be prepared by the following scheme:

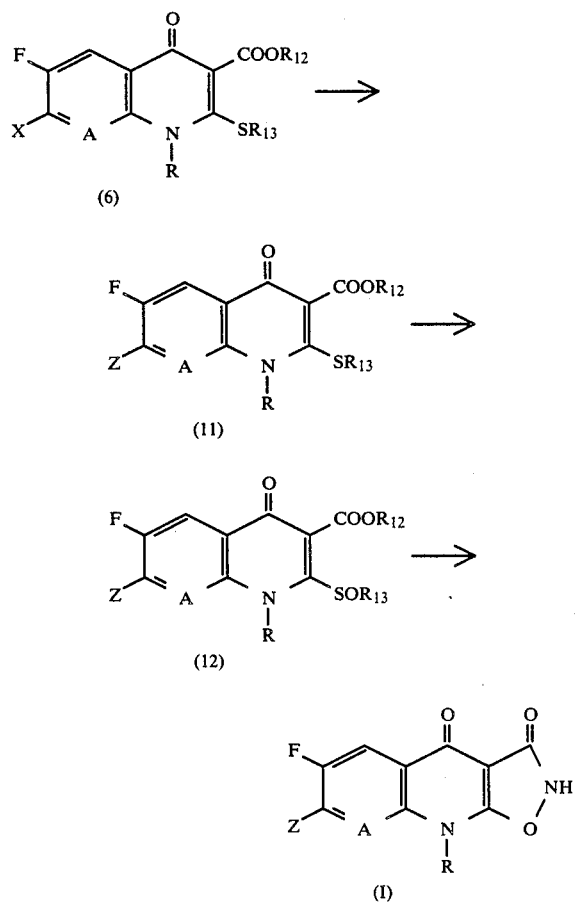

In accordance with the foregoing reaction scheme, where Z is to be an amino group, an aliphatic heterocyclic ring or a bicyclic heterocyclic ring, the 7-halogen of the 3-carboxylic acid ester (6), prepared as described above, can be displayed by an amino derivative (Z) yielding the 7 substituted amino-derivative (11). The displacement reaction may be conducted at a temperature from 20° C. to 130° C. in the presence of a suitable organic polar or non-polar solvent such as pyridine, methylene chloride, chloroform, tetrahydrofuran, 1-methyl-2-pyrrolidinone, dimethylformamide or dimethylsulfoxide.

In the case in structure (11) where Z is to be a phenyl or substituted phenyl group, the compound (11) is formed by coupling the compound (6) with an arylmetallic compound (i.e., phenyl lithium or substituted phenyl lithium) at the 7 position to displace the 7-halogen with a phenyl or substituted group. The coupling reaction is carried out in a reaction-inert solvent, i.e., a solvent which does not interfere with the coupling reaction of the arylmetallic compound with the 7-halo-substituted compound (6). In this case, compounds 11, 12 and I, are represented by a formula wherein the Z group will be a 7-phenyl or substituted phenyl group. Suitable reaction-inert solvents are ethers, e.g., diethylether, dimethoxyethane and tetrahydrofuran. Cosolvents may be used with ethers if desired. These cosolvents may be benzene, toluene, tetramethylethylenediamine (TMEDA) and hexamethylphosphorictriamide (HMPA).

The arylmetallic compounds containing group Z may be prepared by known methods. For instance, they may be prepared by direct lithium-halogen exchange of the corresponding arylhalide using n-butyl, sec-butyl or t-butyl lithium followed by transmetallation by a wide variety of salts by known methods such as described by E. Negishi, Organometallica in Organic Synthesis, Vol. 1, page 104.

Oxidation of compound (11) with metachloroperbenzoic acid or other peracid in methylene chloride or other organic medium, or in an aqueous or non-aqueous acidic medium yields the sulfoxide (12). The reaction may be conducted at room temperature or elevated temperature. Treatment of the sulfoxide (12) with N-hydroxyurea in an aprotic or non-aprotic solvent such as ethanol, tertbutylalcohol, methanol, tetrahydrofuran, dimethylformamide, in the presence of a base such as 1,8-diazabicyclo[5.4.0]undec-7-ene (DBU), 1,5-diazobicyclo[4.3.0]non-5-ene (DBN), sodium hydride or potassium t-butoxide gives the 9-substituted-7-substituted amino-6-fluoro-2,3,4,9-tetrahydroisoxazolo[5,4-b]quinoline-3,4-dione (A=CH, CF, CCl, or CBr) or 9-substituted-7-substituted amino-6-fluoro-2,3,4,9-tetrahydroisoxazolo[5,4-b][1,8]naphthyridine-3,4-dione (A=N).

Compounds wherein B is sulfur according to this invention can be prepared by the following reaction scheme in which Z, R and A are as described above and X is halogen, preferably fluorine or chlorine and $R_{12}$ and $R_{13}$ are $C_1$ to $C_4$ alkyl group or a phenyl group.

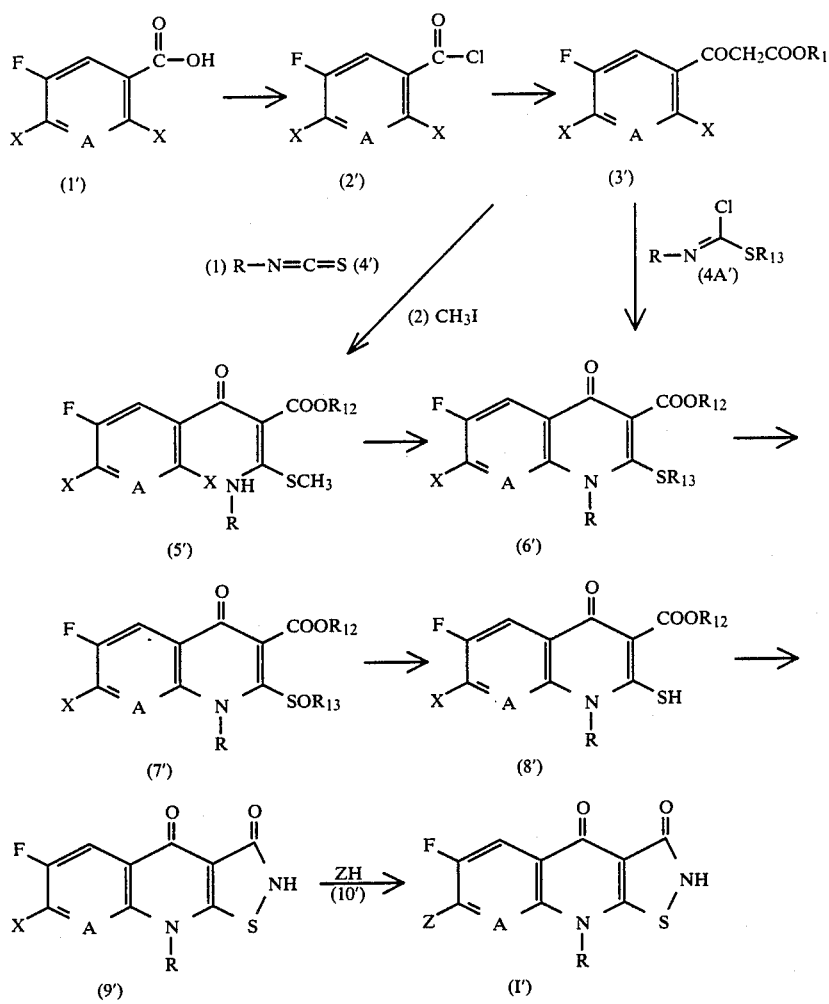

In accordance with the foregoing reaction scheme, the substituted benzoic acid or nicotinic acid (1') can be converted to its acid chloride (2') by treatment with thionyl chloride. Displacement of the acid chloride (2') with malonic acid half ester in the presence of n-butyl lithium yields the beta-ketoester (3'). Treatment of the beta-ketoester (3') with sodium hydride in non-aprotic solvent, preferably tetrahydrofuran with substituted isothiocyanate (4') at 0° to 40° C. for 3-36 hours followed by the addition of methyl iodide yields the enaminoketoester (5'). The latter reaction may be conducted at room temperature or suitable elevated temperature, as desired.

The enaminoketoester (5') is then cyclized, such as by treatment with a strong base preferably sodium hydride to obtain the 1,4-dihydro-4-oxo-quinoline-3-carboxylic acid ester (6') (A=CH, CF, or CCl) or 1,4-dihydro-4-oxo-1,8-naphthyridine-3-carboxylic acid ester (6') (A=N). Cyclization is conducted in the presence of an aprotic solvent, such as dimethoxyethane, bis(2-methoxyethyl)ether, dimethylformamide, tetrahydrofuran or chlorobenzene, and is preferably conducted at temperatures of about 20° C. to about 145° C., more preferably at the reflux temperature of the solvent employed.

Alternatively, the 3-carboxylic acid ester (6') can be prepared by treatment of the beta-ketoester (3') with sodium hydride in non-aprotic solvent, preferably tetrahydrofuran or toluene with alkyl or phenyl N-substituted iminochlorothioformate (4') at room temperature or suitable elevated temperature as desired.

Oxidation of the 3-carboxylic acid ester (6') with meta-chloroperbenzoic acid yields the sulfoxide (7'). The reaction may be conducted at a temperature from 20° C. to 50° C. in the presence of a nonpolar solvent such as methylene chloride or chloroform.

Reaction of (7') with sodium hydrosulfide in an aprotic solvent, preferably aqueous tetrahydrofuran, at elevated temperature yields the 2-mercapto-derivative (8'). Treatment of (8') with hydroxylamine-O-sulfonic acid in the presence of a base, preferably sodium bicarbonate in aprotic solvent, preferably aqueous tetrahydrofuran yields the isothiazolo derivatives (9').

Displacement of the 7-halogen of (9') with an amine (10') yields the 7-substituted amino-isothiazolo derivatives (I'). The reaction may be conducted at a temperature from 20° C. to 130° C. in the presence of a suitable organic polar or non-polar solvent such as pyridine, methylene chloride, chloroform, 1-methyl-2-pyrrolidinone. It is desirable to carry out the reaction in the presence of an acid-acceptor such as triethylamine, potassium carbonate and the like at a molar ratio of 1.0 to 2 moles of the acid acceptor per mole of the compound of formula (9'). The amine (10') can also be used as acid acceptor in which 2 or more molar excess of this reagent is used.

Alternately, compounds according to this invention wherein B is sulfur and Z is an amino group, an aliphatic heterocyclic ring, a bicyclic heterocyclic ring, or a phenyl or substituted phenyl can also be prepared by the following scheme:

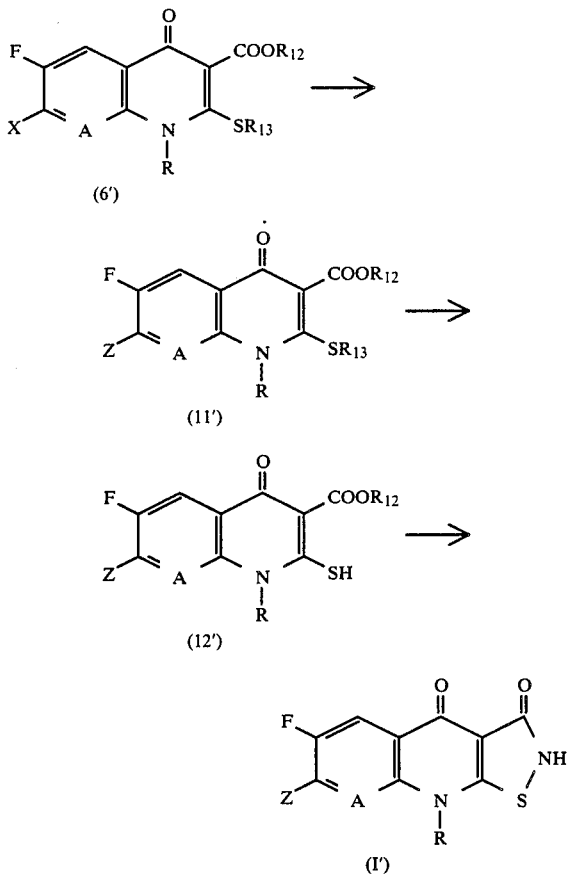

In accordance with the foregoing reaction scheme, where Z is to be an amino group, an aliphatic heterocyclic ring or bicyclic heterocyclic ring, the 7-halogen of the 3-carboxylic acid ester (6'), prepared as described above, can be displaced by an amino group yielding the 7 substituted amino-derivative (11'). The displacement reaction may be conducted at a temperature from 20° C. to 130° C. in the presence of a suitablae organic polar or non-polar solvent such as pyridine, methylene chloride, chloroform, tetrahydrofuran, 1-methyl-2-pyrrolidinone, dimethylformamide or dimethylsulfixide.

In case where Z is to be a phenyl or substituted phenyl group, the compound (11') is formed by coupling the compound (6) with a arylmetallic compound (i.e., phenyl lithium or substituted phenyl lithium) at the 7 position to displace the 7-halogen with a phenyl or substituted group. The coupling reaction is carried out in a reaction-inert solvent, i.e., a solvent which does not interfere with the coupling reaction of the arylmetallic compound with the 7-halo-substituted compound (6). In this case, compounds 11', 12' and I' are represented by a formula wherein the Z group will be a 7-phenyl or substituted phenyl group. Suitable reaction-inert solvents are ethers, e.g. diethylether, dimethoxyethane and tetrahydrofuran. Co-solvents may be used with ethers if desired. These co-solvents may be benzene, toluene, tetramethylethylenediamine (TMEDA) and hexamethylphosphorictriamide (HMPA).

The arylmetallic compounds containing group Z may be prepared by known methods. For instance, they may be prepared by direct lithium-halogen exchange of the corresponding arylhalide using n-butyl, sec-butyl or t-butyl lithium followed by transmetallation by a wide variety of salts by known methods such as described by E. Negishi, Organometallica in Organic Synthesis, Vol. 1, page 104.

Reaction of (11') with sodium hydrosulfide in a aprotic solvent, preferably aqueous tetrahydrofuran, at elevlated temperature yields the 2-mercapto-derivative (12'). Treatment of (12') with hydroxylamine-o-sulfuric acid in the presence of a base, preferably sodium bicarbonate is aprotic solvent, preferably aqueous tetrahydrofuran yields the isothiazolo derivatives (I').

The foregoing may be better understood from the following examples, which are presented for purposes of illustration and are not intended to limit the scope of the inventive concepts. As used in the following examples, the references to compounds, such as (1), (2), (3), or (1'), (2') or (3'), etc., and to substituents, such as R, $R_1$, X, A, etc., refer to the corresponding compounds and substituents in the foregoing reaction schemes and in formulae I and I'. Formula I', of course, corresponds to structure I on page 1 of this specification where B is sulfur. Formula I corresponds to structure I on page 1 wherein B is oxygen.

EXAMPLE 1

9-p-fluorophenyl-6-fluoro-7-(4-methyl-1-piperazinyl)-2,3,4,9-tetrahydroisoxazolo[5,4-b]-quinoline-3,4-dione (a) A mixture of 0.5 g of 2,4,5-trifluorobenzoic acid (1) (A=CH, X=F) and thionyl chloride (4 ml) is heated at refluxing temperature for 1 hour. The solution is evaporated to dryness to give the acid chloride (2). This is added to a solution of 2.50 g of ethyl malonate monoester in 20 ml of tetrahydrofuran ("THF") solution containing 0.51 g of n-butyl lithium at −65° C. The solution is allowed to warm up to room temperature, and then acidified and extracted with ether. The ether extract is washed with saturated $NaHCO_3$ and then water, and dried to yield 0.59 g of the ketoester (3) (A=CH, X=F, $R_{12}=C_2H_5$). b.p. 107° C. at 0.08 mm. of Hg.

(b) 1.79 g of a 60% sodium hydride-in-oil suspension is slowly added to a solution of 6.86 g of p-fluorophenyl isothiocyanate and 9.72 g of the ketoester (3) (A=CH, X=F, $R_{12}=C_2H_5$) in THF (110 ml). The solution is stirred at room temperature under nitrogen atmosphere for 23 hours. After the addition of 2.87 ml of methyliodide, the mixture is stirred for another 16 hours. It is then diluted with 500 ml of water and extracted with ether (3×350 ml). The ether solution is dried over magnesium sulphate and filtered and evaporated under reduced pressure to dryness to give an oil. Purification on silica gel column yields 8.5 g enaminoketoester (5) (A=CH, X=F, $R_{12}=C_2H_5$, R=p-F-phenyl).

To a cold solution of 5.43 g of the preceding product (5), (A=CH, X=F, $R_{12}=C_2H_5$, R=p-F-phenyl) in 60 ml tetrahydrofuran is slowly added 553 mg of a 60% sodium hydride-in-oil suspension. It is then heated at 67° C. for 7 hours and cooled and the mixture is evaporated to dryness. The residue is then dissolved in methylene chloride and washed with water. The organic layer is dried over magnesium sulfate and filtered and evaporated to dryness. Then 40 ml ether/hexane mixture is added to the solid and it is filtered yielding 2.9 g (6) (A=CH, X=F, R$_{12}$=C$_2$H$_5$, R$_{13}$=CH$_3$, R=p-F-phenyl) m.p. 167° C.

(c) Alternately, 4.5 g of a 60% sodium hydride-in-oil suspension is slowly added to a solution of 10.9 g of the methyl iminochlorothioformate (4A) (R=p-fluorophenyl, R$_{13}$=CH$_3$) and 13.7 g of the ketoester (3) (A=CH, X=F, R$_{12}$=C$_2$H$_5$) in THF (400 ml). The mixture is then heated at 60° C. for 24 hours and cooled and the mixture is evaporated to dryness. The residue is then dissolved in methylene chloride and washed and the organic layer is dried and evaporated to dryness yielding (6) (A=CH, X=F, R$_{12}$=C$_2$H$_5$, R$_{13}$=CH$_3$, R=p-F-phenyl) m.p. 167° C.

(d) To a solution of 1.1 g ethyl-1-p-fluorophenyl-2-methylthio-6,7-difluoro-1,4-dihydro-4-oxo-quinoline-3-carboxylate (6) (A=CH, X=F, R$_{13}$=CH$_3$, R$_{12}$=C$_2$H$_5$, R=p-F-phenyl) in 100 ml methylene chloride is added 0.65 g of 80% metachloroperbenzoic acid. After stirring at 25° C. for 6 hours, the solution is diluted with 30 ml of methylene chloride and washed with dilute sodium bicarbonate solution. The organic solvent is dried over magnesium and evaporated to dryness. 15 ml of ether is then added in and it crystallizes yielding, after filtration, 970 mg sulfoxide (7) (A=CH, X=F, R=p-F-phenyl, R$_{12}$=C$_2$H$_5$, R$_{13}$=CH$_3$).

(e) 0.4 g of 60% sodium hydride in oil suspension is added slowly to a solution of 4.1 g of the preceding compound (7) (A=CF, X=F, R$_{12}$=C$_2$H$_5$, R$_{13}$=CH$_3$, R=p-F-phenyl) and 1.5 g of t-butyl N-hydroxycarbamate in 80 ml THF. After stirring at room temperature for 24 hours, the mixture is evaporated to dryness and the residue is dissolved in methylene chloride (150 ml) and washed with dilute sodium bicarbonate solution. The organic layer is dried and evaporated to dryness yielding the carbamate (8). (A=CH, X=F, R=p-F-phenyl, R$_{13}$=CH$_3$, R$_{12}$=C$_2$H$_5$).

2.4 g of the above carbamate (8) is dissolved in 15 ml trifluoroacetic acid. After 10 minutes, the mixture is then evaporated to dryness. The solid is then dissolved in 60 ml THF water mixture and 1.6 g sodium bicarbonate. After 2 hours, it is diluted with water and the mixture is extracted with ether twice. The aqueous portion is acidified with 1N HCl to pH 2. The precipitate is filtered giving 9-p-fluorophenyl-6,7-difluoro-2,3,4,9-tetrahydroisoxazolo[5,4-b]quinoline-3,4-dione (9). (A=CH, X=F, R=p-F-phenyl).

(f) Alternately, the preceding isoxazolo-quinoline compound (9) (H=CH, X=F, R=p-F-phenyl) can be prepared from compound (7) (A=CF, X=F, R$_{12}$=C$_2$H$_5$, R$_{13}$=CH$_3$, R=p-F-phenyl) as follows: 4.09 g of compound (7) is placed in 40 ml THF and 40 ml methanol in an ice bath. 0.84 g of hydroxyurea and 3.2 g of DBU is added to the solution. After ½ hr., the ice bath is removed and the mixture was allowed to react for an additional 1½ hours. The solvent is evaporated off and the residue is dissolved in 500 ml water and extracted with 150 ml of methylene chloride. The aqueous portion is acidified to pH 1 and filtered. The residue is crystallized from ethanol yielding (9) (A=CH, X=F, R=p-F-phenyl.

(g) To a solution of 1.6 g of the preceding isoxazoloquinoline compound (9) (A=CH, A=F, R=p-F-phenyl) in 30 ml pyridine is added 2.5 ml N-methylpiperazine. It is then heated under nitrogen atmosphere at 50° C. for 24 hours. The mixture is evaporated to dryness and is boiled in ethanol for 5 minutes and the mixture is filtered and washed with water, yielding the 9-p-fluorophenyl-6-fluoro-7-(4-methyl-1-piperazinyl)-2,3,4,9-tetrahydroisoxazolo[5,4-b]quinoline-3,4-dione (I) (A=CH, R=p-F-phenyl,

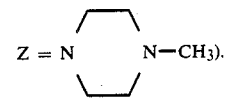

(h) Alternately, 9-p-fluorophenyl-6-fluoro-7-(4-methyl-1-piperazinyl)-2,3,4,9-tetrahydroisoxazolo[5,4-b]quinoline-3,4-dione (I) (A=CH, R=p-F-phenyl,

can be prepared as follows: 5 grams of N-methylperazine is added to a solution of 3.93 grams of (6) in 40 ml pyridine at 55° C. After 2 days, the solvent is removed. Water (100 ml) is added, and the solution is boiled for 3 minutes. The mixture is cooled and filtered. The residue is washed with ether and dried, yielding compound (11). (A=CH, R=p-F-phenyl,

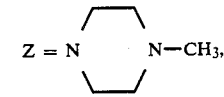

R$_{12}$=C$_2$H$_5$, R$_{13}$=CH$_3$)

(i) A solution of 2.4 g of the preceding compound (11) in trifluoroacetic acid (20 ml) is placed in an ice bath. 0.57 ml of 30 Wt. % hydrogen peroxide in water is added. After 2 hours in an ice bath, the solvent is removed at low temperature. The residue is dissolved in 200 ml methylene chloride and the solution is washed with 50 ml water containing 425 mg sodium bicarbonate. The organic solvent is separated and dried and evaporated to dryness to give the sulfoxide (12). (A=CH, R=p-F-phenyl, R$_{13}$=CH$_3$, R$_{12}$=C$_2$H$_5$,

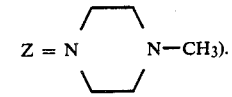

(j) A solution of 2.44 g of the preceding sulfoxide (12) in 20 ml THF and 20 ml methanol is placed in an ice bath. 0.21 g of hydroxyurea and 0.8 g of DBU are added to the solution. After ½ hour, the ice bath is removed. After another 1½ hours, the solvent is evaporated and the residue is dissolved in 200 ml water and extracted with 50 ml methylene chloride. The aqueous phase is acidified to pH 7 with acetic acid and filtered, yielding 9-p-fluorophenyl-6-fluoro-7-(4-methyl-1-piperazinyl)-2,3,4,9-tetrahydroisoxazolo[5,4-b]quinoline-3,4-dione (I).

EXAMPLE 2

9-p-Fluorophenyl-6-fluoro-7-(1-piperazinyl)-2,3,4,9-tetrahydroisoxazolo[5,4-b]-quinoline-3,4-dione The procedure of Example 1 can be repeated, replacing the N-methylpiperazine in 1(g) with piperazine to obtain 9-p-Fluorophenyl-6-fluoro-7-(1-piperazinyl)-2,3,4,9-tetrahydroisoxazolo[5,4-b]quinoline-3,4-dione (I) (A×CH,

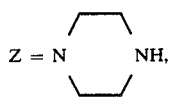

R=p-F-phenyl).

EXAMPLE 3

9-p-Fluorophenyl-6-fluoro-7-(3-t-carbobutoxyamino)1-pyrrolidinyl)-2,3,4,9-tetrahydroisoxazolo[5,4-b]quinoline-3,4-dione The procedure of Example 1 can be repeated, replacing the N-methylpiperazine in 1(g) with 3-t-carbobutoxyamino-pyrrolidine to obtain 9-p-fluorophenyl-6-fluoro-7-(3-t-carbobutoxyamino-1-pyrrolidinyl)-2,3,4,9-tetrahydroisoxazolo[5,4-b]quinoline-3,4-dione (I) (A=CH,

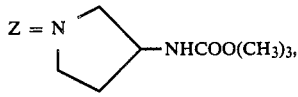

R=p-F-phenyl).

EXAMPLE 4

9-p-Fluorophenyl-6-fluoro-7-(3-amino-1-pyrrolidinyl)-2,3,4,9-tetrahydroisoxazolo[5,4-b]quinoline-3,4-dione The product of Example 3, I (A=CH,

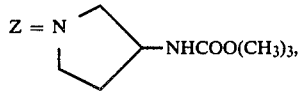

R=p-F-phenyl) can be hydrolyzed by the use of a mixture of trifluoroacetic acid 1N hydrochloric acid (2=1) at room temperature for 30 minutes. After evaporation of solvent to dryness, it yields 9-p-fluorophenyl-6-fluoro-7-(3-amino-1-pyrrolidinyl)-2,3,4,9-tetrahydroisoxazolo-[5,4-b]quinoline-3,4-dione hydrochloride (I) (A=CH,

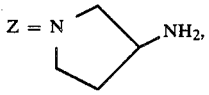

R=p-F-phenyl).

EXAMPLE 5

9-p-Fluorophenyl-6-fluoro-7-(3-methyl-1-piperazinyl)-2,3,4,9-tetrahydroisoxazolo[5,4-b]quinoline-3,4-dione The procedure of Example 1 can be repeated, replacing the N-methylpiperazine in 1(g) with 2-methylpiperazine to obtain 9-p-fluorophenyl-6-fluoro-7-(3-methyl-1-piperazinyl)-2,3,4,9-tetrahydroisoxazolo[5,4-b]quinoline-3,4-dione I (A=CH,

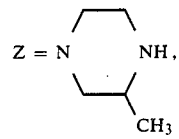

R=p-F-phenyl).

EXAMPLE 6

9-p-Fluorophenyl-6-fluoro-7-(3-amino-4-methyl-1-pyrrolidinyl-2,3,4,9-tetrahydroisoxazolo[5,4-b]quinoline-3,4-dione The procedure of Example 1 can be repeated, replacing the N-methylpiperazine in 1(g) with 3-amino-4-methyl-1-pyrrolidine to obtain 9-p-fluorophenyl-6-fluoro-7-(3-amino-4-methyl-1-pyrrolidinyl)-2,3,4,9-tetrahydroisoxazolo[5,4-b]quinoline-3,4-dione I (A=CH,

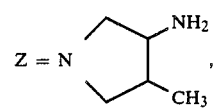

R=p-F-phenyl).

EXAMPLE 7

9-o,p-Difluorophenyl-6-fluoro-7-(4-methyl-1-piperazinyl-2,3,4,9-tetrahydroisoxazolo[5,4-b]quinoline-3,4-dione (a) In the described fashion in Example 1(c) replacing methyl N-p-fluorophenyliminochlorothioformate (4A) (R=p-fluorophenyl) with methyl N-2,4-difluorophenyliminochlorothioformate (4A) (R=2,4-difluorophenyl, $R_{13}$=CH$_3$) one can obtain the quinoline derivative (6) (A=CH, X=F, $R_{12}$=C$_2$H$_5$, $R_{13}$=CH$_3$, R=2,4-difluorophenyl).

(b) By following Example 1 (d and e) the above compound (6) can give 9-2',4'-difluorophenyl-6,7-difluoro, 2,3,4,9-tetrahydroisoazolo[5,4-b]quinoline-3,4-dione (9) (A=CH, X=F, R=2,4 difluorophenyl).

(c) In the described fashion as Example 1(g) the preceeding compound (9) upon reaction with N-methylpiperazine can give the desired 9-o,p-difluorophenyl-6-fluoro-7-(4-methyl-1-piperazinyl)-2,3,4,9-tetrahydroisoxazolo[5,4-b]quinoline-3,4-dione (I) (A=CH,

R=2,4-difluorophenyl).

EXAMPLE 8

9-o,p-Difluorophenyl-6-fluoro-7-(1-piperazinyl)-2,3,4,9-tetrahydroisoxazolo[5,4-b]quinoline-3,4-dione The procedure of Example 7 can be repeated, replacing the N-methylpiperazine in Example 7(c) with piperazine to obtain 9-o,p-difluorophenyl-6-fluoro-7-(1-piperazinyl)-2,3,4,9-tetrahydroisoxazolo[5,4-b]quinoline-3,4-dione (I) (A=CH,

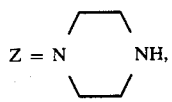

R=o,p-difluorophenyl).

EXAMPLE 9

9-o,p-Difluorophenyl-6-fluoro-7-(3-methyl-1-piperazinyl)-2,3,4,9-tetrahydroisoxazolo[5,4-b]-quinoline-3,4-dione.

In the described fashion as Example 7, replacing N-methylpiperazine in Example 7(c) with 2-methylpiperazine, one can obtain 9-o,p-difluorophenyl-6-fluoro-7-(3-methyl-1-piperazinyl)-2,3,4,9-tetrahydroisoxazolo[5,4-b]quinoline-3,4-dione (I) (A=CH,

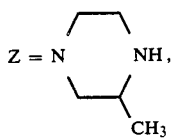

R=2,4-difluorophenyl).

EXAMPLE 10

9-o,p-Difluorophenyl-6-fluoro-7-(3-amino-4-methyl-1-pyrrolidinyl)-2,3,4,9-tetrahydroisoxazolo[5,4-b]quinoline-3,4-dione The procedure of Example 7 can be repeated replacing N-methylpiperazine in Example 7(c) with 3-amino-4-methylpiperazine to give the desired 9-o,p-difluorophenyl-6-fluoro-7-(3-amino-4-methyl-1-pyrrolidinyl)-2,3,4,9-tetrahydroisoxazolo[5,4-b]quinoline-3,4-dione (I) (A=CH,

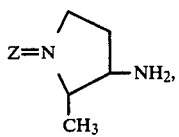

R=2,4-difluorophenyl).

EXAMPLE 11

9-o,p-Difluorophenyl-6-fluoro-7-(1-piperidinyl)-2,3,4,9-tetrahydroisoxazolo[5,4-b]quinoline-3,4-dione In the described fashion as Example 7, replacing N-methylpiperazine in Example 7(c) with piperidine, one can obtain 9-o,p-difluorophenyl-6-fluoro-7-(1-piperidinyl)-2,3,4,9-tetrahydroisoxazolo[5,4-b]quinoline-3,4-dione (I) (A=CH,

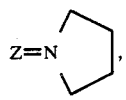

R=2,4-difluorophenyl).

EXAMPLE 12

In the described fashion as Example 1(c) replacing methyl N-p-fluorophenyliminochlorothioformate (4A) (R=p-fluorophenyl) with phenyl N-substituted iminochlorothioformate (4A) where $R_{13}$ is phenyl and, R is cyclopropyl, ethyl or N-formyl-N-methylamino, or in the described fashion as Example 1(b), replacing p-fluorophenyl isothiocyanate with cyclopropyl isothiocyanate, ethyl isothiocyanate or N-formyl-N-methylamino isothiocyanate, one can obtain the following compounds:

(a) Ethyl 1-cyclopropyl-2-methylthio-6,7-difluoro-1,4-dihydro-4-oxo-quinoline-3-carboxylate (6) (A=CH, X=F, $R_{12}=C_2H_5$, $R_{13}=CH_3$, R=cyclopropyl, mp. 137.5° C.)

(b) Ethyl 1-ethyl-2-methylthio-6,7-difluoro-1,4-dihydro-4-oxo-quinoline-3-carboxylate (6) (A=CH, X=F, $R_{12}=C_2H_5$, $R=C_2H_5$, $R_{13}=CH_3$, mp. 113.5° C.

(c) Ethyl 1-N-formyl-N-methylamino-2-phenylthio-6,7-difluoro-1,4-dihydro-4-oxo-quinoline-3-carboxylate (6) (A=CH, X=F, $R_{12}=C_2H_5$, $R=N(CH_3)CHO$, $R_{13}=C_6H_5$)

EXAMPLE 13

In the described fashion as Example 1(d-g), replacing compound (6) (A=CH, X=F, $R_{12}=C_2H_5$, $R_{13}=CH_3$, R=p-fluorophenyl) in Example I(d) with product of Example 12(a) (Compound (6), A=CH, X=F, $R_{12}=C_2H_5$, $C_{13}=CH_3$, R=cyclopropyl) and also replacing N-methylpiperazine in Example 1(g) with an appropriate amine such as N-methylpiperazine, piperazine, 3-t-carbobutoxyamino-pyrrolidine, morpholine, thiomorpholine, 3-aminomethyl-4-chloropyrrolidine, 2-methylpiperazine, 3-amino-4-methylpyrrolidine, one can obtain the following compounds.

(a) 9-cyclopropyl-6-fluoro-7-(4-methyl-1-piperazinyl)-2,3,4,9-tetrahydroisoxazole[5,4-b]quinoline-3,4-dione (I) (A=CH,

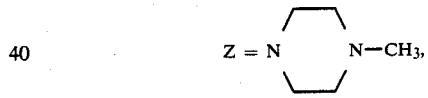

R=cyclopropyl)

(b) 9-cyclopropyl-6-fluoro-7-(1-piperazinyl)-2,3,4,9-tetrahydroisoxazolo[5,4-b]quinoline-3,4-dione (I) (A=CH,

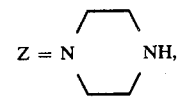

R=cyclopropyl)

(c) 9-cyclopropyl-6-fluoro-7-(3-carbo-t-butoxyamino-1-pyrrolidinyl)-2,3,4,9-tetrahydroisoxazolo[5,4-b]quinoline-3,4-dione (I) (A=CH,

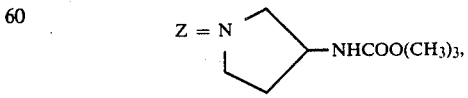

R=cyclopropyl)

(d) 9-cyclopropyl-6-fluoro-7-(1-morpholinyl)-2,3,4,9-tetrahydroisoxazolo[5,4-b]quinoline-3,4-dione (I) (A=CH,

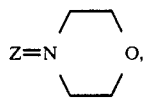

R=cyclopropyl)
(e) 9-cyclopropyl-6-fluoro-7-(1-thiomorpholinyl)-2,3,4,9-tetrahydroisoxazolo[5,4-b]quinoline-3,4-dione (I) (A=CH,

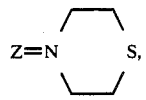

R=cyclopropyl)
(f) 9-cyclopropyl-6-fluoro-7-(3-methyl-1-piperazinyl)-2,3,4,9-tetrahydroisoxazolo[5,4-b]quinoline-3,4-dione (I) (A=CH,

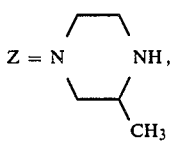

R=cyclopropyl)
(g) 9-cyclopropyl-6-fluoro-7-(3-amino-4-methyl-1-pyrrolidinyl)2,3,4,9-tetrahydroisoxazolo[5,4-b]quinoline-3,4-dione (I) (A=CH,

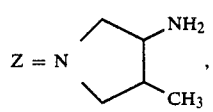

R=cyclopropyl)
(h) 9-cyclopropyl-6-fluoro-7-(3-aminomethyl-4-chloro-1-pyrrolidinyl)-2,3,4,9-tetrahydroisoxazolo[5,4-b]-quinoline-3,4-dione (I) (A=CH,

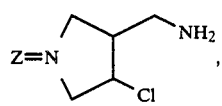

R=cyclopropyl)

EXAMPLE 14

In the described fashion as Example 1(d–g), replacing compound (6) (A=CH, X=F, R$_{12}$=C$_2$H$_5$, R$_{13}$=CH$_3$, R=p-fluorophenyl) in Example 1(d) with the product of Example 12(b) (Compound (6), A=CH, X=F, R$_{12}$=C$_2$H$_5$, R$_{13}$=CH$_3$, R=C$_2$H$_5$) and also replacing N-methyl-piperazine in Example 1(g) with an appropriate amine such as N-methylpiperazine, piperazine, 3-amino-4-methyl-pyrrolidine, 2-methyl-piperazine, 2,2-dimethyl hydrazine and 3-carbo-t-butoxyamino-pyrrolidine, one can obtain the following compounds.
(a) 9-ethyl-6-fluoro-7-(4-methyl-1-piperazinyl)-2,3,4,9-tetrahydroisoxazolo[5,4-b]quinoline-3,4-dione (I) (A=CH,

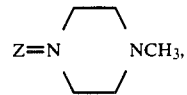

R=C$_2$H$_5$)
(b) 9-ethyl-6-fluoro-7-(1-piperazinyl)-2,3,4,9-tetrahydroisoxazolo[5,4-b]quinoline-3,4-dione (I) (A=CH,

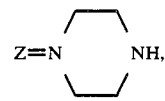

R=C$_2$H$_5$)
(c) 9-ethyl-6-fluoro-7-(3-amino-4-methyl-1-pyrrolidinyl)-2,3,4,9-tetrahydroisoxazolo[5,4-b]quinoline-3,4-dione (I) (A=CH,

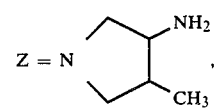

R=C$_2$H$_5$)
(d) 9-ethyl-6-fluoro-7-(3-methyl-1-piperazinyl)-2,3,4,9-tetrahydroisoxazolo[5,4-b]quinoline-3,4-dione (I) (A=CH,

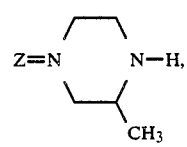

R=C$_2$H$_5$)
(e) 9-ethyl-6-fluoro-7-(2,2-dimethylhydrazyl)-2,3,4,9-tetrahydroisoxazolo[5,4-b]quinoline-3,4-dione (I) (A=CH, Z=NHN(CH$_3$)$_2$, R=C$_2$H$_5$)
(f) 9-ethyl-6-fluoro-7-(3-carbo-t-butoxyamino-1-pyrrolidinyl)-2,3,4,9-tetrahydroisoxazolo[5,4-b]quinoline-3,4-dione (I) (A=CH,

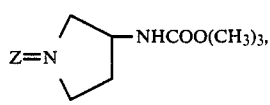

R=ethyl)

EXAMPLE 15

In the same fashion as Example 4, hydrolysis of Examples 13(c) and 14(f) by the use of a mixture of trifluoroacetic acid and dilute hydrochloric acid, one can obtain 9-cyclopropyl-6-fluoro-7-(3-amino-1-pyrrolidinyl)-2,3,4,9-tetrahydroisoxazolo[5,4-b]quinoline-3,4-dione hydrochloride I (A=CH,

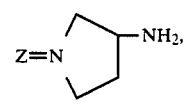

R=cyclopropyl) and 9-ethyl-6-fluoro-7-(3-amino-1-pyrrolidinyl)-2,3,4,9-tetrahydroisoxazolo[5,4-b]quinoline-3,4-dione hydrochloride (I) (A=CH,

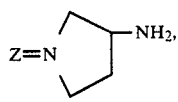

R=ethyl).

EXAMPLE 16

In the described fashion as Example 1(d-g), replacing compound (6) (A=CH, X=F, $R_{12}$=$C_2H_5$, $R_{13}$=$CH_3$, R=p-fluorophenyl) in Example 1(d) with the product of Example 12(c) (compound (6) A=CH, X=F, $R_{12}$=$C_2H_5$, $C_{13}$=$C_6H_5$, R=$NCH_3CHO$) one can obtain 9-(N-formyl-N-methylamino)-6-fluoro-7-(1-4-methylpiperazinyl)-2,3,4,9-tetrahydroisoxazolo[5,4-b]quinoline-3,4-dione (I) (A=CH,

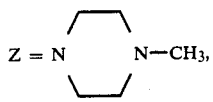

R=$NCH_3CHO$). Hydrolysis of this compound with dilute hydrochloride acid and yields 9-N-methylamino-6-fluoro-7-(4-methyl-1-piperazinyl)-2,3,4,9-tetrahydroisoxazolo[5,4-b]quinoline-3,6 dione (I) (A=CH,

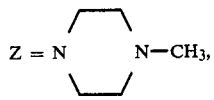

R=$NHCH_3$).

EXAMPLE 17

In the described fashion as Example 1(a), replacing 2,4,5-trifluorobenzoic acid (1) (A=CH, X=F) with 2,6-dichloro-5-fluoronicotinic acid (1) (A=N, X=Cl), 2,3,4,5-tetrafluorobenzoic acid (1) (A=CF, X=F), 3-chloro-2,4,5-trifluorobenzoic acid (1) (A=CCl, X=F) or 3-bromo-2,4,5-trifluqrobenzoic acid (1) (A=CBr, X=F), one can obtain the following ketoesters.

(a) Ethyl 2,6-dichloro-5-fluoronicotinyl acetate (3) (A=N, X=Cl, $R_{12}$=$C_2H_5$)

(b) Ethyl 2,3,4,5-tetrafluorobenzoyl acetate (3) (A=CF, X=F, $R_{12}$=$C_2H_5$)

(c) Ethyl 3-chloro-2,4,5-trifluorobenzoyl acetate (3) (A=CCl, X=F, $R_{12}$=$C_2H_5$)

(d) Ethyl 3-bromo-2,4,5-trifluorobenzoyl acetate (3) (A=CBr, X=F, $R_{12}$=$C_2H_5$)

EXAMPLE 18

Using a procedure similar to Example 1(c), the ketoester (3) (A=CH, X=F, $R_{12}$=$C_2H_5$) is replaced with the ketoester (3) of Example 17(a) A=N, X=Cl, $R_{12}$=$C_2H_5$. Also, the methyl N-p-fluorophenyliminochlorothioformate (4A) (R=p-fluorophenyl) is replaced with an appropriate methyl or phenyl N-substituted iminochlorothioformate (4A) (R equals to 2,4-difluorophenyl, cyclopropyl, ethyl, 4-pyridyl, or p-fluorophenyl). With these changes to Example 1(c) provided, one can obtain the compounds (a)-(e) below. Alternatively, following the procedure described in 1(b) using or replacing the p-fluorophenylisothiocyanate with cyclopropyl isothiocyanate, ethyl isothiocyanate, 4-pyridylisothiocyanate and 2,4-difluorophenyl isothiocyanate, one can obtain the same compounds (a)-(e).

(a) Ethyl 1-p-fluorophenyl-2-methylthio-6-fluoro-7-chloro-1,4-dihydro-4-oxo-1,8-naphthyridine-3-carboxylate (6) (A=N, X=Cl, $R_{12}$=$C_2H_5$, $R_{13}$=$CH_3$, R=p-fluorophenyl, mp. 176° C.)

(b) Ethyl 1-o,p-difluorophenyl-2-methylthio-6-fluoro-7-chloro-1,4-dihydro-4-oxo-1,8-naphthyridine-3-carboxylate (6) (A=N, X=Cl, $R_{12}$=$C_2H_5$, $R_{13}$=$CH_3$, R=2,4-difluorophenyl)

(c) Ethyl 1-cyclopropyl-2-phenylthio-6-fluoro-7-chloro-1,4-dihydro-4-oxo-1,8-naphthyridine-3-carboxylate (6) (A=N, X=Cl, $R_{12}$=$C_2H_5$, R=cyclopropyl, $R_{13}$=$C_6H_5$)

(d) Ethyl 1-ethyl-2-phenylthio-6-fluoro-7-chloro-1,4-dihydro-4-oxo-1,8-naphthyridine-3-carboxylate (6) (A=N, X=Cl, $R_{12}$=$C_2H_5$, R=$C_2H_5$, $R_{13}$=$C_6H_5$)

(e) Ethyl 1-(4-pyridyl)-2-methylthio-6-fluoro-7-chloro-1,4-dihydro-4-oxo-1,8-naphthyridine-3-carboxylate (6) (A=CH, X=F, $R_{12}$=$C_2H_5$, R=4-pyridyl, $R_{13}$=$C_2H_5$)

EXAMPLE 19

In the described fashion as Example 1(c), replacing the ketoester (3)(A=CH, X=F, $R_{12}$=$C_2H_5$) with the ketoester of Example 17(b)(3)(A=CF, X=F, $R_{12}$=$C_2H_5$) and also replacing the methyl N-p-fluorophenyliminochlorothioformide (4A) (R=p-F-phenyl) with an appropriate methyl or phenyl N-iminochlorothioformate such as where R is p-fluorophenyl, 2,4-difluorophenyl, cyclopropyl, ethyl, 3,4-methylenedioxyphenyl, 2,4,6-trifluorophenyl, 4-pyridyl, 2-methyl-4-pyridyl, 3-chloro-4-pyridyl, 2-pyrazinyl, 3-furyl, p-hydroxyphenyl and p-methoxyphenyl, one can obtain the compounds in (a)-(n) below. Alternatively, following the procedure described in 1(b), using or replacing the p-fluorophenylisothiocyanate with cyclopropylisothiocyanate, ethylisothiocyanate, 4-pyridylisothiocyanate, 3-chloro-4-pyridylisothiocyanate, p-methoxyphenylisothiocyanate, 3,4-methylenedioxyisothiocyanate, 2,4,6-trifluorophenylisothiocyanate, one can obtain the same compounds (a)-(n).

(a) Ethyl 1-p-fluorophenyl-2-methylthio-6,7,8-trifluoro-1,4-dihydro-4-oxo-quinoline-3-carboxylate (6) (A=CF, X=F, $R_{12}$=$C_2H_5$, R=p-fluorophenyl, $R_{13}$=$CH_3$)

(b) Ethyl 1-o,p-difluorophenyl-2-methylthio-6,7,8-trifluoro-1,4-dihydro-4-oxo-quinoline-3-carboxylate (6) (A=CF, X=F, $R_{12}$=$C_2H_5$, $R_{13}$=$CH_3$, R=2,4-difluorophenyl)

(c) Ethyl 1-cyclopropyl-2-phenylthio-6,7,8-trifluoro-1,4-dihydro-4-oxo-quinoline-3-carboxylate (6) (A=CF, X=F, $R_{12}$=$C_2H_5$, R=cyclopropyl, $R_{13}$=$C_6H_5$, mp=135°-137° C.)

(d) Ethyl 1-ethyl-2-phenylthio-6,7,8-trifluoro-1,4-dihydro-4-oxo-quinoline-3-carboxylate (6) (A=CF, X=F, $R_{12}C_2H_5$, R=$C_2H_5$, $R_{13}$=$C_6H_5$, mp=91° C.)

(e) Ethyl 1-(3',4'-methylenedioxyphenyl)-2-methylthio-6,7,8-trifluoro-1,4-dihydro-4-oxo-quinoline-3-carboxylate (6) (A-CF, A=F, $R_{12}$=$C_2H_5$, $R_{13}$=$CH_3$, R=3,4-methylenedioxyphenyl)

(f) Ethyl 1-(2',4',6'-trifluorophenyl)-2-methylthio-6,7,8-trifluoro-1,4-dihydro-4-oxo-quinoline-3-carboxylate (6) (A=CF, X=F, $R_{12}=C_2H_5$, $R_{13}=CH_3$, R=2,4,6-trifluorophenyl)

(g) Ethyl 1-(2-methyl-4-pyridyl)-2-methylthio-6,7,8-trifluoro-1,4-dihydro-4-oxo-quinoline-3-carboxylate (6) (A=CF, X=F, $R_{12}=C_2H_5$, R=2-methyl-4-pyridyl, $R_{13}=CH_3$)

(h) Ethyl 1-(4-pyridyl)-2-methylthio-6,7,8-trifluoro-1,4-dihydro-4-oxo-quinoline-3-carboxylate (6) (A=CF, X=F, $R_{12}=C_2H_5$, R=3-chloro-4-pyridyl, $R_{13}=CH_3$)

(i) Ethyl 1-(3-chloro-4-pyridyl)-2-methylthio-6,7,8,-trifluoro-1,4-dihydro-4-oxo-quinoline-3-carboxylate (6) (A=CF, X=F, $R_{12}=C_2H_5$, R=3-chloro-4-pyridyl, $R_{13}=CH_3$)

(j) Ethyl 1-(2-pyrazinyl)-2-methylthio-6,7,8-trifluoro-1,4-dihydro-4-oxo-quinoline-3-carboxylate (6) (A=CF, X=F, $R_{12}=C_2H_5$, R=2-pyrazinyl, $R_{13}=CH_3$)

(k) Ethyl 1-(3-furyl)-2-methylthio-6,7,8-trifluoro-1,4-dihydro-4-oxo-quinoline-3-carboxylate (6) (A=CF, X=F, $R_{12}=C_2H_5$, R=3-furyl, $R_{13}=CH_3$)

(l) Ethyl 1-(4-hydroxyphenyl)-2-methylthio-6,7,8-trifluoro-1,4-dihydro-4-oxo-quinoline-3-carboxylate (6) A=CF, X=F, $R_{12}=C_2H_5$, R=4-hydroxyphenyl, $R_{13}=CH_3$)

(m) Ethyl 1-(4-methoxyphenyl)-2-methylthio-6,7,8-trifluoro-1,4-dihydro-4-oxo-quinoline-3-carboxylate (6) (A=CF, X=F, $R_{12}=C_2H_5$, R=4-methoxyphenyl, $R_{13}=CH_3$)

(n) Ethyl 1-(4-methylphenyl)-2-methylthio-6,7,8-trifluoro-1,4-dihydro-4-oxo-quinoline-3-carboxylate (6) (A=CF, X=F, $R_{12}=C_2H_5$, R=4-methylphenyl, $R_{13}=CH_3$)

EXAMPLE 20

In the described fashion as Example 1(c), replacing the ketoester (3)(A=CH, X=F, $R_{12}=C_2H_5$) with the ketoester of Example 17(c)(3), A=CCl, X=F, $RA_{12}=C_2H_5$) and also replacing the methyl N-p-fluorophenyliminochlorothioformide (4A) (R=p-F-phenyl) with an appropriate methyl or phenyl iminochlorothioformate (such as R equals p-fluorophenyl, 2,4-difluorophenyl, cyclopropyl, or ethyl), one can obtain compounds (a)–(d) below. Alternatively, following the procedure described in 1(b), using or replacing the p-fluorophenylisothiocyanate with cyclopropylisothiocyanate, ethylisothiocyanate, or 2,4-difluorophenylisothiocyanate, one can obtain the same compounds (a)–(d):

(a) Ethyl 1-p-fluorophenyl-2-methylthio-6,7-difluoro-8-chloro-1,4-dihydro-4-oxo-quinoline-3-carboxylate (6) (A=CCl, X=F, $R_{12}=C_2H_5$, R=p-fluorophenyl, $R_{13}=CH_3$)

(b) Ethyl 1-o,p-difluorophenyl-2-methylthio-6,7-difluoro-8-chloro-1,4-dihydro-4-oxo-quinoline-3-carboxylate (6) (A=CCl, X=F, $R_{12}=C_2H_5$, R=o,p-difluorophenyl, $R_{13}=CH_3$)

(c) Ethyl 1-cyclopropyl-2-phenylthio-6,7-difluoro-8-chloro-1,4-dihydro-4-oxo-quinoline-3-carboxylate (6) (A=CCl, X=F, $R_{12}=C_2H_5$, $R_{13}=C_6H_5$, R=cyclopropyl)

(d) Ethyl 1-ethyl-2-phenylthio-6,7-difluoro-8-chloro-1,4-dihydro-4-oxo-quinoline-3-carboxylate (6) (A=CCl, X=F, $R_{12}=C_2H_5$, $R_{13}=C_6H_5$, R=ethyl)

EXAMPLE 21

In the described fashion as Example 1(c) replacing the ketoester (3) (A=CH, X=F, $R_{12}=C_2H_5$) with the ketoester (3) of Example 17(d) A=CBr, X=F, $R_{12}=C_2H_5$ and also replacing the methyl N-p-fluorophenyliminochlorothioformate (4A) (R=p-fluorophenyl) with an appropriate phenyl N-substituted iminochlorothioformate (4A) where R equals cyclopropyl or ethyl, one can obtain the following compounds:

(a) Ethyl 1-cyclopropyl-2-phenylthio-6,7-difluoro-8-bromo-1,4-dihydro-4-oxo-quinoline-3-carboxylate (6) (A=CBr, X=F, $R_{12}=C_2H_5$, $R_{13}=C_2H_5$, R=cyclopropyl)

(b) Ethyl 1-ethyl-2-phenylthio-6,7-difluoro-8-bromo-1,4-dihydro-4-oxo-quinoline-3-carboxylate (6) (A=CBr, X=F, $R_{12}=C_2H_5$, $R_{13}=C_6H_5$, R=ethyl)

EXAMPLE 22

In the described fashion as Example 1(d–g), replacing compound (6) (A=CH, X=F, $R_{12}=C_2H_5$, $R_{13}=CH_3$, R=p-fluorophenyl) in Example 1(d), with compound (6) of Examples 18(a–e), 19(a–n), 20(a–d) or 21(a–b) and also replacing N-methylpiperazine in Example 1(g) with an appropriate amine (such as N-methylpiperazine, piperazine, 2-methylpiperazine, 3-t-carbobutoxyaminopyrrolidine, 3-amino-4-methyl-1-pyrrolidine, pyrrolidine, piperidine, morpholine, thiomorpholine, 3-aminomethyl-1-pyrrolidine, ethylamine, ethanolamine, 1,2-diaminoethane, N-methylhydrazine, 3-ethylaminomethylpyrrolidine, N,N-dimethylhydrazine, 3-hydroxymethyl-1-pyrrolidine, 3-methylaminopyrrolidine, 2-p-fluorophenylpiperazine, 2-phenylpiperazine, 3-hydroxypyrrolidine, 3-aminomethyl-4-chloropyrrolidine or homopiperazine), one can obtain the following compounds.

(a) 9-p-fluorophenyl-6-fluoro-7-(4-methyl-1-piperazinyl)-2,3,4,9-tetrahydroisoxazolo[5,4-b][1,8]naphthyridine-3,4-dione (I) (A=N,

R=p-fluorophenyl)

(b) 9-p-fluorophenyl-6-fluoro-7-(1-piperazinyl)-2,3,4,9-tetrahydroisoxazolo[5,4-b][1,8]-naphthyridine-3,4-dione (I) (A=N,

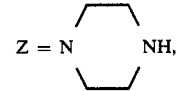

R=p-fluorophenyl)

(c) 9-p-fluorophenyl-6-fluoro-7-(3-t-carbobutoxyamino-1-pyrrolidinyl)-2,3,4,9-tetrahydroisoxazolo[5,4b][1,8]naphthyridine-3-4-dione (I) (A=N,

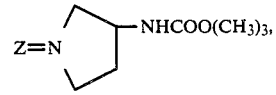

R=p-fluorophenyl)

(d) 9-p-fluorophenyl-6-fluoro-7-thiomorpholinyl-2,3,4,9-tetrahydroisoxazolo[5,4-b][1,8]-naphthyridine-3,4-dione (I) (A=CH,

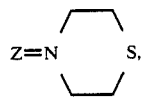

R=p-fluorophenyl)

(e) 9-o,p-difluorophenyl-6-fluoro-7-(4-methyl-1-piperazinyl)-2,3,4,9-tetrahydroisoxazolo[5,4-b]1,8-naphthyridine-3,4-dione (I) (A=N,

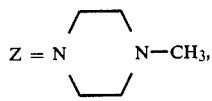

R=o,p-difluorophenyl)

(f) 9-o,p-difluorophenyl-6-fluoro-7-(1-piperazinyl)-2,3,4,9-tetrahydroisoxazolo[5,4-b][1,8]-naphthyridine-3,4-dione (I) (A=N,

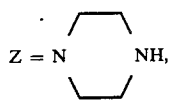

R=o,p-difluorophenyl)

(g) 9-o,p-difluorophenyl-6-fluoro-7-(3-t-carbobutoxyamino-1-pyrrolidinyl)-2,3,4,9-tetrahydroisoxazolo[5,4-b][1,8]-naphthyridine-3,4-dione (I) (A=N,

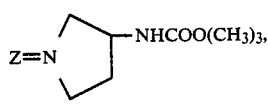

R=o,p-difluorophenyl)

(h) 9-cyclopropyl-6-fluoro-7-(4-methyl-1-piperazinyl)-2,3,4,9-tetrahydroisoxazolo[5,4-b][1,8]naphthyridine-3,4-dione (I) (A=N,

R=cyclopropyl)

(i) 9-cyclopropyl-6-fluoro-7-(1-piperazinyl)-2,3,4,9-tetrahydroisoxazolo[5,4-b][1,8]naphthyridine-3,4-dione (I) (A=N,

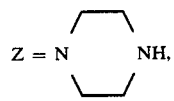

R=cyclopropyl)

(j) 9-cyclopropyl-6-fluoro-7-(3-t-carbobutoxyamino-1-pyrrolidinyl)2,3,4,9-tetrahydroisoxazolo[5,4-b][1,8]naphthyridine-3,4-dione (I) (A=N,

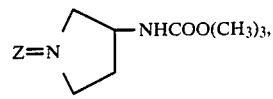

R=cyclopropyl)

(k) 9-cyclopropyl-6-fluoro-7-morpholinyl-2,3,4,9-tetrahydroisoxazolo[5,4-b][1,8]naphthyridine-3,4-dione (I) (A=N,

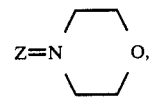

R=cyclopropyl)

(l) 9-ethyl-6-fluoro-7-(4-methyl-1-piperazinyl)-2,3,4,9-tetrahydroisoxazolo[5,4-b][1,8]naphthyridine-3,4-dione (I) (A=N,

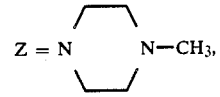

R=C₂H₅)

(m) 9-ethyl-6-fluoro-7-(1-piperazinyl)-2,3,4,9-tetrahydroisoxazolo[5,4-b][1,8]naphthyridine-3,4-dione (I) (A=N,

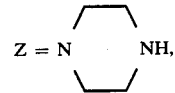

R=C₂H₅)

(n) 9-ethyl-6-fluoro-7-(3-t-carbobutoxyamino-1-pyrrolidinyl) 2,3,4,9-tetrahydroisoxazolo[5,4-b][1,8]napthyridine-3,4-dione (I) (A=N,

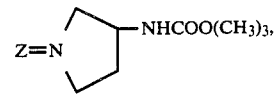

R=C₂H₅)

(o) 9-ethyl-6-fluoro-7-piperidinyl-2,3,4,9-tetrahydroisoxazolo[5,4-b][1,8]naphthyridine-3,4-dione (I) (A=N,

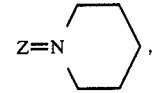

R=C₂H₅)

(p) 9-(4-pyridyl)-6-fluoro-7-(4-methyl-1-piperazinyl)-2,3,4,9-tetrahydroisoxazolo[5,4-b][1,8]naphthyridine-3,4-dione (I) (A=N,

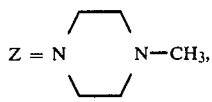

R=4-pyridyl)

(q) 9-(N-formyl-N-methylamino)-6-8-difluoro-7-(4-methyl-1-piperazinyl)-2,3,4,9-tetrahydroisoxazolo[5,4-b]quinoline-3,4-dione (I) (A=CF,

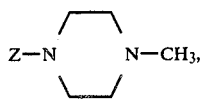

R=NCH₃CHO)

(r) 9-p-fluorophenyl-6,8-difluoro-7-(4-methyl-1-piperazinyl)-2,3,4,9-tetrahydroisoxazolo[5,4-b]quinoline-3,4-dione (I) (A=CF,

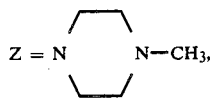

R=p-fluorophenyl)

(s) 9-p-fluorophenyl-6,8-difluoro-7-(1-piperazinyl)-2,3,4,9-tetrahydroisoxazolo[5,4-b]quinoline-3,4-dione (I) (A=CF,

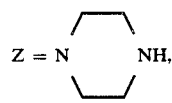

R=p-fluorophenyl)

(t) 9-p=fluorophenyl-6,8-difluoro-7-(3-t-carbobutoxyamino-1-pyrrolidinyl)-2,3,4,9-tetrahydroisoxazolo[5,4-b]quinoline-3,4-dione (I) (A=CF,

R=p-fluorophenyl)

(u) 9-p-fluorophenyl-6,8-difluoro-7-(3-aminoethyl-1-pyrrolidinyl)-2,3,4,9-tetrahydroisoxazolo[5,4-b]quinoline-3,4-dione (I) (A=CF,

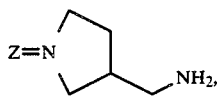

R=p-fluorophenyl)

(v) 9-o,p-difluorophenyl-6,8-difluoro-7-(4-methyl-1-piperazinyl)-2,3,4,9-tetrahydroisoxazolo[5,4-b]quinoline-3,4-dione (I) (A=CF, R=2,4-difluorophenyl)

(w) 9-o,p-difluorophenyl-6,8-difluoro-7-(1-piperazinyl)-2,3,4,9-tetrahydroisoxazolo[5,4-b]quinoline-3,4-dione (I) (A=CF, R=2,4-difluorophenyl)

(x) 9-o,p-difluorophenyl-6,8-difluoro-7-(3-t-carbobutoxyamino-1-pyrrolidinyl)-2,3,4,9-tetrahydroisoxazolo[5,4-b]quinoline-3,4-dione (I) (A=CF, R=2,4-difluorophenyl)

(y) 9-cyclopropyl-6,8-difluoro-7-(4-methyl-1-piperazinyl)-2,3,4,9-tetrahydroisoxazolo[5,4-b]quinoline-3,4-dione (I) (A=CF,

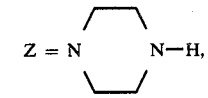

R=cyclopropyl)

(z) 9-cyclopropyl-6,8-difluoro-7-piperazinyl)-2,3,4,9-tetrahydroisoxazolo[5,4-b]quinoline-3,4-dione (I) (A=CF, R=cyclopropyl)

(aa) 9-cyclopropyl-6,8-difluoro-7-(3-t-carbobutoxyamino-1-pyrrolidinyl)-2,3,4,9-tetrahydroisoxazolo[5,4-b]quinoline-3,4-dione (I) (A=CF,

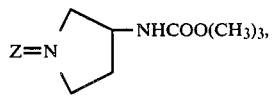

R=cyclopropyl)

(bb) 9-cyclopropyl-6,8-difluoro-7-thiomorpholinyl-2,3,4,9-tetrahydroisoxazolo[5,4-b]quinoline-3,4-dione (I) (A=CF,

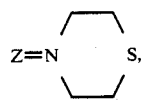

R=cyclopropyl)
(cc) 9-ethyl-6,8-difluoro-7-(4-methyl-1-piperazinyl)-2,3,4,9-tetrahydroisoxazolo[5,4-b]quinoline-3,4-dione (I) (A=CF,

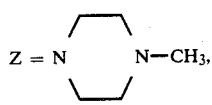

R=C₂H₅)
(dd) 9-ethyl-6,8-difluoro-7-(1-piperazinyl)-2,3,4,9-tetrahydroisoxazolo[5,4-b]quinoline-3,4-dione (I) (A=CF,

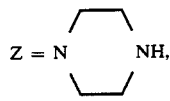

R=C₂H₅)
(ee) 9-ethyl-6,8-difluoro-7-(3-t-carbobutoxyamino-1-pyrrolidinyl)-2,3,4,9-tetrahydroisoxazolo[5,4-b]quinoline-3,4-dione (I) (A=CF,

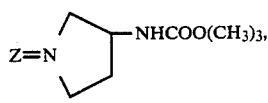

R=C₂H₅)
(ff) 9-(3',4'-methylenedioxyphenyl)-6,8-difluoro-7-(4-methyl-1-piperazinyl)-2,3,4,9-tetrahydroisoxazolo[5,4-b]quinoline-3,4-dione (I) (A=CF,

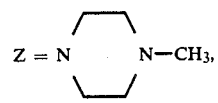

R=3,4-methylenedioxyphenyl)
(gg) 9-(2',4',6'-trifluorophenyl)-6,8-difluoro-7-(4-methyl-1-piperazinyl)-2,3,4,9-tetrahydroisoxazolo[5,4-b]quinoline-3,4-dione (I) (A=CF,

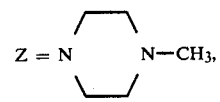

R=2,4,6-trifluorophenyl)
(hh) 9-p-fluorophenyl-6-fluoro-7-(3-methyl-piperazinyl)-2,3,4,9-tetrahydroisoxazolo[5,4-b][1,8]naphthyridine-3,4-dione (I) (A=N,

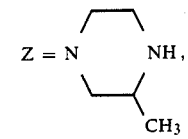

R=p-fluorophenyl)
(ii) 9-p-fluorophenyl-6-fluoro-7-(3-amino-4-methyl-1-pyrrolidinyl)-2,3,4,9-tetrahydroisoxazolo[5,4-b][1,8]naphthyridine-3,4-dione (I) (A=N,

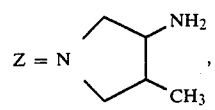

R=p-fluorophenyl)
(jj) 9-o,p-fluorophenyl-6-fluoro-7-(3-methyl-piperazinyl)-2,3,4,9-tetrahydroisoxazolo[5,4-b][1,8]naphthyridine-3,4-dione (I) (A=N,

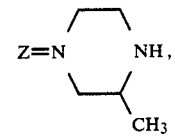

R=o,p-fluorophenyl)
(kk) 9-o,p-difluorophenyl-6-fluoro-7-(3-amino-4-methyl-pyrrolidinyl)-2,3,4,9-tetrahydroisoxazolo[5,4-b][1,8]naphthyridine-3,4-dione (I) (A=N,

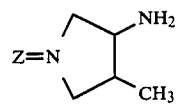

R=o,p-fluorophenyl)
(ll) 9-cyclopropyl-6-fluoro-7-(3-methyl-1-piperazinyl)-2,3,4,9-tetrahydroisoxazolo[5,4-b][1,8]naphthyridine-3,4-dione (I) (A=N,

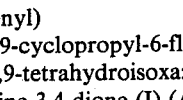

R=cyclopropyl)
(mm) 9-cyclopropyl-6-fluoro-7-(3-amino-4-methyl-1-pyrrolidinyl)-2,3,4,9-tetrahydroisoxazolo[5,4-b][1,8]naphthyridine-3,4-dione (I) (A=N,

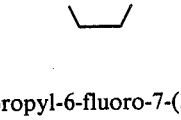

R=cyclopropyl)
(nn) 9-p-fluorophenyl-6,8-difluoro-7-(3-amino-4-methyl-1-pyrrolidinyl)-tetrahydroisoxazolo[5,4-b]quinoline-3,4-dione (I) (A=CF,

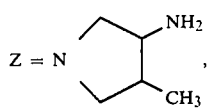

R=p-fluorophenyl)

(oo) 9-o,p-difluorophenyl-6,8-difluoro-7-(3-methyl-1-piperazinyl)tetrahydroisoxazolo[5,4-b]quinoline-3,4-dione (I) (A=CF,

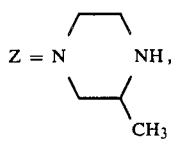

R=o,p-difluorophenyl)

(pp) 9-cyclopropyl-6,8-difluoro-7-(3-methyl-piperazinyl)-2,3,4,9-tetrahydroisoxazolo[5,4-b]quinoline-3,4-dione (I) (A=CF,

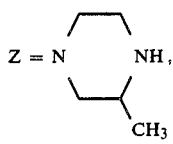

R=cyclopropyl)

(qq) 9-cyclopropyl-6,8-difluoro-7-(3-amino-4-methyl-1-pyrrolidinyl)-2,3,4,9-tetrahydroisoxazolo[5,4-b]quinoline-3,4-dione (I) (A=CF,

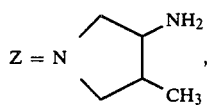

R=cyclopropyl)

(rr) 9-ethyl-6,8-difluoro-7-(3-amino-4-methyl-1-pyrrolidinyl)-2,3,4,9-tetrahydroisoxazolo[5,4-b]quinoline-3,4-dione (I) (A=CF,

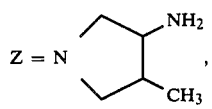

R=ethyl)

(ss) 9-(2-methyl-4-pyridyl)-6,8-difluoro-7-ethylamino-2,3,4,9-tetrahydroisoxazolo[5,4-b]quinoline-3,4-dione (I) (A=CF, Z=NHC2H5, R=2-methyl-4-pyridyl)

(tt) 9-(4-pyridyl)-6,8-difluoro-7-homopiperazine-2,3,4,9-tetrahydroisoxazolo[5,4-b]quinoline-3,4-dione (I) (A=CF,

R=4-pyridyl)

(uu) 9-(3-chloro-4-pyridyl)-6,8-difluoro-7-hydroxyethylamino-2,3,4,9-tetrahydroisoxazolo[5,4-b]quinoline-3,4-dione (I) (A=CF, Z=NHC2H4OH, R=3-chloro-4-pyridyl)

(vv) 9-(2-pyrazinyl)-6,8-difluoro-7-aminoethylamino-2,3,4,9-tetrahydroisoxazolo[5,4-b]quinoline-3,4-dione (I) (A=CF, Z=NHC2H4NH2, R=2-pyrazinyl)

(ww) 9-(3-furyl)-6,8-difluoro-7-(2-methyl-1-hydrazyl)-2,3,4,9-tetrahydroisoxazolo[5,4-b]quinoline-3,4-dione (I) (A=CF, Z=NHNHCH3, R=3-furyl)

(xx) 9-(4-hydroxyphenyl)-6,8-difluoro-7-(2,2-dimethyl-1-hydrazyl)-2,3,4,9-tetrahydroisoxazolo[5,4-b]quinoline-3,4-dione I (A=CF, Z=NHN(CH3)2, R=4-hydroxyphenyl)

(yy) 9-(4-methoxyphenyl)-6,8-difluoro-7-(3-hydroxymethyl-1-pyrrolidinyl)2,3,4,9-tetrahydroisoxazolo[5,4-b]quinoline-3,4-dione (I) (A=CF,

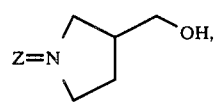

R=4-methoxyphenyl)

(zz) 9-cyclopropyl-6,8-difluoro-7-(3-methylamino-1-pyrrolidinyl)-2,3,4,9-tetrahydroisoxazolo[5,4-b]quinoline-3,4-dione (I) (A=CF,

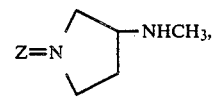

R=cyclopropyl)

(aaa) 9-cyclopropyl-6,8-difluoro-7-(3-p-fluorophenyl-1-piperazinyl)-2,3,4,9-tetrahydroisoxazolo[5,4-b]quinoline-3,4-dione (I) (A=CF,

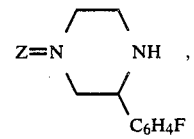

R=cyclopropyl)

(bbb) 9-cyclopropyl-6,8-difluoro-7-(3-phenyl-1-piperazinyl)-2,3,4,9-tetrahydro-isoxazolo[5,4-b]quinoline-3,4-dione (I) (A=CF,

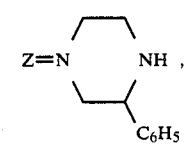

R=cyclopropyl)

(ccc) 9-cyclopropyl-6,8-difluoro-7-(3-hydroxy-1-pyrrolidinyl)-2,3,4,9-tetrahydroisoxazolo[5,4-b]quinoline-3,4-dione (I) (A=CF,

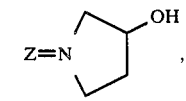

R=cyclopropyl)

(ddd) 9-cyclopropyl-6,8-difluoro-7-(3-aminomethyl-4-chloro-1-pyrrolidinyl)-2,3,4,9-tetrahydroisoxazolo[5,4-b]quinoline-3,4-dione (I) (A=CH,

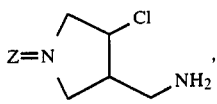

R=cyclopropyl)
(eee) 9-(4-methyphenyl-6,8-difluoro-7-(1-piperazinyl)-2,3,4,9-tetrahydroisoxazolo[5,4-b]quinoline-3,4-dione (I) (A=CH,

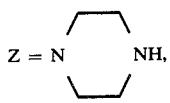

R=4-methylphenyl)
(fff) 9-cyclopropyl-6-fluoro-7-(3-ethylaminomethyl-1-pyrrolidinyl)-2,3,4,9-tetrahydroisoxazolo[5,4-b][1,8]-naphthyridine-3,4-dione (I) (A-N,

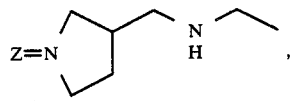

R=cyclopropyl)
(ggg) 9-ethyl-6,8-difluoro-7-(3-methyl-1-piperazinyl)-2,3,4,9-tetrahydroisoxazol[5,4-b]quinoline-3,4-dione (I) (A=CF

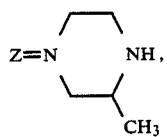

R=ethyl)
(hhh) 9-p-fluorophenyl-6-fluoro-8-chloro-7-(4-methyl-1-piperazinyl)-2,3,4,9-tetrahydroisoxazolo[5,4-b]quinoline-3,4,-dione (I) (A=CCl,

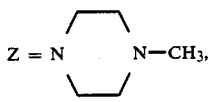

R=p-fluorophenyl)
(iii) 9-p-fluorophenyl-6-fluoro-8-chloro-7-(1-piperazinyl)-2,3,4,9-tetrahydroisoxazolo[5,4-b]quinoline-3,4,-dione (I) (A=CCl,

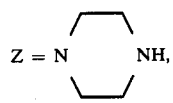

R=p-fluorophenyl)
(jjj) 9-p-fluorophenyl-6-fluoro-8-chloro-7-(3-t-carbobutoxyamino-1-pyrrolidinyl)-2,3,4,9-tetrahydroisoxazolo[5,4-b]quinoline-3,4-dione (I) (A=CCl,

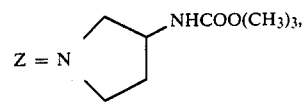

R-p-fluorophenyl)
(kkk) 9-o,p-difluorophenyl-6-difluoro-8-chloro-7-(1-piperazinyl)-2,3,4,9-tetrahydroisoxazolo[5,4-b]quinoline-3,4-dione (I) (A=CCl,

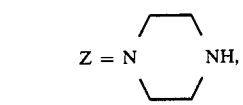

R=2,4-difluorophenyl)
(lll) 9-o,p-difluorophenyl-6-difluoro-8-chloro-7-(3-t-carbobutoxyamino-1-pyrrolidinyl)-2,3,4,9-tetrahydroisoxazolo[5,4-b]quinoline-3,4-dione (I) (A=CCl,

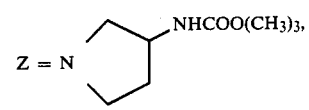

R=2,4=difluorophenyl)
(mmm) 9-cyclopropyl-6-fluoro-8-chloro-7-(4-methyl-1-piperazinyl)-2,3,4,9-tetrahydroisoxazolo[5,4-b]quinoline-3,4-dione (I) (A=CCl,

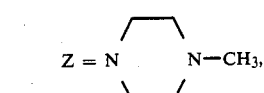

R=cyclopropyl)
(nnn) 9-cyclopropyl-6-fluoro-8-chloro-7-piperazinyl)-2,3,4,9-tetrahydroisoxazolo[5,4-b]quinoline-3,4-dione (I) (A=CCl,

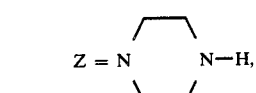

R=cyclopropyl)
(ooo) 9-cyclopropyl-6-fluoro-8-chloro-7-(3-t-carbobutoxyamino-1-pyrrolidinyl)-2,3,4,9-tetrahydroisoxazolo[5,4-b]quinoline-3,4-dione (I) (A=CCl,

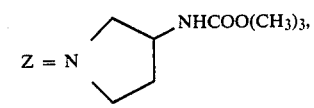

R=cyclopropyl)
(ppp) 9-cyclopropyl-6-fluoro-8-chloro-7-(3-methyl-piperazinyl)-2,3,4,9-tetrahydroisoxazolo[5,4-b]quinoline-3,4-dione (I) (A=CCl,

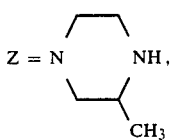

R=cyclopropyl)

(qqq) 9-cyclopropyl-6-fluoro-8-chloro-7-(3-amino-4-methyl-1-pyrrolidinyl)-2,3,4,9-tetrahydroisoxazolo[5,4-b]quinoline-3,4-dione (I) (A=CCl,

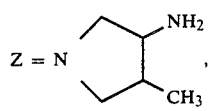

R=cyclopropyl)

(rrr) 9-ethyl-6-difluoro-8-chloro-7-4-methyl-1-piperazinyl)-2,3,4,9-tetrahydroisoxazolo[5,4-b]quinoline-3,4-dione (I) (A=CCl,

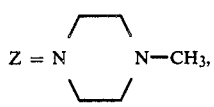

R=C₂H₅)

(sss) 9-ethyl-6-fluoro-8-chloro-7-(1-piperazinyl)-2,3,4,9-tetrahydroisoxazolo[5,4-b]quinoline-3,4-dione (I) (A=CCl,

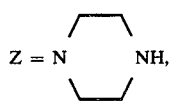

R=C₂H₅)

(ttt) 9-ethyl-6-fluoro-8-chloro-7-(3-t-carbobutoxyamino-1-pyrrolidinyl)-2,3,4,9-tetrahydroisoxazolo[5,4-b]quinoline-3,4-dione (I) (A=CCl,

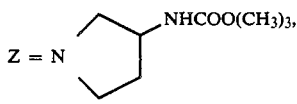

R=C₂H₅)

(uuu) 9-cyclopropyl-6-fluoro-8-bromo-7-(3-t-carboxyamino-1-pyrrolidinyl)-2,3,4,9-tetrahydroisoxazolo[5,4-b]quinoline-3,4-dione (I) (A=CBr,

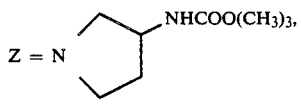

R=cyclopropyl)

(vvv) 9-ethyl-6-fluoro-8-bromo-7-(3-t-carbobutoxyamino-1-pyrrolidinyl)=2,3,4,9-tetrahydroisoxazolo[5,4-b]quinoline-3,4-dione (I) (A=CBr,

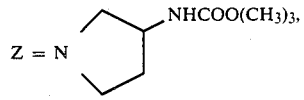

R=ethyl)

EXAMPLE 23

In the described fashion as Example 4, hydrolysis of the compounds of Examples 22(c), (g), (j), (n), (t), (x), (aa), (ee), (jjj), (lll), (ooo), (ttt), (uuu), and (vvv) by the use of dilute hydrochloric acid and trifluoro acetic acid, one can obtain the following compounds.

(a) 9-p-fluorophenyl-6-fluoro-7-(3-amino-1-pyrrolidinyl)-2,3,4,9-tetrahydroisoxazolo[5,4-b][1,8]naphthyridine-3,4-dione hydrochloride (I) (A=N,

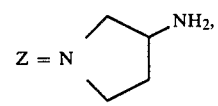

R=p-fluorophenyl)

(b) 9-o,p-difluorophenyl-6-fluoro-7-(3-amino-1-pyrrolidinyl)-2,3,4,9-tetrahydroisoxazolo[5,4-b][1,8]naphthyridine-3,4-dione hydrochloride (I) (A=N,

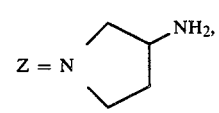

R=2,4-difluorophenyl)

(c) 9-cyclopropyl-6-fluoro-7-(3-amino-1-pyrrolidinyl)-2,3,4,9-tetrahydroisoxazolo[5,4-b][1,8]naphthyridine-3,4-dione hydrochloride (I) (A=N,

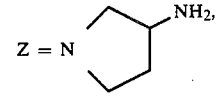

R=cyclopropyl (d) 9-ethyl-6-fluoro-7-(3-amino-1-pyrrolidinyl)-2,3,4,9-tetrahydroisoxazolo[5,4-b][1,8]naphthyridine-3,4-dione hydrochloride (I) (A=N,

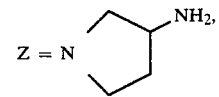

R=C₂H₅)

(e) 9-p-fluorophenyl-6,8-difluoro-7-(3-amino-1-pyrrodinyl)-2,3,4,9-tetrahydroisoxazolo[5,4-b]quinoline-3,4-dione hydrochloride (I) (A=CF,

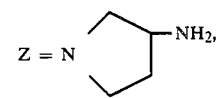

R=p-fluorophenyl)

(f) 9-o,p-difluorphenyl-6,8-difluoro-7-(3-amino-1-pyrrolidinyl)-2,3,4,9-tetrahydroisoxazolo[5,4-b]quinoline-3,4-dione hydrochloride (I) (A=CF,

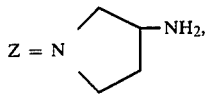

R=2,4-difluorophenyl)

(g) 9-cyclopropyl-6,8-difluoro-7-(3-amino-1-pyrrolidinyl)-2,3,4,9-tetrahydroisoxazolo[5,4-b]quinoline-3,4-dione hydrochloride (I) (A=CF,

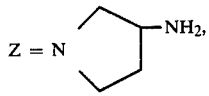

R=cyclopropyl)

(h) 9-ethyl-6,8-difluoro-7-(3-amino-1-pyrrolidinyl)-2,3,4,9-tetrahydroisoxazolo[5,4-b]quinoline-3,4-dione hydrochloride (I) (A=CF,

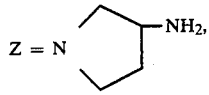

R=C₂H₅)

(i) 9-p-fluorophenyl-6-fluoro-8-chloro-7-(3-amino-1-pyrrolidinyl)-2,3,4,9-tetrahydroisoxazolo[5,4-b]quinoline-3,4-dione hydrochloride (I) (A=CCl,

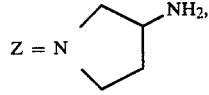

R=p-fluorophenyl)

(j) 9-o,p-difluorophenyl-6-fluoro-8-chloro-7-(3-amino-1-pyrrolidinyl)-2,3,4,9-tetrahydroisoxazolo[5,4-b]quinoline-3,4-dione hydrochloride (I) (A=CCl,

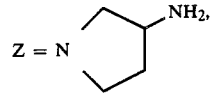

R=o,p-difluorophenyl (k) 9-cyclopropyl-6-fluoro-8-chloro-7-(3-amino-1-pyrrolidinyl)-2,3,4,9-tetrahydroisoxazolo[5,4-b]quinoline-3,4-dione hydrochloride (I) (A=CCl,

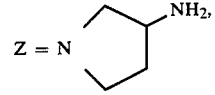

R=cyclopropyl)

(l) 9-ethyl-6-fluoro-8-chloro-7-(3-amino-1-pyrrolidinyl)-2,3,4,9-tetrahydroisoxazolo[5,4-b]quinoline-3,4-dione hydrochloride (I) (A=CCl,

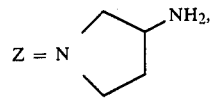

R=ethyl)

(m) 9-cyclopropyl-6-fluoro-8-bromo-7-(3-amino-1-pyrrolidinyl)-2,3,4,9-tetrahydroisoxazolo[5,4-b]quinoline-3,4-dione hydrochloride (I) (A=CBr,

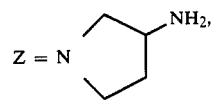

R=cyclopropyl (n) 9-ethyl-6-fluoro-8-bromo-7-(3-amino-1-pyrrolidinyl)-2,3,4,9-tetrahydroisoxazolo[5,4-b]quinoline-3,4-dione hydrochloride (I) (A=CBr,

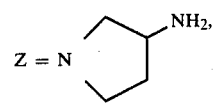

R=ethyl)

EXAMPLE 24

9-p-fluorophenyl-6-fluoro-7-(4-methyl-1-piperazinyl)-2,3,4,9-tetrahydroisothiazolo[5,4-b][1,8]naphthyridine-3,4-dione (a) A mixture of 0.5 g of 2.6-dichloro-5-fluoronicotinic acid (1') (A=N, X=Cl) and thionyl chloride (4 ml) is heated at refluxing temperature for 1 hour. The solution is evaporated to dryness to give the acid chloride (2'). This is added to a solution of 2.54 g of ethyl malonate monoester in 20 ml of tetrahydrofuran ("THF") solution containing 0.52 g of n-butyl lithium at −65° C. The solution is allowed to warm up to room temperature, and then acidified and extracted with ether. The ether extract is washed with saturated NaHCO₃ and then water, and dried to yield 0.49 g of the ketoester (3') (A=N, X=Cl, R₁₂=C₂H₅).

(b) 1.25 g of a 60% sodium hydride-in-oil suspension is slowly added to a solution of 4.92 g of p-fluorophenyl isothiocyanate and 8.56 g of the ketoester (3') (A=N, X=Cl, R₁₂=C₂H₅ in THF (100 ml). The solution is stirred at room temperature under nitrogen atmosphere for 20 hours. After the addition of 2 ml of methyliodide, the mixture is stirred for another 16 hours. It is then diluted with 500 ml of water and extracted with ether (3×350 ml). The ether solution is dried over magnesium sulphate and filtered and evaporated under reduced pressure to dryness. 20 ml ethanol is added to dissolve the residue and the insoluble material is filtered. The filtrate is diluted with 30 ml ethanol. After standing for awhile, it crystallizes and is filtered yielding 6 g enaminoketoester (5') (A=N, X=Cl, R₁₂=C₂H₅, R=p-F-phenyl) m.p. 121° C.

To a cold solution of 5.37 g of the preceding product (5'), (A=N, X=Cl, R₁₂=C₂H₅, R=p-F-phenyl) in 60 ml tetrahydrofuran is slowly added 490 mg of a 60% sodium hydride-in-oil suspension. It is then heated at 60° C. for 17 hours and cooled and the mixture is evaporated to dryness. The residue is then dissolved in methylene chloride and washed with water. The organic layer is dried over magnesium sulfate and filtered and evaporated to dryness. Then 20 ml ether is added to the solid and it is filtered yielding 4.6 g (6′) (A=N, X=Cl, $R_{13}$=CH$_3$, $R_{12}$=C$_2$H$_5$, R=p-F-phenyl) m.p. 176° C.

(c) Alternately, 5 g of a 60% sodium hydride-in-oil suspension is slowly added to a solution of 12.1 g of the methyl iminochlorothioformate (4A′) (R=p-fluorophenyl, $R_{13}$=CH$_3$) and 17.2 g of the ketoester (3′) (A=N, X=Cl, $R_{12}$=C$_2$H$_5$). The mixture is then heated at 60° C. for 24 hours and cooled and the mixture is evaporated to dryness. The residue is then dissolved in methylene chloride and washed with water and the organic layer is dried and evaporated to dryness. 50 ml of ether is added and the precipitate is filtered yielding 12.1 g (6′) (A=N, X=Cl, $R_{12}$=C$_2$H$_5$, R=p-F-phenyl) m.p. 176° C., $R_{13}$=CH$_3$).

(d) To a solution of 1.37 g ethyl -1-p-fluorophenyl-2-methylthio-6-fluoro-7-chloro-1,4-dihydro-4-oxo-1,8-naphthyridine-3-carboxylate (6′) (A=N, X=Cl, $R_{12}$=C$_2$H$_5$, $R_{13}$=CH$_3$, R=p-F-phenyl) in 100 ml methylene chloride is added 0.7 g of 80% metachloroperbenzoic acid. After stirring at 20° C. for 4 hours, the solution is dilute with 100 ml of methylene chloride and washed with water. The organic solvent is dried over magnesium and evaporated to dryness. 15 ml of ether is then added in and it crystallizes yielding, after filtration, the sulfoxide derivative (7′) (A=N, $R_{12}$=C$_2$H$_5$, X=Cl, R=p-F phenyl), $R_{13}$=CH$_3$) m.p. 227°-228° C.

(e) 4 ml of 0.92N sodium hydrosulfide solution is added to 1.57 g of the preceding compound (7′) (A=N, $R_{12}$=C$_2$H$_5$, X=Cl, R=p-F-phenyl) in 10 ml of tetrahydrofuran. After the solution is stirred at room temperature for one day, the mixture is evaporated to dryness and redissolved in water (30 ml) containing 420 mg sodium bicarbonate. The aqueous solution is being extracted twice with ether. The aqueous solution is gently evaporated off any residue ether and cooled. 6 ml of 1N hydrochloric acid is then added and the precipitate is filtered yielding the 2-thiol derivative (8′) (A=N, $R_{12}$=C$_2$H$_5$, X=Cl, R=p-F-phenyl).

(f) To a solution of 794 mg of the preceding compound (8′) (A=N, X=Cl, R=p-F-phenyl) and 1.26 g sodium bicarbonate in 10 ml of tetrahydrofuran and 40 ml water solution is added 520 mg hydroxylamine-O-sulfonic acid is added. After stirring for 3 hours, the mixture is filtered and the aqueous portion is diluted with water (20 ml) and extracted with ether (30 ml×2) and the aqueous portion is acidified with dilute hydrochloric acid to yield a precipitate. This is filtered and combined with previous solid and is then washed with ether yielding the isothiazolo derivative (9′) (A=N, X=Cl, R=p-F-phenyl).

(g) To a solution of 1.45 g of the preceding isothiazolo-naphthyridine (9′) (A=N, X=Cl, R=p-F-phenyl) in 30 ml pyridine is added in 2.5 ml N-methylpiperazine. It is then heated under nitrogen atmosphere at 40° C. for 8 hours. The mixture is evaporated to dryness and boiled in ethanol for 5 minutes and the mixture is filtered and washed with water yielding the 9-p-fluorophenyl-6-fluoro-7-(4-methyl-1-piperazinyl)-2,3,4,9-tetrahydroisothiazolo[5,4-b][1,8]naphthyridine-3,4-dione (I′) (A=N,

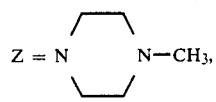

R=p-F-phenyl) m.p. 250° C. This compound can be converted into the hydrochloride salt by suspending it in water and adding in 1N HCl with shaking and warming until dissolved. The resulting solution is evaporated to dryness. The residue is washed with acetonitrile to yield the hydrochloride salt. It can also be converted into a salt in the same manner. For example, to a suspension of it in water is added just enough methansulfonic acid to dissolve with warming. The resulting solution is evaporated to dryness. After washing with acetonitrile, it gives the methanesulfonate salt of the title compound.

(h) Alternately, 9p-fluorophennyl-6-fluoro-7-(4-methyl-1-piperazinyl)-2,3,4,9-tetrahydroisothiazolo[5,4-b][1,8]naphthyridine-3,4-dione (I′) (A=N,

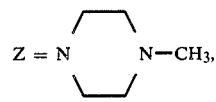

R=p-fluorophenyl) can be prepared as follows: To a solution of 1-6 g of (6′) (product of 2(b)) in 30 ml methylene chloride is added 2.6 ml N-methylpiperazine and the solution is heated at 35° C. for 2 hours. 70 ml of methylene chloride is added and the solution is washed with water (30 ml). The organic poration is dried over magnesium sulfate and the solvent is removed by evaporation under reduced pressure. The residue is dissolved in 5 ml of THF and 25 ml of water is added. The precipitate is filtered yielding 1.72 g of (11′)

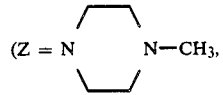

R=p-fluorophenyl, A=N, $R_{13}$=CH$_3$, $R_{12}$=C$_2$H$_3$) m.p. 175° C.

(i) To a solution of 800 mg of the preceding compound (11′) in 10 ml THF is added 3.67 ml of 0.92N sodium hydrosulfide solution. After heating at 65° C. for 19 hours, the solvent is removed by evaporation under reduced pressure. The residue is dissolved in 20 ml H$_2$O and washed with 10 ml methylene chloride. The aqueous portion is acidified with acetic acid to pH 7. The precipitate is collected yielding 750 mg (12′) (A=N, R=p-fluorophenyl,

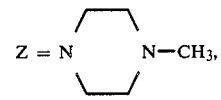

$R_{12}$=C$_2$H$_5$).

(j) To a suspension of 60–0 mg of the preceding compound (12′) in 10 ml THF is added 876 mg sodium bicarbonate in 40 ml of water. After the addition of 588 mg of hydroxylamine-O-sulfonic acid, the mixture is allowed to react for 1¼ hour. The precipitate is filtered yielding 375 mg (I′) (A=N,

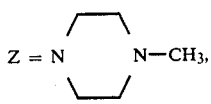

R=p-fluorophenyl).

EXAMPLE 25

9-p-Fluorophenyl-6-fluoro-7-(3-methyl-1-piperazinyl)-2,3,4,9-tetrahydroisothiazolo[5,4-b][1,8]-naphthyridine-3,4-dione The procedure of Example 24 can be repeated, replacing the N-methylpiperazine in 24(g) with 2-methylpiperazine to obtain 9-p-fluorophenyl-6-fluoro-7-(3-methyl-1-piperazinyl)-2,3,4,9-tetrahydroisothiazolo[5,4-b][1,8]naphthyridine-3,4-dione (I') (A=N,

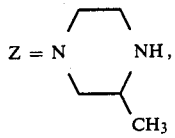

R=p-F-phenyl).

EXAMPLE 26

9-p-Fluorophenyl-6-fluoro-7-(1-piperazinyl)-2,3,4,9-tetrahydroisothiazolo[5,4-b][1,8]naphthyridine-3,4-dione The procedure of Example 24 can be repeated, replacing the N-methylpiperazine in 24(g) with piperazine, one can obtain 9-p-fluorophenyl-6-fluoro-7-(1-piperazinyl)-2,3,4,9-tetrahydrosiothiazolo[5,4-b][1,8]naphthyridine-3,4-dione (I') (A=N,

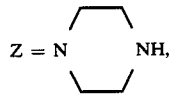

R=p-F-phenyl).

EXAMPLE 27

9-p-Fluorophenyl-6-fluoro-7-(3-t-carbobutoxyamino-1-pyrrolidinyl)-2,3,4,9-tetrahydroisothiazolo[5,4-b][1,8]-naphthyridine-3,4-dione The procedure of Example 24 can be repeated, replacing the N-methylpiperazine in 24(g) with 3-t-(carbobutoxyaminopyrrolidine to obtain 9-p-fluorophenyl-6-fluoro-7-(3-t-carbobutoxyamino-1-pyrrolidinyl)-2,3,4,9-tetrahydroisothiazolo[5,4-b][1,8]naphthyridine-3,4-dione (I') (A=N,

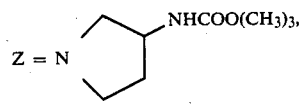

R=p-F-phenyl).

EXAMPLE 28

9-p-Fluorophenyl-6-fluoro-7-(3-amino-1-pyrrolidinyl)-2,3,4,9-tetrahydroisothiazolo[5,4-b][1,8]-naphthyridine-3,4-dione The product of Example 27, I' (A=N, Z=N —NH-COO(CH$_3$)$_3$, R=p-F-phenyl) can be hydrolyzed by the use of a mixture of dilute hydrochloric acid and trifluoroacetic acid to yield 9-p-fluorophenyl-6-fluoro-7-(3-amino-1-pyrrolidinyl)-2,3,4,9-tetrahydroisothiazolo-[5,4-b][1,8]naphthyridine-3,4-dione hydrochloride (I') (A=N,

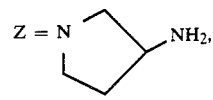

R=p-F-phenyl).

EXAMPLE 29

9-p-Fluorophenyl-6-fluoro-7-(3-amino-4-methyl-1-pyrrolidinyl-2,3,4,9-tetrahydroisothiazolo[5,4-b][1,8]-naphthyridine-3,4-dione The procedure of Example 24 can be repeated, replacing the N-methylpiperazine in 24(g) with 3-amino-4-methyl-pyrrolidine to obtain 9-p-fluorophenyl-6-fluoro-7-(3-amino-4-methyl-1-pyrrolidinyl)-2,3,4,9-tetrahydroisothiazolo[5,4-b][1,8]naphthyridine-3,4-dione (I') (A=N,

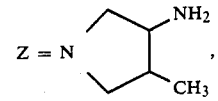

R=p-F-phenyl).

EXAMPLE 30

9-o,p-Difluorophenyl-6-fluoro-7-(4-methyl-1-piperazinyl)-2,3,4,9-tetrahydroisothiazolo[5,4-b][1,8]-naphthyridine-3,4-dione (a) In the described fashion in Example 24(c) replacing methyl N-p-fluorophenyliminochlorothioformate (4A') (R=p-fluorophenyl R$_{13}$=CH$_3$) with methyl N-2,4-difluorophenyliminochlorothioformate (4A') (R=2,4-difluorophenyl R$_{13}$=CH$_3$) one can obtain the naphthyridine derivative (6') (A=N, X=Cl, R$_{12}$=C$_2$H$_5$, R$_{13}$=CH$_3$, R=2,4-difluorophenyl).

(b) By following Examples 24(d), (e) and (f) using the above compound (6') (A=N, X=Cl, R$_{13}$=CH$_3$, R$_{12}$=C$_2$H$_5$, R=2,4-difluorophenyl) instead of compounds (6') in Example 24(d) (A=N, X=Cl, R$_{13}$=CH$_3$, R$_{12}$=C$_2$H$_5$, R=p-F-phenyl) one can obtain the isothiazolo-naphthyridine derivative (9') (A=N, X=Cl, R=2,4-difluorophenyl).

(c) In the described fashion as Example 22(g), the preceding compound (9') (A=N, X=Cl, R=2,4-difluorophenyl) after reacting with N-methylpiperazine one can obtain the desired 9-o,p-difluorophenyl-6-fluoro-7-(4-methyl-1-piperazinyl)-2,3,4,9-tetrahydroisothiazolo[5,4-b][1,8]naphthyridine-3,4-dione (I') (A=N,

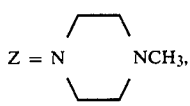

R=2,4-difluorophenyl).

EXAMPLE 31

9-o,p-Difluorophenyl-6-fluoro-7-(3-methyl-1-piperazinyl)-2,3,4,9-tetrahydroisothiazolo[5,4-b][1,8]-naphthyridine-3,4-dione The procedure of Example 30 can be repeated, replacing the N-methylpiperazine in 30(c) with 2-methylpiperazine to obtain 9-o,p-difluorophenyl-6-fluoro-7-(3-methyl-1-piperazinyl)-2,3,4,9-tetrahydroisothiazolo[5,4-b][1,8]-naphthyridine-3,4-dione (I') (A=N,

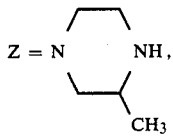

R=o,p-difluorophenyl).

EXAMPLE 32

9-o,p-Difluorophenyl-6-fluoro-7-(1-piperazinyl)-2,3,4,9-tetrahydroisothiazolo[5,4-b][1,8]-naphthyridine-3,4-dione Following the procedure of Example 30, replacing the N-methylpiperazine in 30(c) with piperazine, one can obtain 9-o,p-difluorophenyl-6-fluoro-7-(1-piperazinyl)-2,3,4,9-tetrahydroisothiazolo[5,4-b][1,8]naphthyridine-3,4-dione (I') (A=N,

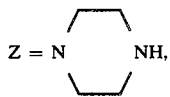

R=2,4-difluorophenyl).

EXAMPLE 33

9-o,p-Difluorophenyl-6-fluoro-7-(3-t-carbobutoxyamino-1-pyrrolidinyl)-2,3,4,9-tetrahydroisothiazolo[5,4-b][1,8]-naphthyridine-3,4-dione In the described fashion as Example 30, replacing N-methylpiperazine in Example 30(c) with 3-t-carbobutoxyaminopyrrolidine, one can obtain 9-o,p-difluorophenyl-6-fluoro-7-(3-t-carbobutoxyamino-1-pyrrolidinyl)-2,3,4,9-tetrahydroisothiazolo[5,4-b][1,8]napthyridine-3,4-dione (I') (A=N,

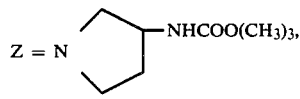

R=2,4-difluorophenyl).

EXAMPLE 34

9-o,p-Difluorophenyl-6-fluoro-7-(3-amino-1-pyrrolidinyl)-2,3,4,9-tetrahydroisothiazolo[5,4-b][1,8]-naphthyridine-3,4-dione The product of Example 33 (I') (A=N, Z=N —NH-COO($CH_3$)$_3$, R=2,4-difluorophenyl) can be hydrolyzed by the use of a mixture of dilute hydrochloric acid and trifluoroacetic acid to give the desired 9-o,p-difluorophenyl-6-fluoro-7-(3-amino-1-pyrrolidinyl)-2,3,4,9-tetrahydroisothiazolo[5,4-b][1,8]naphthyridine-3,4-dione hydrochloride (I') (A=N,

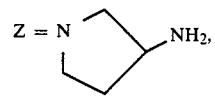

R=2,4-difluorophenyl).

EXAMPLE 35

9-o,p-Difluorophenyl-6-fluoro-7-(3-amino-4-methyl-1-pyrrolidinyl)-2,3,4,9-tetrahydroisothiazolo[5,4-b][1,8]naphthyridine-3,4-dione In the described fashion as Example 30, replacing N-methylpiperazine in Example 30(c) with 3-amino-4-methyl-pyrrolidine, one can obtain 9-o,p-difluorophenyl-6-fluoro-7-(3-amino-4-methyl-1-pyrrolidinyl)-2,3,4,9-tetrahydroisothiazolo[5,4-b][1,8]naphthyridine-3,4-dione (I') (A=N,

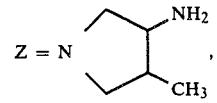

R=2,4-difluorophenyl).

EXAMPLE 36

In the described fashion as Example 24(a and c) replacing the methyl N-p-fluorophenyliminochlorothioformate (4A') (R=p-F-phenyl $R_{13}$=$CH_3$) in 24(c) with an appropriate phenyl N-substituted imino chloroformate (4A') ($R_{13}$=$C_6H_5$) such as R equals to cyclopropyl or ethyl, one can obtain the following compounds.

(a) Ethyl 1-cyclopropyl-2-phenylthio-6-fluoro-7-chloro-1,4-dihydro-4-oxo-1,8-naphthyridine-3-carboxylate (6') (A=N, X=Cl, $R_{12}$=$C_2H_5$, $R_{13}$=$C_6H_5$, R=cyclopropyl)

(b) Ethyl 1-ethyl-2-phenylthio-6-fluoro-7-chloro-1,4-dihydro-4-oxo-1,8-naphthyridine-3-carboxylate (6') (A=N, X=Cl, $R_{12}$=$C_2H_5$, $R_{13}$=$C_6H_5$, R=$C_2H_5$)

EXAMPLE 37

In the described fashion as Example 24(d–g), replacing compound (6') (A=N, X=Cl, $R_{12}$=$C_2H_5$, $R_{13}$=$CH_3$, R=p-fluorophenyl) in Example 24(d) with product of Example 36(a) (Compound (6'), A=N, X=Cl, $R_{12}$=$C_2H_5$, $R_{13}$=$C_6H_5$, R=cyclopropyl) and also replacing N-methylpiperazine in Example 24(g) with an appropriate amine such as N-methylpiperazine, 2-methylpiperazine, 3-t-carbobutoxyamino-pyrrolidine, 3-amino-4-methylpyrrolidine, 3-aminomethyl-4-chloropyrrolidine, thiomorpholine, or piperazine one can obtain the following compounds.

(a) 9-cyclopropyl-6-fluoro-7-(4-methyl-1-piperazinyl)-2,3,4,9-tetrahydroisothiazolo[5,4-b][1,8]naphthyridine-3,4-dione (I') (A=N,

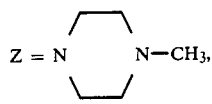

R=cyclopropyl)

(b) 9-cyclopropyl-6-fluoro-7-(3-methyl-1-piperazinyl)-2,3,4,9-tetrahydroisothiazolo[5,4-b][1,8]naphthyridine-3,4-dione (I') (A=N,

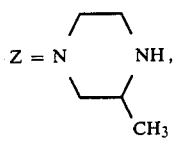

R=cyclopropyl)

(c) 9-cyclopropyl-6-fluoro-7-(3-t-carbobutoxyamino-1-pyrrolidinyl)-2,3,4,9-tetrahydroisothiazolo[5,4-b][1,8]naphthyridine-3,4-dione (I') (A=N,

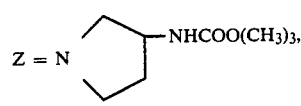

R=cyclopropyl)

(d) 9-cyclopropyl-6-fluoro-7-(3-amino-4-methyl-1-pyrrolidinyl)-2,3,4,9-tetrahydroisothiazolo[5,4-b][1,8]naphthyridine-3,4-dione (I') (A=N,

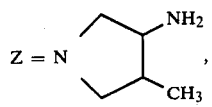

R=cyclopropyl)

(e) 9-cyclopropyl-6-fluoro-7-(1-thiomorpholinyl)-2,3,4,9-tetrahydroisothiazolo[5,4-b][1,8]naphthyridine-3,4-dione (I') (A=N,

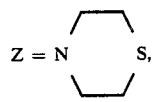

R=cyclopropyl)

(f) 9-cyclopropyl-6-fluoro-7-piperazinyl-2,3,4,9-tetrahydroisothiazolo[5,4-b][1,8]naphthyridine-3,4-dione (I') (A=N,

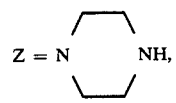

R=cyclopropyl)

(g) 9-cyclopropyl-6-fluoro-7-(3-aminomethyl-4-chloro-1-pyrrolidinyl)-2,3,4,9-tetrahydroisothiazolo[5,4-b][1,8]naphthyridine-3,4-dione (I') (A=N,

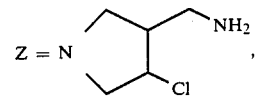

R=cyclopropyl)

EXAMPLE 38

In the same fashion as Example 28, hydrolysis of the compound of Example 37(c) by the use of a mixture of dilute hydrochloric acid and trifluoroacetic acid, one can obtain 9-cyclopropyl-6-fluoro-7-(3-amino-1-pyrrolidinyl)-2,3,4,9-tetrahydroisothiazolo[5,4-b][1,8]naphthyridine-3,4-dione hydrochloride (I') (A=N,

R=cyclopropyl).

EXAMPLE 39

In the described fashion as Example 24(d-g), replacing compound (6') (A=N, X=Cl, $R_{12}=C_2H_5$, $R_{13}=CH_3$, R=p-fluorophenyl) in Example 24(d) with the product of Example 36(b) (Compound (6'), A=N, X=Cl, $R_{12}=C_2H_5$, $R=C_2H_5$), and also using the N-methylpiperazine in Example 24(g) or replacing the N-methylpiperazine with an appropriate amine such as 2-methylpiperazine, 3-t-carbobutoxyaminopyrrolidine, piperazine and 2,2-dimethyl hydrazine, or 3-amino-4-methylpyrrolidine, one can obtain the following compounds.

(a) 9-ethyl-6-fluoro-7-(4-methyl-1-piperazinyl)-2,3,4,9-tetrahydroisothiazolo[5,4-b][1,8]naphthyridine-3,4-dione (I') (A=N,

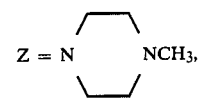

$R=C_2H_5$)

(b) 9-ethyl-6-fluoro-7-(3-methyl-1-piperazinyl)-2,3,4,9-tetrahydroisothiazolo[5,4-b][1,8]naphthyridine-3,4-dione (I') (A=N,

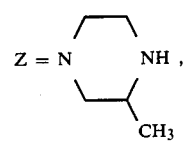

$R=C_2H_5$)

(c) 9-ethyl-6-fluoro-7-(3-t-carbobutoxyamino-1-pyrrolidinyl)-2,3,4,9-tetrahydroisothiazolo[5,4-b][1,8]naphthyridine-3,4-dione (I') (A=N,

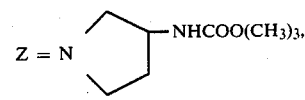

R=cyclopropyl)

(d) 9-ethyl-6-fluoro-7-piperazinyl-2,3,4,9-tetrahydroisothiazolo[5,4-b][1,8]-naphthyridine-3,4-dione (I') (A=N,

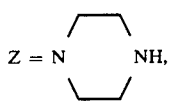

R=$C_2H_5$)

(e) 9-ethyl-6-fluoro-7-(2,2-dimethylhydrazyl)-2,3,4,9-tetrahydroisothiazolo[5,4-b][1,8]-naphthyridine-3,4-dione (I') (A=N, Z=NHN($CH_3$)$_2$, R=$C_2H_5$)

(f) 9-ethyl-6-fluoro-7-(3-amino-4-methyl-1-pyrrolidinyl)-2,3,4,9-tetrahydroisothiazolo[5,4-b][1,8]naphthyridine-3,4-dione (I') (A=N,

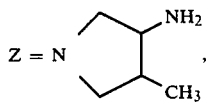

R=$C_2H_5$)

EXAMPLE 40

In the described fashion as Example 26, hydrolysis of Example 37(c) by the use of a mixture of trifluoroacetic acid and dilute hydrochloric acid, one can obtain 9-ethyl-6-fluoro-7-(3-amino-1-pyrrolidinyl)-2,3,4,9-tetrahydroisothiazolo[5,4-b][1,8]naphthyridine-3,4-dione hydrochloride (I') (A=N,

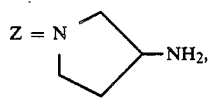

R=$C_2H_5$).

EXAMPLE 41

In the described fashion as Example 24(a), replacing 2,6-dichloro-5-fluoronicotinic acid (1') (A=N, X=Cl) with 2,4,5-trifluorobenzoic acid (1') (A=CH, X=F), 2,3,4,5-tetrafluorobenzoic acid (1') (A=CF, X=F), 3-chloro-2,3,5-trifluorobenzoic acid (1') (A=CCl, X=F), or 3-bromo-2,4,5-trifluorobenzoic acid (2') (A=CBr, X=F), one can obtain the following ketoesters.

(a) Ethyl 2,4,5-trifluorobenzoyl acetate (3') (A=CH, X=F, $R_{12}$=$C_2H_5$)

(b) Ethyl 2,3,4,5-tetrafluorobenzoyl acetate (3) (A=CF, X=F, $R_{12}$=$C_2H_5$)

(c) Ethyl 3-chloro-2,4,5-trifluorobenzoyl acetate (3') (A=CCl, X=F, $R_{12}$=$C_2H_5$)

(d) Ethyl 3-bromo-2,4,5-trifluorobenzoyl acetate (3') (A=CBr, X=F, $R_{12}$=$C_2H_5$)

EXAMPLE 42

By following the Example 24(c), replacing the ketoester (3') (A=N, X=Cl, $R_{12}$=$C_2H_5$) with the ketoester of Example 41(a) and also replacing the methyl N-p-fluorophenyliminochloro-thioformate (4A') (R=p-F-phenyl $R_{13}$=$CH_3$) with an appropriate iminochlorothioformate (4A') such as where R is p-fluorophenyl, 2,4-difluorophenyl, cyclopropyl, ethyl, 4-pyridyl, N-formyl-N-methylamino, 2-methyl-4-pyridyl, 3-chloro-4-pyridyl, 2-pyrazinyl, 3-furyl, p-hydroxyphenyl, or p-methoxy-phenyl, one can obtain the following compounds.

(a) Ethyl 1-p-fluorophenyl-2-methylthio-6,7-difluoro-1,4-dihydro-4-oxo-quinoline-3-carboxylate (6') (A=CH, X=F, $R_{12}$=$C_2H_5$, R=p-fluorophenyl, $R_{13}$=$CH_3$)

(b) Ethyl 1-o,p-difluorophenyl-2-methylthio-6,7-difluoro-1,4-dihydro-4-oxo-quinoline-3-carboxylate (6') (A=CH, X=F, $R_{12}$=$C_2H_5$, R=2,4-difluorophenyl, $R_{13}$=$CH_3$)

(c) Ethyl 1-cyclopropyl-2-methylthio-6,7-difluoro-1,4-dihydro-4-oxo-quinoline-3-carboxylate (6') (A=CH, X=F, $R_{12}$=$C_2H_5$, R=cyclopropyl, $R_{13}$=$CH_3$) m.p. 137.5° C.

(d) Ethyl 1-ethyl-2-methylthio-6,7-difluoro-1,4-dihydro-4-oxo-quinoline-3-carboxylate (6') (A=CH, X=F, $R_{12}$=$C_2H_5$, R=$C_2H_5$, $R_{13}$=$CH_3$) m.p. 113.5° C.

(e) Ethyl 1-(4-pyridyl)-2-methylthio-6,7-difluoro-1,4-dihydro-4-oxo-quinoline-3-carboxylate (6') (A=CH, X=F, $R_{12}$=$C_2H_5$, R=4-pyridyl, $R_{13}$=$CH_3$)

(f) Ethyl 1-N-formyl-N-methylamino-2-methylthio-6,7-difluoro-1,4-dihydro-4-oxo-quinoline-3-carboxylate (6') (A=CH, X=F, $R_{12}$=$C_2H_5$, R=$NCH_3CHO$, $R_{13}$=$CH_3$)

(g) Ethyl 1-(2-methyl-4-pyridyl)-2-methylthio-6,7-difluoro-1,4-dihydro-4-oxo-quinoline-3-carboxylate (6) (A=CH, X=F, $R_{12}$=$C_2H_5$, R=2-methyl-4-pyridyl, $R_{13}$=$CH_3$)

(h) Ethyl 1-(3-chloro-4-pyridyl)-2-methylthio-6,7-difluoro-1,4-dihydro-4-oxo-quinoline-3-carboxylate (6) (A=CH, X=F, $R_{12}$=$C_2H_5$, R=3-chloro-4-pyridyl, $R_{13}$=$CH_3$)

(i) Ethyl 1-(2-pyrazinyl)-2-methylthio-6,7-difluoro-1,4-dihydro-4-oxo-quinoline-3-carboxylate (6') (A=CH, X=F, $R_{12}$=$C_2H_5$, R=2-pyrazinyl, $R_{13}$=$CH_3$)

(j) Ethyl 1-(3-furyl)-2-methylthio-6,7-difluoro-1,4-dihydro-4-oxo-quinoline-3-carboxylate (6) (A=CH, X=F, $R_{12}$=$C_2H_5$, R=3-furyl, $R_{13}$=$CH_3$)

(k) Ethyl 1-(4-hydroxyphenyl)-2-methylthio-6,7-difluoro-1,4-dihydro-4-oxo-quinoline-3-carboxylate (6) (A=CH, X=F, $R_{12}$=$C_2H_5$, R=4-hydroxyphenyl, $R_{13}$=$CH_3$)

(l) Ethyl 1-(4-methoxyphenyl)-2-methylthio-6,7-difluoro-1,4-dihydro-4-oxo-quinoline-3-carboxylate (6) A=CH, X=F, $R_{12}$=$C_2H_5$, R=4-methoxyphenyl, $R_{13}$=$CH_3$)

(m) Ethyl 1-(4-methylphenyl)-2-methylthio-6,7-difluoro-1,4-dihydro-4-oxo-quinoline-3-carboxylate (6) (A=CH, X=F, $R_{12}$=$C_2H_5$, R=4-methylphenyl, $R_{13}$=$CH_3$)

EXAMPLE 43

In the described fashion as Example 24(c), replacing the ketoester (3') (A=N, X=CL, $R_{12}$=$C_2H_5$) with the ketoester of Example 41(b) (3') (A=CF, X=F, $R_{12}$=$C_2H_5$) and also replacing the methyl N-p-fluorophenyliminochlorothioformide (4A') (R=p-F-phenyl, $R_{13}$=$CH_3$) with an appropriate alkyl or phenyl iminochlorothioformate (4A') such as where R is p-fluorophenyl, 2,4-difluorophenyl, cyclopropyl, ethyl, 3,4-methylenedioxyphenyl, or 2,4,6-trifluorophenyl, one can obtain the following compounds.

(a) Ethyl 1-p-fluorophenyl-2-methylthio-6,7,8-trifluoro-1,4-dihydro-4-oxo-quinoline-3-carboxylate (6')

(A=CF, X=F, $R_{12}$=C$_2$H$_5$, R=p-fluorophenyl, $R_{13}$=CH$_3$)

(b) Ethyl 1-o,p-difluorophenyl-2-methylthio-6,7,8-trifluoro-1,4-dihydro-4-oxo quinoline-3-carboxylate (6') (A=CF, X=F, $R_{12}$=C$_2$H$_5$, $R_{13}$=CH$_3$, R=2,4-difluorophenyl)

(c) Ethyl 1-cyclopropyl-2-phenylthio-6,7,8-trifluoro-1,4-dihydro-4-oxo quinoline-3-carboxylate (6')(A=CF, X=F, $R_{12}$=C$_2$H$_5$, R=cyclopropyl, CH$_3$=CH$_6$H$_5$) m.p. 135°–137° C.)

(d) Ethyl 1-ethyl-2-phenylthio-6,7,8-trifluoro-1,4-dihydro-4-oxo-quinoline-3-carboxylate (6')(A=CF, X=F, $R_{12}$=C$_2$H$_5$, R=C$_2$H$_5$, $R_{13}$=C$_6$H$_5$ m.p. 91° C.)

(e) Ethyl 1-(3',4'-methylenedioxyphenyl)-2-methylthio-6,7,8-trifluoro-1,4-dihydro-4-oxo-quinoline-3-carboxylate (6')(A=CF, X=F, $R_{12}$=C$_2$H$_5$, $R_{13}$=CH$_3$, R=3,4-methylenedioxyphenyl)

(f) Ethyl 1-(2',4',6'-trifluorophenyl)-2-methylthio-6,7,8-trifluoro-1,4-dihydro-4-oxo-quinoline-3-carboxylate (6') (A=CF, X=F, $R_{12}$=C$_2$H$_5$, $R_{13}$=CH$_3$, R=2,4,6-trifluorophenyl)

EXAMPLE 44

By following the Example 24(c), replacing the ketoester (3') (A=N, X=Cl, $R_{12}$=C$_2$H$_5$) with the ketoester of Example 41(c) and also replacing the methyl N-p-fluorophenyliminochloro-thioformate (4A') (R=p-F-phenyl $R_{13}$=CH$_5$) with an appropriate alkyl or phenyl iminochlorothioformate (4A') such as R equals to p-fluorophenyl, 2,4-difluorophenyl, cyclopropyl, ethyl, one can obtain the following compounds.

(a) Ethyl 1-p-fluorophenyl-1-methylthio-6,7-difluoro-8-chloro-1,4-dihydro-4-oxo-quinoline-3-carboxylate (6') (A=CCl, X=F, $R_{12}$=C$_2$H$_5$, R=p-fluorophenyl $R_{13}$=CH$_3$)

(b) Ethyl 1-o,p-difluorophenyl-2-methylthio-6,7-difluoro-8-chloro-1,4-dihydro-4-oxo-quinoline-3-carboxylate (6') (A=CCl, X=F, $R_{12}$=C$_2$H$_5$, R=2,4-difluorophenyl, $R_{13}$=CH$_3$)

(c) Ethyl 1-cyclopropyl-2-phenylthio-6,7-difluoro-8-chloro-1,4-dihydro-4-oxo-quinoline-3-carboxylate (6) (A=CCl, X=F, $R_{12}$=C$_2$H$_5$, R=cyclopropyl, $R_{13}$=C$_6$H$_5$)

(d) Ethyl 1-ethyl-2-phenylthio-6,7-difluoro-8-chloro-1,4-dihydro-4-oxo-quinoline-3-carboxylate (6') (A=CCl, X=F, $R_{12}$=C$_2$H$_5$, R=C$_2$H$_5$, $R_{13}$=C$_6$H$_5$)

EXAMPLE 45

By following the Example 24(c), replacing the ketoester (3') (A=N, X=Cl, $R_{12}$=C$_2$H$_5$) with the ketoester of example 41(d) and also replacing the methyl N-p-fluorophenyliminochloro-thioformate (4A') (R=p-F-phenyl $R_{13}$CH$_3$) with an appropriate methyl or phenyl iminochlorothioformate (4A') such as where R is p-fluorophenyl, 2,4-difluorophenyl, cyclopropyl, or ethyl, one can obtain the following compounds.

(a) Ethyl 1-p-fluorophenyl-2-methylthio-6,7-difluoro-8-bromo-1,4-dihydro-4-oxo-quinoline-3-carboxylate (6') (A=CBr, X=F, $R_{12}$=C$_2$H$_5$, R=p-fluorophenyl, $R_{13}$=CH$_3$)

(b) Ethyl 1-o,p-difluorophenyl-2-methylthio-6,7-difluoro-8-bromo-1,4-dihydro-4-oxo-quinoline-3-carboxyate (6') (A=CBr, X=F, $R_{12}$=C$_2$H$_5$, R=2,4-difluorophenyl, $R_{13}$=CH$_3$)

(c) Ethyl 1-cyclopropyl-2-phenylthio-6,7-difluoro-8-bromo-1,4-dihydro-4-oxo-quinoline-3-carboxylate (6) (A=CBr, X=F, $R_{12}$=C$_2$H$_5$, R=cyclopropyl, $R_{13}$=C$_6$H$_5$)

(d) Ethyl 1-ethyl-2-methylthio-6,7-difluoro-8-bromo-1,4-dihydro-4-oxo-quinoline-3-carboxylate (6') (A=CBr, X=F, $R_{12}$=C$_2$H$_5$, R=C$_2$H$_5$, $R_{13}$=C$_6$H$_5$)

EXAMPLE 46

In the described fashion as Example 24(d–g), replacing compound (6') (A=N, X=Cl, $R_{12}$=C$_2$H$_5$, , $R_{13}$=CH$_3$, R=p-fluorophenyl) in Example 24(d), with compound (6') of Examples 42(a–m), 43(a–f), 44(a–d) and 45(a–d) and also replacing N-methylpiperazine in Example 24(g) with an appropriate amine such as N-methylpiperazine, 2-methylpiperazine, 3-t-carbobutoxyaminopyrrolidine, 3-amino-4-methyl-pyrrolidine, piperidine, ethylamine, ethanolamine, 1,2-diaminoethane, N-methylhydrazine, N,N-dimethylhydrazine, 3-ethylaminomethylpyrrolidine, 3-hydroxymethyl-1-pyrrolidine, 3-methylaminopyrrolidine, 2-p-fluorophenylpiperazine, 2-phenylpiperazine, pyrrolidine, 3-hydroxypyrrolidine, 3-aminomethyl-4-chloropyrrolidine, homopiperazine, morpholine, thiomorpholine, piperazine 3-amino-3-methylpyrrolidine and 3-aminomethyl-1-pyrrolidine, one can obtain the following compounds.

(a) 9-p-fluorophenyl-6-fluoro-7-(4-methyl-1-piperazinyl)-2,3,4,9-tetrahydroisothiazolo[5,4-b]quinoline-3,4-dione (I') (A=CH,

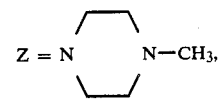

R=p-fluorophenyl) m.p. 269°–270° C. (with decomposition)

(b) 9-p-fluorophenyl-6-fluoro-7-(3-methyl-1-piperazinyl)-2,3,4,9-tetrahydroisothiazolo[5,4-b]quinoline-3,4-dione (I') (A=CH,

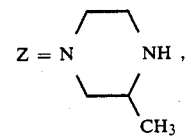

R=p-fluorophenyl) m.p. 268°–269° C. (with decomposition).

(c) 9-p-fluorophenyl-6-fluoro-7-(3-t-carbobutoxyamino-1-pyrrolidinyl)-2,3,4,9-tetrahydroisothiazolo[5,4-b]quinoline-3,4-dione(I'). (A=CH,

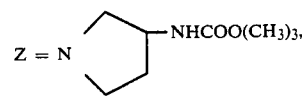

R=p-fluorophenyl)

(d) 9-p-fluorophenyl-6-fluoro-7-(3-amino-4-methyl-1-pyrrolidinyl)-2,3,4,9-tetrahydroisothiazolo[5,4-b]quinoline-3,4-dione(I'). (A=CH,

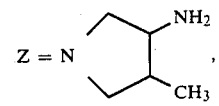

R=p-fluorophenyl)

(e) 9-o,p-difluorophenyl-6-fluoro-7-(4-methyl-1-piperazinyl)-2,3,4,9-tetrahydroisothiazolo[5,4-b]quinoline-3,4-dione(I')(A=CH,

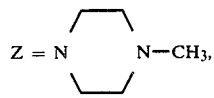

R=o,p-difluorophenyl)

(f) 9-o,p-difluorophenyl-6-fluoro-7-(3-methyl-1-piperazinyl)-2,3,4,9-tetrahydroisothiazolo[5,4-b]quinoline-3,4-dione (I')(A=CH,

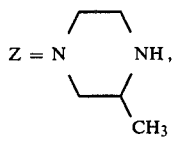

R=o,p-difluorophenyl)

(g) 9-o,p-difluorophenyl-6-fluoro-7-(3-amino-4-methyl-1-pyrrolidinyl)-2,3,4,9-tetrahydroisothiazolo[5,4-b]quinoline-3,4-dione (I') (A=CH,

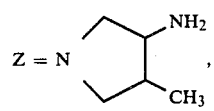

R=o,p-difluorophenyl)

(h) 9-cyclopropyl-6-fluoro-7-(4-methyl-1-piperazinyl)-2,3,4,9-tetrahydroisothiazolo[5,4-b]quinoline-3,4-dione (I') (A=CH,

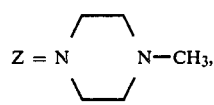

R=cyclopropyl) m.p. 270° C.

(i) 9-cyclopropyl-6-fluoro-7-(3-methyl-1-piperazinyl)-2,3,4,9-tetrahydroisothiazolo[5,4-b]quinoline-3,4-dione(I') (A=CH,

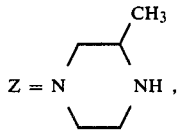

R=cyclopropyl) m.p. 250°-251° C. (with decomposition )

(j) 9-cyclopropyl-6-fluoro-7-(3-amino-4-methyl-1-pyrrolidinyl)2,3,4,9-tetrahydroisothiazolo[5,4-b]quinoline-3,4-dione (I') (A=CH,

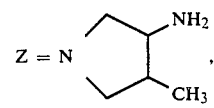

R=cyclopropyl)

(k) 9-cyclopropyl-6-fluoro-7-morpholinyl-2,3,4,9-tetrahydroisothiazolo[5,4-b]quinoline-3,4-dione (I') (A=CH,

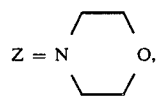

R=cyclopropyl)

(l) 9-ethyl-6-fluoro-7-(4-methyl-1-piperazinyl)-2,3,4,9-tetrahydroisothiazolo[5,4-b]quinoline-3,4-dione (I') (A=CH,

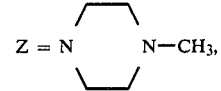

R=$C_2H_5$) and its hydrochloride salt m.p. >270° C.

(m) 9-ethyl-6-fluoro-7-(1-piperazinyl)-2,3,4,9-tetrhydroisothiazolo[5,4-b]quinoline-3,4-dione (I') (A=CH,

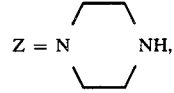

R=$C_2H_5$) and its hydrochloride salt m.p. >270° C.

(n) 9-cyclopropyl-6-fluoro-7-(3-t-carbobutoxyamino-1-pyrrolidinyl)-2,3,4,9-tetrahydroisothiazolo[5,4-b]quinoline-3,4-dione(I') (A=CH,

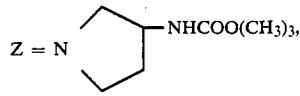

R=cyclopropyl)

(o) 9-ethyl-6-fluoro-7-(1-piperidinyl)-2,3,4,9-tetrahydroisothiazolo[5,4-b]quinoline-3,4-dione (I') (A=CH,

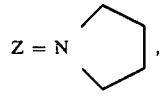

R=$C_2H_5$)

(p) 9-(4-pyridyl)-6-fluoro-7-(4-methyl-1-piperazinyl)-2,3,4,9-tetrahydroisothiazolo[5,4-b]quinoline-3,4-dione(I') (A=CH,

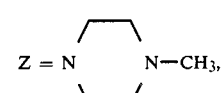

R=4-pyridyl)

(q) 9-(N-formyl-N-methylamino)-6-fluoro-7-(4-methyl-1-piperazinyl)-2,3,4,9-tetrahydroisothiazolo[5,4-b]quinoline-3,4-dione(I') (A=CH,

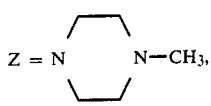

R=NCH₃CHO)
(r) 9-p-fluorophenyl-6,8-difluoro-7-(4-methyl-1-piperazinyl)-2,3,4,9-tetrhydroisothiazolo[5,4-b]quinoline-3,4-dione(I') (A=CF,

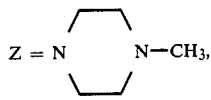

R=p-fluorophenyl)
(s) 9-p-fluorophenyl-6,8-difluoro-7-(1-piperazinyl)-2,3,4,9-tetrahydroisothiazolo[5,4-b]quinoline-3,4,-dione(I') (A=CF,

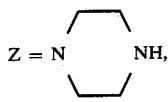

R=p-fluorophenyl)
(t) 9-p-fluorophenyl-6,8-difluoro-7-(3-amino-4-methyl-1-pyrrolidinyl)-2,3,4,9-tetrahydroisothiazolo[5,4-b]quinoline-3,4-dione (I') (A=CF,

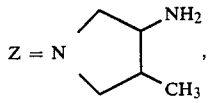

R=p-fluorophenyl)
(u) 9-p-fluorophenyl-6,8-difluoro-7-pyrrolidinyl-2,3,4,9-tetrahydroisothiazolo[5,4-b]quinoline-3,4-dione (I') (A=CF,

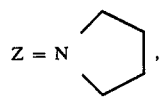

R=p-fluorophenyl)
(v) 9-o,p-difluorophenyl-6,8-difluoro-7-(4-methyl-1-piperazinyl)-2,3,4,9-tetrahydroisothiazolo[5,4-b]quinoline-3,4-dione (I') (A=CF,

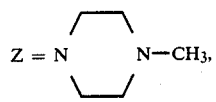

R=2,4-difluorophenyl)
(w) 9-o,p-difluorophenyl-6,8-difluoro-7-(3-methyl-1-piperazinyl)-2,3,4,9-tetrahydroisothiazolo[5,4-b]quinoline-3,4-dione(I') (A=CF,

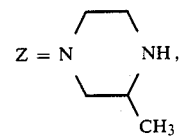

R=2,4-difluorophenyl)
(x) 9-o,p-difluorophenyl-6,8-difluoro-7-(3-t-carbobutoxyamino-1-pyrrolidinyl)-2,3,4,9-tetrahydroisothiazolo[5,4-b]quinoline-3,4-dione (I') (A=CF,

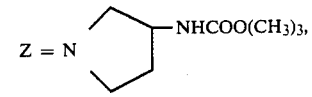

R=2,4-difluorophenyl)
(y) 9-cyclopropyl-6,8-difluoro-7-(4-methyl-1-piperazinyl)-2,3,4,9-tetrahydroisothiazolo[5,4-b]quinoline-3,4-dione (I') (A=CF,

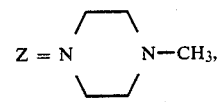

R=cyclopropyl) and its hydrochloride and methanesulfonate salt m.p. >270° C.
(z) 9-cyclopropyl-6,8-difluoro-7-(3-methyl-1-piperazinyl)-2,3,4,9-tetrahydroisothiazolo[5,4-b]quinoline-3,4-dione (I') (A=CF,

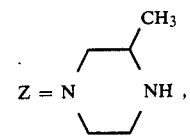

R=cyclopropyl and its methanesulfonate salt, m.p. >270° C.)
(aa) 9-cyclopropyl-6,8-difluoro-7-(3-t-carbobutoxyamino-1-pyrrolidinyl)-2,3,4,9-tetrahydroisothiazolo[5,4-b]quinoline-3,4-dione (I') (A=CF,

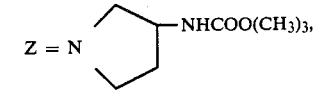

R=cyclopropyl)
(bb) 9-cyclopropyl-6,8-difluoro-7-thiomorpholinyl-2,3,4,9-tetrahydroisothiazolo[5,4-b]quinoline-3,4-dione (I') (A=CF,

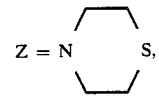

R=cyclopropyl)
(cc) 9-ethyl-6,8-difluoro-7-(4-methyl-1-piperazinyl)-2,3,4,9-tetrahydroisothiazolo[5,4-b]quinoline-3,4-dione (I') (A=CF,

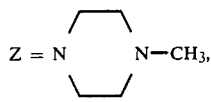

R=C₂H₅) and its methanesulfonate salt, m.p. >270° C.

(dd) 9-ethyl-6,8-difluoro-7-(piperazinyl)-2,3,4,9-tetrahydroisothiazolo[5,4-b]quinoline-3,4-dione (I'), (A=CF,

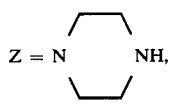

R=C₂H₅) and its methane-sulfonate salt, m.p. >270° C.

(ee) 9-ethyl-6,8-difluoro-7-(3-amino-4-methyl-1-pyrrolidinyl)-2,3,4,9-tetrahydroisothiazolo[5,4-b]quinoline-3,4-dione (I'), (A=CF,

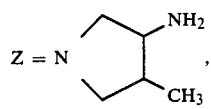

R=C₂H₅) and its methanesulfonate salt, m.p. >270° C.

(ff) 9-(3',4'-methylenedioxyphenyl)-6,8-difluoro-7-(4-methyl-1-piperazinyl)-2,3,4,9-tetrahydroisothiazolo[5,4-b]quinoline-3,4-dione (I') (A=CF,

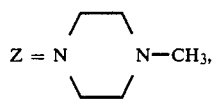

R=3,4-methylenedioxyphenyl (gg) 9-(2',4',6'-trifluorophenyl)-6,8-difluoro-7-(4-methyl-1-piperazinyl)-2,3,4,9-tetrahydroisothiazolo[5,4-b]quinoline-3,4-dione (I') (A=CF,

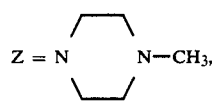

R=2,4,6-trifluorophenyl)

(hh) 9-cyclopropyl-6-fluoro-7-(1-piperidinyl)-2,3,4,9-tetrahydroisothiazolo[5,4-b]quinoline-3,4-dione (I') (A=CH,

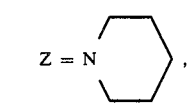

R=cyclopropyl)

(ii) 9-cyclopropyl-6-fluoro-7-(3-aminomethyl-1-pyrrolidinyl)-2,3,4,9-tetrahydroisothiazolo[5,4-b]quinoline-3,4-dione (I') (A=CH,

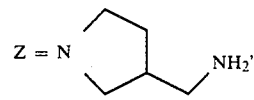

R=cyclopropyl)

(jj) 9-(2-methyl-4-pyridyl)-6-fluoro-7-ethylamino-2,3,4,9-tetrahydroisothiazolo[5,4-b]quinoline-3,4-dione (I') (A=CH, Z=NHC₂H₅, R=2-methyl-4-pyridyl)

(kk) 9-(3-chloro-4-pyridyl)-6-fluoro-7-hydroxyethalamino-2,3,4,9-tetrahydroisothiazolo[5,4-b]quinoline-3,4-dione (I') (A=CH, Z=NHC₂H₄OH, R=3-chloro-4-pyridyl)

(ll) 9-(2-pyrazinyl)-6-fluoro-7-aminoethylamino-2,3,4,9-tetrahydroisothiazolo[5,4-b]quinoline-3,4-dione (I'). (A=CH, Z=NHC₂H₄NH₂, R=2-pyrazinyl)

(mm) 9-(3-furyl)-6-fluoro-7-(2-methyl-1-hydrazyl)-2,3,4,9-tetrahydroisothiazolo[5,4-b]quinoline-3,4-dione (I'). (A=CH, Z=NHNHCH₃, R=3-furyl)

(nn) 9-(4-hydroxyphenyl)-6-fluoro-7-(2,2-dimethyl-1-hydrazyl)-2,3,4,9-tetrahydroisothiazolo[5,4-b]quinoline-3,4-dione (I') (A=CH, Z=NHN(CH₃)₂, R=4-hydroxyphenyl)

(oo) 9-(4-methoxyphenyl)-6-fluoro-7-(3-hydroxymethyl-1-pyrrolidinyl)-2,3,4,9-tetrahydroisothiazolo[5,4-b]quinoline-3,4-dione (I'). (A=CH,

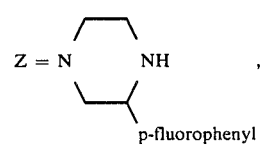

R=4-methoxyphenyl)

(pp) 9-cyclopropyl-6-fluoro-7-(3-methyl-3-amino-1-pyrrolidinyl)-2,3,4,9-tetrahydroisothiazolo[5,4-b]quinoline-3,4-dione (I'). (A=CH, R=cyclopropyl) and its methanesulfonate salt, m.p. >270° C.

(qq) 9-cyclopropyl-6-fluoro-7-(3-p-fluorophenyl-1-piperazinyl)-2,3,4,9-tetrahydroisothiazolo[5,4-b]quinoline-3,4-dione (I'), (A=CH, R=cyclopropyl)

(rr) 9-cyclopropyl-6-fluoro-7-(3-phenyl-1-piperazinyl)-2,3,4,9-tetrahydroisothiazolo[5,4-b]quinoline-3,4-dione (I'). (A=CH,

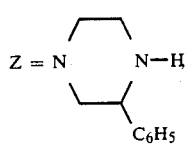

R-cyclopropyl)

(ss) 9-cyclopropyl-6-fluoro-7-(3-hydroxy-1-pyrrolidinyl)-2,3,4,9-tetrahydroisothiazolo[5,4-b]quinoline-3,4-dione (I'). (A=CH,

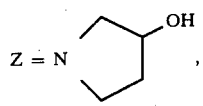

R=cyclopropyl) m.p. >270° C.

(tt) 9-cyclopropyl-6-fluoro-7-(3-aminomethyl-4-chloro-1-pyrrolidinyl)-2,3,4,9-tetrahydroisothiazolo[5,4-b]quinoline-3,4-dione (I'). (A=CH,

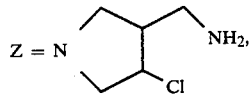

R=cyclopropyl)

(uu) 9-cyclopropyl-6-fluoro-7-(1-homopiperazinyl)-2,3,4,9-tetrahydroisothiazolo[5,4-b]quinoline-3,4-dione (I'). (A=CH,

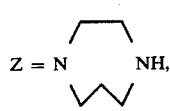

R=cyclopropyl)

(vv) 9-(4-methylphenyl)-6-fluoro-7-(1-piperazinyl)-2,3,4,9-tetrahydroisothiazolo[5,4-b]quinoline-3,4-dione (I'). (A=CH,

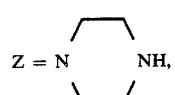

R=4-methylphenyl)

(ww) 9-ethyl-6-fluoro-7-(3-methyl-1-piperazinyl)-2,3,4,9-tetrahydroisothiazolo[5,4-b]quinoline-3,4-dione (I') (A=CH,

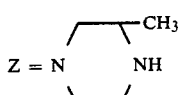

R=C$_2$H$_5$) and its hydrochloride salt, m.p. >270° C.

(xx) 9-ethyl-6,8-difluoro-7-(3-methyl-1-piperazinyl)-2,3,4,9-tetrahydroisothiazolo[5,4-b]quinoline-3,4-dione (I') (A=CF,

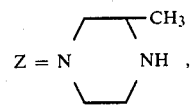

R=C$_2$H$_5$) and its methanesulfonate salt, m.p. >270° C.

(yy) 9-p-fluorophenyl-6-fluoro-7-(1-piperozinyl)-2,3,4,9-tetrahydroisothiazolo[5,4-b]quinoline-3,4-dione (I') (A=CH,

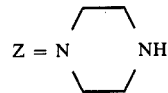

R=p-fluorophenyl), m.p. 251°-252° C. (with decomposition)

(zz) 9-cyclopropyl-6-fluoro-7-(1-piperazinyl)-2,3,4,9-tetrahydroisothiazolo[5,4-b]quinoline-3,4-dione (I') and its hydrochloride and methanesulfonate salt (A=CH,

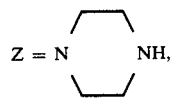

R=cyclopropyl), m.p. >270° C.

(aaa) 9-cyclopropyl-6-fluoro-7-(3-t-carbobutoxyamino-1-pyrrolidinyl)-2,3,4,9-tetrahydroisothiazolo[5,4-b]quinoline-3,4-dione (I') (A=CH,

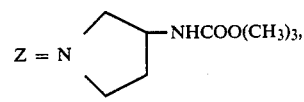

R=cyclopropyl)

(bbb) 9-ethyl-6-fluoro-7-(1-pyrrolidinyl)-2,3,4,9-tetrahydroisothiazolo[5,4-b]quinoline-3,4-dione (I') (A=CH,

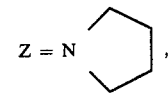

R=ethyl), m.p. >270° C.

(ccc) 9-cyclopropyl-6,8-difluoro-7-(1-piperazinyl)-2,3,4,9-tetrahydroisothiazolo[5,4-b]quinoline-3,4-dione (I') (A=CF,

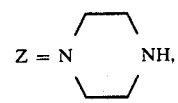

R=cyclopropyl) and its hydrochloride and methanesulfonate salt, m.p. >270° C.

(ddd) 9-cyclopropyl-6,8-difluoro-7-(3-amino-4-methyl-1-pyrrolidinyl)-2,3,4,9-tetrahydroisothiazolo[5,4-b]quinoline-3,4-dione (I') (A=CF,

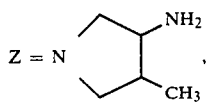

R=cyclopropyl) and its methanesulfonate salt, m.p. >270° C.

(eee) 9-cyclopropyl-6,8-difluoro-7-(3-ethylaminomethyl-1-pyrrolidinyl)-2,3,4,9-tetrahydroisothiazolo[5,4-b]quinoline-3,4-dione (I') (A=CF,

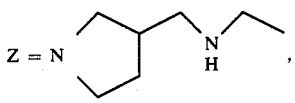

R=cyclopropyl) and its methanesulfonate salt, m.p. >270° C.

(fff) 9-ethyl-6,8-difluoro-7-(3-t-carbobutoxyamino-1-pyrrolidinyl)-2,3,4,9-tetrahydroisothiazolo[5,4-b]quinoline-3,4-dione (I') (A=CF,

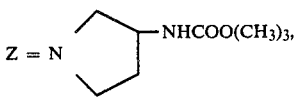

R=ethyl)

(ggg) 9-ethyl-6,8-difluoro-7-(3-ethylaminomethyl-1-pyrrolidinyl)-2,3,4,9-tetrahydroisothiazolo[5,4-b]quinoline-3,4-dione (I') (A=CF,

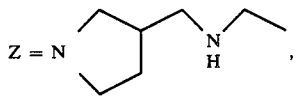

R=ethyl) and its methanesulfonate salt, m.p. >270° C.

(hhh) 9-p-fluorophenyl-6-fluoro-8-chloro-7-(4-methyl-1-piperazinyl)-2,3,4,9-tetrahydroisothiazolo[5,4-b]qquinoline-3,4-dione (I') (A=CCl,

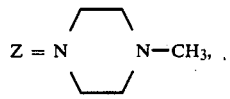

R=p-fluorophenyl)

(iii) 9-p-fluorophenyl-6-fluoro-8-chloro-7-3-methyl-1-piperazinyl)-2,3,4,9-tetrahydroisothiazolo[5,4-b]quinoline,3,4-dione (I') (A=CCl,

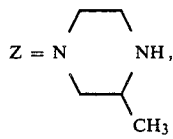

R=p-fluorophenyl)

(jjj) 9-p-fluorophenyl-6-fluoro-8-chloro-7-(3-t-carbobutoxyamino-1-pyrrolidinyl)-2,3,4,9-tetrahydroisothiazolo[5,4-b]quinoline-3,4-dione (I') (A=CCl,

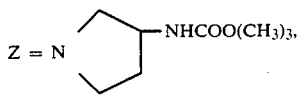

R=p-fluorophenyl)

(kkk) 9-o,p-difluorophenyl-6-fluoro-8-chloro-7-(4-methyl-1-piperazinyl)-2,3,4,9-tetrahydroisothiazolo[5,4-b]quinoline-3,4-dione (I') (A=CCl,

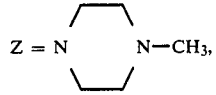

R=o,p-difluorophenyl)

(lll) 9-o,p-difluorophenyl-6-fluoro-8-chloro-7-(3-methyl-1-(piperazinyl)-2,3,4,9-tetrahydroisothiazolo[5,4-b]quinoline-3,4-dione (I') (A=CCl,

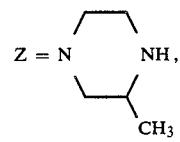

R=o,p-difluorophenyl)

(mmm) 9-cyclopropyl-6-fluoro-8-chloro-(4-methyl-1-piperazinyl)-2,3,4,9-tetrahydroisothiazolo[5,4-b]quinoline-3,4-dione (I') (A=Cl,

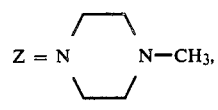

R=cyclopropyl) and its methanesulfonate salt m.p. >270° C.

(nnn) 9-cyclopropyl-6-fluoro-8-chloro-7-(3-methyl-1-piperazinyl)-2,3,4,9-tetrahydroisothiazolo[5,4-b]quinoline-3,4-dione (I') (A=Cl,

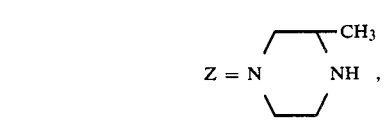

R=cyclopropyl) and its methanesulfonate salt, m.p. 270° C.

(ooo) 9-cyclopropyl-6-fluoro-8-chloro-7-(3-amino-4-methyl-1-pyrrolidinyl)-2,3,4,9-tetrahydroisothiazolo[5,4-b]quinoline-3,4-dione (I') (A=CH,

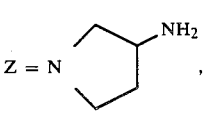

R=cyclopropyl) and its hydrochloride salt, m.p. >270° C.

(ppp) 9-cyclopropyl-6-fluoro-8-chloro-7-(3-t-carbobutoxyamino-1-pyrrolidinyl)-2,3,4,9-tetrahydroisothiazolo[5,4-b]quinoline-3,4-dione (I') (A=CCl,

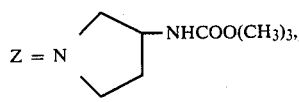

R=cyclopropyl)

(qqq) 9-cyclopropyl-6-fluoro-8-chloro-7-(3-ethylaminomethyl-1-pyrrolidinyl)-2,3,4,9-tetrahydroisothiazolo[5,4-b]quinoline-3,4-dione (I') (A=CCl,

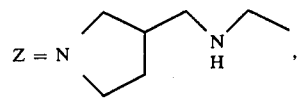

R=cyclopropyl)

(rrr) 9-ethyl-6-fluoro-8-chloro-7-(3-t-carbobutoxyamino-1-pyrrolidinyl)2,3,4,9-tetrahydroisothiazolo[5,4-b]quinoline-3,4-dione (I') (A=CCl,

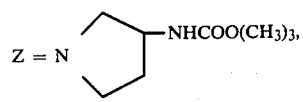

R=C₂H₅)

(sss) 9-ethyl-6-fluoro-8-chloro-7-(1-piperazinyl)2,3,4,9-tetrahydroisothiazolo[4,5-b]quinoline-3,4-dione (I') (A=CCl,

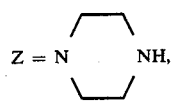

R=ethyl)

(ttt) 9-cyclopropyl-6-fluoro-8-bromo-7-(3-t-carbobutoxyamino-1-pyrrolidinyl)-2,3,4,9-tetrahydroisothiazolo[5,4-b]quinoline-3,4-dione (I') (A=CBr,

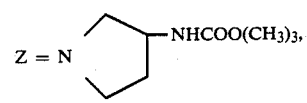

R=cyclopropyl)

EXAMPLE 47

In the described fashion as Example 28, hydrolysis of Examples 46(c), (n), (q), (x), (aa), (aaa), (fff), (jjj), (ppp), (rrr), and (ttt) by the use of a mixture of trifluoro acetic acid and dilute hydrochloric acid, one can obtain the following compounds as hydrochloride salts. The melting points for these compounds are >270° C.

(a) 9-p-fluorophenyl-6-fluoro-7-(3-amino-1-pyrrolidinyl)-2,3,4,9-tetrahydroisothiazolo[5,4-b]quinoline-3,4-dione hydrochloride (I') (A=CH,

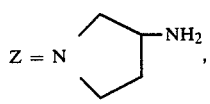

R=p-fluorophenyl)

(b) 9-cyclopropyl-6-fluoro-7-(3-amino-1-pyrrolidinyl)-2,3,4,9-tetrahydroisothiazolo[5,4-b]quinoline-3,4-dione hydrochloride (I') (A=CH,

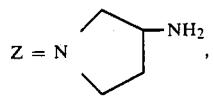

R=cyclopropyl)

(c) 9-methylamino-6-fluoro-7-(1,4-methylpiperazinyl)-2,3,4,9-tetrahydroisothiazolo[5,4-b]quinoline-3,4-dione hydrochloride (I') (A=CH,

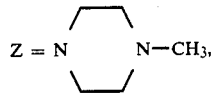

ps R=NHCH₃)

(d) 9-o,p-difluorophenyl-6,8-difluoro-7-(1-3-aminpyrrolidinyl)-2,3,4,9-tetrahydroisothiazolo[5,4-b]quinoline-3,4-dione hydrochloride (I') (A=CF,

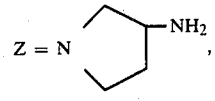

R=2,4-difluorophenyl)

(e) 9-cyclopropyl-6,8-difluoro-7-(1-3-aminopyrrolidinyl)-2,3,4,9-tetrahydroisothiazolo[5,4-b]quinoline-3,4-dione hydrochloride (I') (A=CF,

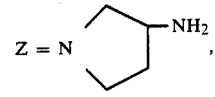

R=cyclopropyl)

(f) 9-cyclopropyl-6-fluoro-7-(3-amino-1-pyrrolidinyl)-2,3,4,9-tetrahydroisothiazolo,[5,4-b]quinoline-3,4-dione (I') (A=CH,

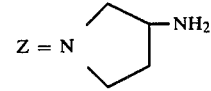

R=cyclopropyl)

(g) 9-ethyl-6,8-difluoro-7-(3-amino-1-pyrrolidinyl)-2,3,4,9-tetrahydroisothiazolo[5,4-b]quinoline-3,4-dione (I') (A=CF,

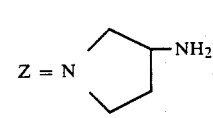

R=ethyl)

(h) 9-p-fluorophenyl-6-fluoro-8-chloro-7-(3-amino-1-pyrrolidinyl)-2,3,4,9-tetrahydroisothiazolo[5,4-b]quinoline-3,4-dione (I') (A=CCl,

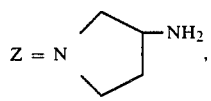

R=p-fluorophenyl)

(i) 9-cyclopropyl-6-fluoro-8-chloro-7-(3-amino-1-pyrrolidinyl)-2,3,4,9-tetrahydroisothiazolo[5,4-b]quinoline-3,4-dione (I') (A=CCl,

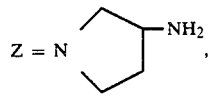

R-cyclopropyl)

(j) 9-ethyl-6-fluoro-8-chloro-7-(3-amino-1-pyrrolidinyl)-2,3,4,9-tetrahydroisothiazolo[5,4-b]quinoline-3,4-dione (I') (A-CCl,

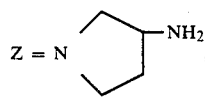

R-ethyl)

(k) 9-cyclopropyl-6-fluoro-8-bromo-7-(3-amino-1-pyrrolidinyl)-2,3,4,9-tetrahydroisothiazolo[5,4-b]quinoline-3,4-dione (I') (A=CBr,

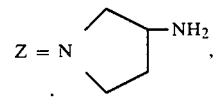

R=cyclopropyl)

EXAMPLE 48

The antimicrobial activities of a few representative compounds of this invention are given in Table 1. The in vitro antibacterial activity is determined by conventional agar dilution procedures. A brain-heart infusion agar medium containing the drug is inoculated with a microbial culture cultivated on a brain-infusion broth (Difco 0037-01-6) at 36° C. for 18 hours and then observes for growth of the microorganism. The minimum concentration at which growth of the microorganism is inhibited is taken as MIC (ug/ml). The inoculum size is $10^4$/plate.

TABLE 1

MIC (μg/ml)

| Organism | Compound of Example | | | | | | | |
|---|---|---|---|---|---|---|---|---|
| | 46(a) | 46(b) | 46(g) | 46(l) | 46(m) | 46(ww) | 46(xx) | 46(yy) |
| Stap. aureus ATCC-6538p | 0.01 | 0.01 | 0.05 | 0.05 | 0.1 | 0.05 | 0.1 | 0.1 |
| Stap. epidermis 3519 | 0.2 | 0.2 | 0.1 | 0.1 | 0.2 | 0.1 | 0.2 | 0.2 |
| Ent. faecium ATCC 8043 | 1.56 | 0.78 | 0.2 | 0.2 | 0.39 | 0.78 | 0.78 | 0.78 |
| Strep. Pyogenes EES61 | 1.56 | 0.78 | 0.78 | 0.39 | 0.2 | 0.78 | 0.39 | 0.78 |
| E. coli Juhl | 0.2 | 0.05 | 0.05 | 0.05 | 0.1 | 0.1 | 0.05 | 0.05 |
| Ent. aerogenes ATCC 13048 | 0.39 | 0.02 | 0.1 | 0.1 | 0.2 | 0.1 | 0.1 | 0.1 |
| K. pneumoniae ATCC 8045 | 0.1 | 0.01 | 0.1 | 0.05 | 0.05 | 0.2 | 0.005 | 0.02 |
| P. stuartii CMX 640 | 12.5 | 6.2 | 0.39 | 1.56 | 0.39 | 1.56 | 3.1 | 3.1 |
| P. aeruginosa A5007 | 1.56 | 1.56 | 0.78 | 0.39 | 0.2 | 0.39 | 1.56 | 0.78 |
| Acinetobacter sp CMX 669 | 0.2 | 0.1 | 0.1 | 0.05 | 0.39 | 0.2 | 0.1 | 0.2 |

| Organism | Compound of Example | | | | | | |
|---|---|---|---|---|---|---|---|
| | 46(zz) | 46(ss) | 46(bbb) | 47(b) | 47(g) | 46(cc) | 46(dd) |
| Stap. aureus ATCC-6538p | 0.02 | 0.005 | 0.01 | 0.02 | 0.05 | 0.1 | 0.05 |
| Stap. epidermis 3519 | 0.05 | 0.01 | 0.02 | 0.05 | 0.1 | 0.2 | 0.05 |
| Ent. faecium ATCC 8043 | 0.1 | 0.2 | 0.2 | 0.1 | 0.2 | 0.39 | 0.2 |
| Strep. Pyogenes EES61 | 0.05 | 0.39 | 1.56 | 0.05 | 0.78 | 0.78 | 0.39 |
| E. coli Juhl | 0.005 | 0.02 | 0.05 | 0.05 | 0.01 | 0.1 | 0.05 |
| Ent. aerogenes ATCC 13048 | 0.01 | 0.05 | 0.2 | 0.01 | 0.02 | 0.2 | 0.05 |
| K. pneumoniae ATCC 8045 | 0.005 | ≦0.005 | 0.05 | 0.005 | 0.01 | 0.05 | 0.05 |
| P. stuartii CMX 640 | 0.2 | 0.78 | >100 | 0.39 | 0.78 | 3.1 | 0.78 |
| P. aeruginosa A5007 | 0.05 | 0.39 | 0.2 | 0.2 | 0.78 | 3.1 | 0.78 |
| Acinetobacter sp CMX 669 | 0.05 | 0.02 | 0.2 | 0.05 | 0.1 | 0.1 | 0.2 |

It will be understood that various changes and modifications can be made in the details of procedure, formulation and use without departing from the spirit of the invention, especially as defined in the following claims.

What is claimed is:

1. A compound having the formula:

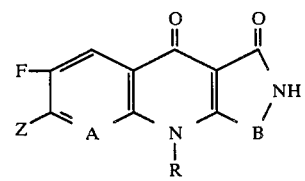

wherein B is selected from oxygen and sulfur; A is a nitrogen atom or a carbon atom substituted with a hydrogen or a halogen; R is selected from (a) $C_1$ to $C_4$ alkyl, (b) lowercycloalkyl, (c) $C_1$ to $C_4$ alkylamino, (d) a phenyl group having the formula:

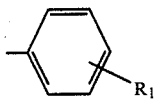

wherein $R_1$ represents three substituents which are each fluorine atoms; or $R_1$ represents one or two substituents independently selected from hydrogen, fluorine, chlorine, bromine, $C_1$ to $C_2$ alkyl, methylenedioxy, and $-OR_2$ wherein $R_2$ is hydrogen or $C_1$ to $C_4$ alkyl, (e) a group consisting of a substituted or unsubstituted aromatic heterocyclic ring selected from thiazolyl, pyridyl, pyrazinyl, furyl and thienyl, wherein the substituents are selected from $C_1$ to $C_4$ alkyl and halogen; and Z is selected from (a) an amino group of the formula:

wherein $R_3$ and $R_4$ are independently selected from hydrogen, $C_1$ to $C_4$ alkyl, $C_1$ to $C_4$ alkylamino, hydroxy-substituted $C_1$ to $C_4$ alkyl, and $NH_2$; (b) an aliphatic heterocyclic ring having the structure:

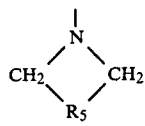

wherein $R_5$ is selected from $-(CH_2)_n-$ where n is 2 or 3 and $-(CH_2)_n-R_6-CH_2-$ wherein n is 1 or 2 and $R_6$ is selected from the group consisting of $-S-$, $-O-$ and $-N-$; and (c) said aliphatic heterocyclic ring substituted with one, two or three substituents independently selected from $C_1$ to $C_4$ alkyl, amino, $C_1$ to $C_4$ alkylamino, hydroxy-substituted $C_1$ to $C_4$ alkyl, hydroxy, $C_1$ to $C_4$ alkylaminoalkyl, halogen, and alkanoylamino; or pharmaceutically acceptable salts thereof.

2. A compound defined in claim 1 wherein R is cyclopropyl; and Z is selected from piperazinyl, 4-methyl-1-piperazinyl, 3-amino-1-pyrrolidinyl, 3-methyl-1-piperazinyl, 3-amino-4-methyl-1-pyrrolidinyl, 3-aminomethyl-4-chloro-1-pyrrolidinyl, and 3-ethylaminomethyl-1-pyrrolidinyl.

3. A compound defined in claim 1 wherein R is ethyl; and Z is selected from 1-piperazinyl, 4-methyl-1-piperazinyl, 3-amino-1-pyrrolidinyl, 3-ethylaminomethyl-1-pyrrolidinyl, 3-methyl-1-pyrrolidinyl, and 3-amino-4-methyl-1-pyrrolidinyl.

4. A compound defined in claim 1 wherein R is p-fluorophenyl; and Z is selected from 1-piperazinyl, 3-methyl-1-piperazinyl, 4-methyl-1-piperazinyl, 3-amino-1-pyrrolidinyl, and 3-amino-4-methyl-1-pyrrolidinyl.

5. A compound defined in claim 1 wherein R is o,p-difluorophenyl; and Z is selected from 1-piperazinyl, 3-methyl-1-piperazinyl, 4-methyl-1-piperazinyl, 3-amino-1-pyrrolidinyl, and 3-amino-4-methyl-1-pyrrolidinyl.

6. A compound defined in claim 1 wherein B is oxygen; R is methylamino; A is CH; and Z is 4-methyl-1-piperazinyl.

7. A compound defined in claim 1 wherein B is sulfur; R is methylamino; A is CH; and Z is 4-methyl-1-piperazinyl.

8. A composition having antibacterial activity in pharmaceutical dosage form containing a diluent and a therapeutically effective amount of a compound as defined in claim 1.

9. A method of treating a bacterial infection in a patient comprising administering to a patient in need of such treatment a therapeutically effective amount of a compound as defined in claim 1.

10. A compound having the formula

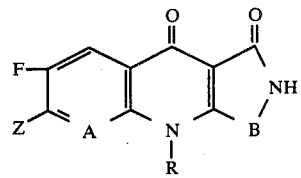

wherein B is selected from oxygen and sulfur; R is cyclopropyl; A is selected from CH, CCl, CF, and N; and Z is selected from piperazinyl, 4-methyl-1-piperazinyl, 3-ethylaminomethyl-1-pyrrolidinyl, 3-methyl-1-piperazinyl, 3-amino-4-methyl-1-pyrrolidinyl, and 3-amino-1-pyrrolidinyl.

11. The compound as recited in claim 10 wherein Z is selected from piperazinyl, 4-methyl-1-piperazinyl, and 3-amino-1-pyrrolidinyl; A is selected from CH and CF; and B is sulfur.

12. The compound as recited in claim 10 wherein Z is selected from piperazinyl, 4-methyl-1-piperazinyl, and 3-amino-1-pyrrolidinyl; A is nitrogen; and B is sulfur.

13. The compound as recited in claim 10 wherein Z is selected from piperazinyl, 3-amino-1-pyrrolidinyl, and 4-methyl-1-piperazinyl; A is CCl; and B is sulfur.

14. The compound as recited in claim 10 wherein Z is selected from piperazinyl, 4-methyl-1-piperazinyl, and 3-amino-1-pyrrolidinyl; A is CH or CF; and B is oxygen.

15. The compound as recited in claim 10 wherein Z is selected from piperazinyl, 4-methyl-1-piperazinyl, and 3-amino-1-pyrrolidinyl; A is nitrogen and B is oxygen.

16. The compound as recited in claim 10 wherein Z is selected from piperazinyl, 4-methyl-1-piperazinyl, and 3-amino-1-pyrrolidinyl; A isCCl; and B is oxygen.

17. The compound as recited in claim 10 wherein Z is piperazinyl; A is CF; and B is sulfur.

18. The compound as recited on claim 10 wherein Z is 3-amino-1-pyrrolidinyl; A is CF; and B is sulfur.

19. The compound as recited in claim 10 wherein Z is piperazinyl; A is CH; and B is sulfur.

20. The compound as recited in claim 10 wherein Z is piperazinyl; A is nitrogen; and B is sulfur.

21. The compound as recited in claim 10 wherein Z is 3-amino-1-pyrrolidinyl; A is nitrogen; and B is sulfur.

22. The compound as recited in claim 10 wherein Z is 3-amino-1-pyrrolidinyl; A is CCl; and B is sulfur.

23. The compound as recited in claim 10 wherein Z is 3-amino-1-pyrrolidinyl; A is CH; and B is sulfur.

24. The compound as recited in claim 10 wherein Z is piperazinyl; A is CH; and B is oxygen.

25. The compound as recited in claim 10 wherein Z is 3-amino-1-pyrrolidinyl; A is CH; and B is oxygen.

26. The compound as recited in claim 10 wherein Z is piperazinyl; A is CF; and B is oxygen.

27. The compound as recited in claim 10 wherein Z is 3-amino-1-pyrrolidinyl; A is CF; and B is oxygen.

28. The compound as recited in claim 10 wherein Z is 3-amino-1-pyrrolidinyl; A is CCl; and B is oxygen.

29. The compound as recited in claim 10 wherein Z is piperazinyl; A is nitrogen; and B is oxygen.

30. The compound as recited in claim 10 wherein Z is 3-amino-1-pyrrolidinyl; A is nitrogen; and B is oxygen.

31. A compound having a formula

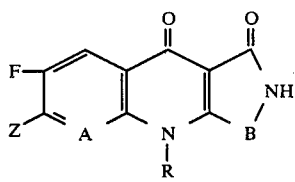

wherein B is selected from oxygen and sulfur; R is ethyl; and Z is selected from piperazinyl, 4-methyl-1-piperazinyl, 3-amino-1-pyrrolidinyl, 3-ethylaminomethyl-1-pyrrolidinyl, 3-methyl-1-piperazinyl, and 3-amino-4-methyl-1-pyrrolidinyl; and A is selected from CH, CCl, CF, and N.

32. The compound as recited in claim 31 wherein Z is 3-amino-1-pyrrolidinyl; B is sulfur; and A is CH.

33. The compound as recited in claim 31 wherein Z is 3-amino-1-pyrrolidinyl; B is sulfur; and A is CF.

34. The compound as recited in claim 31 wherein Z is piperazinyl; B is sulfur; and A is CF.

35. The compound as recited in claim 31 wherein Z is 3-amino-1-pyrrolidinyl; B is sulfur; and A is CCl.

36. The compound as recited in claim 31 wherein A is piperazinyl; B is sulfur; and A is nitrogen.

37. The compound as recited in claim 31 wherein Z is 3-amino-1-pyrrolidinyl; B is sulfur; and A is nitrogen.

38. The compound as recited in claim 31 wherein Z is 3-amino-1-pyrrolidinyl; B is oxygen; and A is CH.

39. The compound as recited in claim 31 wherein Z is piperazinyl; B is oxygen; and A is CH.

40. The compound as recited in claim 31 wherein Z is 3-amino-1-pyrrolidinyl; B is oxygen; and A is CF.

41. The compound as recited in claim 31 wherein Z is piperazinyl; B is oxygen and A is CF.

42. The compound as recited in claim 31 wherein Z is 3-amino-1-pyrrolidinyl; B is oxygen; and A is CCl.

43. The compound as recited in claim 31 wherein Z is 3-amino-1-pyrrolidinyl; B is oxygen; and A is nitrogen.

44. The compound as recited in claim 31 wherein Z is piperazinyl; B is oxygen; and A is nitrogen.

45. A compound having the formula

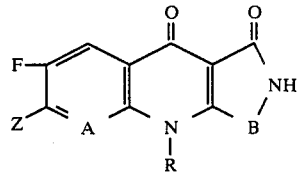

wherein B is selected from oxygen and sulfur; R is p-fluorophenyl; and Z is selected from piperazinyl, 3-methyl-1-piperazinyl, 4-methyl-1-piperazinyl, 3-amino-1-pyrrolidinyl, and 3-amino-4-methyl-1-pyrrolidinyl; and A is selected from CH, CF, CCl, and N.

46. The compound as recited in claim 45 wherein Z is 3-amino-1-pyrrolidinyl.

47. The compound as recited in claim 46 wherein A is CH.

48. The compound as recited in claim 46 wherein A is DF.

49. The compound as recited in claim 46 wherein A is nitrogen.

50. A compound having the formula

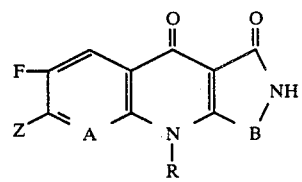

wherein B is selected from oxygen and sulfur; R is o,p-difluorophenyl; Z is selected from piperazinyl, 3-methyl-1-piperazinyl, 4-methyl-1-piperazinyl, 3-amino-1-pyrrolidinyl, and 3-amino-4-methyl-1-pyrrolidinyl; A is selected from CH, CF, and N.

51. The compound as recited in claim 50 wherein Z is 3-amino-1-pyrrolidinyl; and B is sulfur.

* * * * *